US007910702B2

(12) United States Patent
Kav et al.

(10) Patent No.: US 7,910,702 B2
(45) Date of Patent: Mar. 22, 2011

(54) RECOMBINANT ANTIBODIES TO SCLEROTINIA ANTIGENS

(75) Inventors: Nataraj Kav, Edmonton (CA); William Yajima, Edmonton (CA); Bo Yang, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 409 days.

(21) Appl. No.: 11/829,513

(22) Filed: Jul. 27, 2007

(65) Prior Publication Data

US 2008/0104734 A1 May 1, 2008

Related U.S. Application Data

(60) Provisional application No. 60/820,626, filed on Jul. 28, 2006.

(51) Int. Cl.
*C12P 21/08* (2006.01)
*G01N 33/02* (2006.01)
(52) U.S. Cl. .................. 530/387.3; 435/7.92; 424/274.1
(58) Field of Classification Search .................... None
See application file for complete search history.

(56) References Cited

U.S. PATENT DOCUMENTS

| 5,187,064 A * | 2/1993 | Petersen et al. ............. 435/7.31 |
| 5,607,914 A * | 3/1997 | Rao et al. .................. 514/12 |
| 2003/0119013 A1 * | 6/2003 | Jiang et al. ................ 435/6 |

OTHER PUBLICATIONS

Bom M, Boland GJ. Evaluation of polyclonal-antibody-based immunoassays for detection of Sclerotinia sclerotiorum on canola petals, and prediction of stem rot. Can J Microbiol. Aug. 2000;46(8):723-9.*
Jamaux et al. Development of a polyclonal antibody-based immunoassay for the early detection of Sclerotinia sclerotiorum in rapeseed petals. Plant Pathology, Oct. 1994, vol. 43 Issue 5, p. 847-862.*
Li et al. Interaction of Sclerotinia sclerotiorum with Brassica napus: cloning and characterization of endo- and exo-polygalacturonases expressed during saprophytic and parasitic modes. Fungal Genet Biol. Aug. 2004;41(8):754-65.*
Friguet, Bertrand et al., Measurements of the True Affinity Constant in Solution of Antigen-Antibody Complexes by Enzyme-Linked Immunosorbent Assay, Journal of Immunological Methods, 1985, vol. 77, pp. 305-319, Elsevier Science Publishers B.V. (Biomedical Division).
Krebber, Anke et al., Reliable Cloning of Functional Antibody Variable Domains from Hybridomas and Spleen Cell Repertoires Employing a Reengineered Phage Display System, Journal of Immunological Methods, 1997, vol. 201, pp. 35-55, Elsevier Science B.V.
Cao, Y. et al., Development of Bispecific Monoclonal Antibody as a Universal Immunoprobe for Detecting Biotinylated Macromolecules, Journal of Immunological Methods, 1998, vol. 220, pp. 85-91, Elsevier Science B.V.
Schillberg, Stefan et al., Antibody-Based Resistance to Plant Pathogens, Transgenic Research, 2001, vol. 10, pp. 1-12, Kluwer Academic Publishers, Netherlands.
Tout, Nancy L. et al., Synthesis of Ligand-Specific Phage-Display ScFv Against the Herbicide Picloram by Direct Cloning from Hyperimmunized Mouse, J. Agric. Food Chem., 2001, vol. 49, pp. 3628-3637, American Chemical Society.
Peschen, Dieter et al., Fusion Proteins Comprising a Fusarium-Specific Antibody Linked to Antifungal Peptides Protect Plants Against a Fungal Pathogen, Nature Biotechnology, 2004, vol. 22, pp. 732-738, Nature Publishing Group.
Tavladoraki, Paraskevi et al., Transgenic Plants Expressing a Functional Single-Chain Fv Antibody Are Specifically Protected from Virus Attack, Letters to Nature, 1993, vol. 366, pp. 469-472, Nature Publishing Group.
Kriangkum, D. Das et al., Development of a Biotin Mimic Tagged ScFv Antibody Against Western Equine Encephalitis Virus: Bacterial Expression and Refolding, Journal of Virological Methods, 2004, vol. 117, pp. 169-177, Elsevier B.V.

* cited by examiner

*Primary Examiner* — David S Romeo
(74) *Attorney, Agent, or Firm* — Bennett Jones LLP

(57) ABSTRACT

The invention is directed to recombinant antibodies which bind to *Sclerotinia sclerotiorum* antigens and comprise a single chain variable fragment (scFv). The antigen may be selected from SSPG1d or a portion thereof, aspartyl protease or a portion thereof, or whole *Sclerotinia sclerotiorum* mycelium. The invention also provides an antibody linked to an anti-fungal polypeptide. The invention extends to nucleic acid sequences encoding the antibodies, and expression vectors comprising the nucleic acid sequences. The invention is also directed to transgenic plants, seeds, tissues or cells transformed with the expression vectors. Methods for producing a transgenic plant that is resistant to *Sclerotinia sclerotiorum*, and for detecting *Sclerotinia sclerotiorum* in a biological sample utilizing an antibody which binds to *Sclerotinia sclerotiorum* antigen, and immunoassay kit for same are also provided.

8 Claims, 19 Drawing Sheets

GGSQVQLKQSGAELAKPGASVKMSCKASGYTFTSYWMHWVKQRPGQGLEWIGYINPSTGYTEYNQKFKDKATLT
ADKSSSTAYMQLSSLTSEDSAVYYCARKFYGNFPMDYWGQGTSVTVSS-

H
DNA sequence (SEQ ID NO:15)
atgGATATTGTGATGACCCAGTCTCCAGCACTCATGTCTGCATCTCCAGGGGAGAAGGTCACCATGACCTGCAGT
GCCAGCTCAAGTGTAAGTTACATGTACTGGTACCAGCAGAAGCCAAGATCCTCCCCCAAACCCTGGATTTATCT
CACATCCAACCTGGCTTCTGGAGTCCCTGCTCGCTTCAGTGGCAGTGGGTCTGGGACCTCTTACTCTCTCACAA
TCAGCAGCATGGAGGCTGAAGATGCTGCCACTTATTACTGCCAGCAGTGGAGTAGTAACCCGTACACGTTCGG
AGGGGGGACCAAGCTGGAAATAAAACGTGGTGGTGGTGGTTCTGGTGGTGGTGGTTCTGGCGGCGGCGGCTCC
GGTGGTGGTGGATCCGACGTGATGGTGGTGGAGTCTGGGGGAGGCTTAGTGAAGCCTGGAGGGTCCCTGAAAC
TCTCCTGTGCAGCCTCTGGATTCACTTTCAGTAGCTATGCCATGTCTTGGGTTCGCCAGACTCCGGAGAAGAGG
CTGGAGTGGGTCGCAACCATTAGTAGTGGTGGTAGTTACACCTACTATCCAAACAGTGTGAAGGGGCGATTCA
CCATCTCCAGAGACAATGCCAAGAACACCCTGTACCTGCAAATGAGCCGTCTGAAGTCTGAGGACACAGCCAT
GTATTACTGTGCAAGACGGAGTGAACTGGGACTGTTTGCTTACTGGGGCCAAGGGACTCTGGTCACTGTCTCTG
CGtaa

Amino acid sequence (SEQ ID NO:16)
MDIVMTQSPALMSASPGEKVTMTCSASSSVSYMYWYQQKPRSSPKPWIYLTSNLASGVPARFSGSGSGTSYSLTISS
MEAEDAATYYCQQWSSNPYTFGGGTKLEIKRGGGGSGGGGSGGGGSGGGGSDVMVVESGGGLVKPGGSLKLSCA
ASGFTFSSYAMSWVRQTPEKRLEWVATISSGGSYTYYPNSVKGRFTISRDNAKNTLYLQMSRLKSEDTAMYYCARR
SELGLFAYWGQGTLVTVSA-

FIG. 1

DNA sequence (SEQ ID NO:1)
atgGACATTGTGTTGACACAGTCTCCAGCAATCATGTCTGCATCTCCAGGGGAAAAGGTCACCATGACCTGCAGT
GCCAGCTCAAGTGTAAGTTACATGCACTGGTACCAGCAGAAGTCAAGCACCTCCCCCAAACTCTGGATTTATG
ACACATCCAAACTGGCTTCTGGAGTCCCAGGTCGCTTCAGTGGCAGTGGGTCTGGAAACTCTTACTCTCTCACG
ATCAGCAGCATGGAGGCTGAAGATGTTGCCACTTATTACTGTTTTCAGGGGAGTGGGTACCCGCTCACGTTCGG
TGCTGGGACCAAGCTGGAAATCAAACGTGGTGCTGGTGGTTCTGGTGGTGGTGGTTCTGGCGGCGGCGGCTCC
GGTGGTGGTGGATCCCAGGTCCAGCTTCAGCAATCTGGGGCTGAGCTGGTGAGGCCTGGGTCCTCAGTGAAGA
TTTCCTGCAAGGCTTCTGGCTATGCATTCAGTAACTACTGGATGAACTGGGTGAAGCAGAGGCCTGGACAGGG
TCTTGAGTGGATTGGACAGATTTATCCTGGATATGGTGATGCTAAATACAATGGAAAGTTCAAGGGTAAGGCC
ACGCTGACTGCAGACATATCCTCCAGCACAGCCTATATGCAGCTCAGCAGCCTAACATCTGAGGACTCTGCAG
TCTATTTCTGTGCAAGATCATCTTACGAGGCTAACTGGGGCCAAGGGACTCTGGTCACTGTCTCTGCGtaa

Amino acid sequence (SEQ ID NO:2)
MDIVLTQSPAIMSASPGEKVTMTCSASSSVSYMHWYQQKSSTSPKLWIYDTSKLASGVPGRFSGSGSGNSYSLTISS
MEAEDVATYYCFQGSGYPLTFGAGTKLEIKRGAGGSGGGGSGGGGSGGGGSQVQLQQSGAELVRPGSSVKISCKA
SGYAFSNYWMNWVKQRPGQGLEWIGQIYPGYGDAKYNGKFKGKATLTADISSSTAYMQLSSLTSEDSAVYFCARS
SYEANWGQGTLVTVSA-

FIG. 1A

DNA sequence (SEQ ID NO:3)
atgGATATTGTGATGACCCAGTCTCACAAATTCATGTCCACATCAGTAGGAGACAGGGTCAGCATCACCTGCAA
GGCCAGTCAGGATGTGGGTACTGCTGTAGCCTGGTATCAACAGAAACCAGGGCAATCTCCTAAACTACTGATT
TACTGGGCATCCACCCGGCACACTGGAGTCCCTGATCGCTTCACAGGCAGTGGATCTGGGACAGATTTCACTCT
CACCATTAGCAATGTGCAGTCTGAAGACTTGGCAGATTATTTCTGTCAGCAATATAGCAGCTATCCTCGGACGT
TCGGTGGAGGCACCAAGCTGGAAATCAAACGTGGTGGTGGTGGTTCTGGTGGTGGTGGTTCTGGCGGCGGCGG
CTCCGGTGGTGGTGGATCCGAGGTGCAGCTTCAGCAGTCTGGGGCAGACCTTGTGAGGTCAGGGGCCTCAGTC
AAGTTGTCCTGCACAGCTTCTGGCTTCAACATTAAAGACTACTATATCCACTGGGTGAAGCAGAGGCCTGAAC
AGGGCCTGGCGTGGATTGGATGGATTGATCCTGAGAATGGTGATACTGAATATGCCCCGAAGTTCCAGGACAA
GGCCACTTTGACTGCAGACACATCTTCCAATACAGCCTACCTGCAGCTCAGCAGCCTGACATCTGAGGACACTG
CCGTCTATTACTGTAATGCATGGGCTGGGACGTCAGGGGCCTGGTTTGCTTACTGGGGCCAAGGGACTCTGGTC
ACTGTCTCTGCGtaa

Amino acid sequence (SEQ ID NO:4)
MDIVMTQSHKFMSTSVGDRVSITCKASQDVGTAVAWYQQKPGQSPKLLIYWASTRHTGVPDRFTGSGSGTDFTLTI
SNVQSEDLADYFCQQYSSYPRTFGGGTKLEIKRGGGGSGGGGSGGGGSGGGGSEVQLQQSGADLVRSGASVKLSC
TASGFNIKDYYIHWVKQRPEQGLAWIGWIDPENGDTEYAPKFQDKATLTADTSSNTAYLQLSSLTSEDTAVYYCNA
WAGTSGAWFAYWGQGTLVTVSA-

FIG. 1B

DNA sequence (SEQ ID NO:5)
atgGATATTGTTCTCTCCCAGTCTCCAACAATCATGTCTGCATCTCCAGGGGAGAAGGTCACCATGACCTGCAGT
GCCAGCTCAAGTGTAAGTTACATGCACTGGTACCAGCAGAAGTCAGGCACCTCCCCCAAAAGATGGATTTATG
ACACATCCAAACTGGCTTCTGGAGTCCCTGCTCGCTTCAGTGGCAGTGGGTCTGGGACCCCTTACCCTCTCACA
ATCAGCAGCATGGAGGCTGAAGATGCTGCCACTTATTACTGCCTGCAGTGGAGTAGTAACCCGTGGACGTTCG
GTGGAGGCACCAAGCTGGAGCTGAAACGTGGTGGTGGTGGTTCTGGTGGTGGTGGTTCTGGCGGCGGCGGCTC
CGGTGGTGGTGGATCCCAGGTGCAGCTGAAGCAATCTGGGGCTGAACTGGCAAAACCTGGGGCCTCAGTGAAG
ATGTCCTGCAAGGCTTCTGGCTACACCTTTACTAGCTACTGGATGCACTGGGTAAAACAGAGGCCTGGACAGG
GTCTGGAATGGATTGGATACATTAATCCTAGCACTGGTTATACTGAGTACAATCAGAAGTTCAAGGACAAGGC
CACATTGACTGCAGACAAATCCTCCAGCACAGCCTACATGCAACTGAGCAGCCTGACATCTGAGGACTCTGCA
GTCTATTACTGTGCAAGAAAGTTCTATGGTAACTTCCCTATGGACTACTGGGGTCAAGGAACCTCAGTCACCGT
CTCCTCGtaa

Amino acid sequence (SEQ ID NO:6)
MDIVLSQSPTIMSASPGEKVTMTCSASSSVSYMHWYQQKSGTSPKRWIYDTSKLASGVPARFSGSGSGTPYPLTISS
MEAEDAATYYCLQWSSNPWTFGGGTKLELKRGGGGSGGGGSGGGGSGGGGSQVQLKQSGAELAKPGASVKMSC
KASGYTFTSYWMHWVKQRPGQGLEWIGYINPSTGYTEYNQKFKDKATLTADKSSSTAYMQLSSLTSEDSAVYYCA
RKFYGNFPMDYWGQGTSVTVSS-

FIG. 1C

DNA sequence (SEQ ID NO:7)
atgGATATTGTTCTCTCCCAGTCTCCAACAATCATGTCTGCATCTCCAGGGGAGAAGGTCACCATGACCTGCAGT
GCCAGCTCAAGTGTAAGTTACATGCACTGGTACCAGCAGAAGTCAGGCACCTCCCCCAAAAGATGGATTTATG
ACACATCCAAACTGGCTTCTGGAGTCCCTGCTCGCTTCAGTGGCAGTGGGTCTGGGACCCCTTACCCTCTCACA
ATCAGCAGCATGGAGGCTGAAGATGCTGCCACTTATTACTGCCTGCAGTGGAGTAGTAACCCGTGGACGTTCG
GTGGAGGCACCAAGCTGGAGCTGAAACGTGGTGGTGGTGGTTCTGGTGGTGGTGGTTCTGGCGGCGGCGGCTC
CGGTGGTGGTGGATCCCAGGTGCAGCTGAAGCAATCTGGGGCTGAACTGGCAAAACCTGGGGCCTCAGTGAAG
ATGTCCTGCAAGGCTTCTGGCTACACCTTTACTAGCTACTGGATGCACTGGGTAAAACAGAGGCCTGGACAGG
GTCTGGAATGGATTGGATACATTAATCCTAGCACTGGTTATACTGAGTACAATCAGAAGTTCAAGGACAAGGC
CACATTGACTGCAGACAAATCCTCCAGCACAGCCTACATGCAACTGAGCAGCCTGACATCTGAGGACTCTGCA
GTCTATTACTGTGCAAGAAAGTTCTATGGTAACTTCCCTATGGACTACTGGGGTCAAGGAACCTCAGTCACCGT
CTCCTCGGGAGGAGGAGGATCAGGAGGAGGAGGATCAGATATGGATATTGTTCTCTCCCAGTCTCCAACAATC
ATGTCTGCATCTCCAGGGGAGAAGGTCACCATGACCTGCAGTGCCAGCTCAAGTGTAAGTTACATGCACTGGT
ACCAGCAGAAGTCAGGCACCTCCCCCAAAAGATGGATTTATGACACATCCAAACTGGCTTCTGGAGTCCCTGC
TCGCTTCAGTGGCAGTGGGTCTGGGACCCCTTACCCTCTCACAATCAGCAGCATGGAGGCTGAAGATGCTGCC
ACTTATTACTGCCTGCAGTGGAGTAGTAACCCGTGGACGTTCGGTGGAGGCACCAAGCTGGAGCTGAAACGTG
GTGGTGGTGGTTCTGGTGGTGGTGGTTCTGGCGGCGGCGGCTCCGGTGGTGGTGGATCCCAGGTGCAGCTGAA
GCAATCTGGGGCTGAACTGGCAAAACCTGGGGCCTCAGTGAAGATGTCCTGCAAGGCTTCTGGCTACACCTTT
ACTAGCTACTGGATGCACTGGGTAAAACAGAGGCCTGGACAGGGTCTGGAATGGATTGGATACATTAATCCTA
GCACTGGTTATACTGAGTACAATCAGAAGTTCAAGGACAAGGCCACATTGACTGCAGACAAATCCTCCAGCAC
AGCCTACATGCAACTGAGCAGCCTGACATCTGAGGACTCTGCAGTCTATTACTGTGCAAGAAAGTTCTATGGTA
ACTTCCCTATGGACTACTGGGGTCAAGGAACCTCAGTCACCGTCTCCTCGtaa

Amino acid sequence (SEQ ID NO:8)
MDIVLSQSPTIMSASPGEKVTMTCSASSSVSYMHWYQQKSGTSPKRWIYDTSKLASGVPARFSGSGSGTPYPLTI
SSMEAEDAATYYCLQWSSNPWTFGGGTKLELKRGGGGSGGGGSGGGGSGGGGSQVQLKQSGAELAKPGASVKMSC
KASGYTFTSYWMHWVKQRPGQGLEWIGYINPSTGYTEYNQKFKDKATLTADKSSSTAYMQLSSLTSEDSAVYYCA
RKFYGNFPMDYWGQGTSVTVSSGGGGSGGGGSHMDIVLSQSPTIMSASPGEKVTMTCSASSSVSYMHWYQQKSGT
SPKRWIYDTSKLASGVPARFSGSGSGTPYPLTISSMEAEDAATYYCLQWSSNPWTFGGGTKLELKRGGGGSGGGG
SGGGGSGGGGSQVQLKQSGAELAKPGASVKMSCKASGYTFTSYWMHWVKQRPGQGLEWIGYINPSTGYTEYNQKF
KDKATLTADKSSSTAYMQLSSLTSEDSAVYYCARKFYGNFPMDYWGQGTSVTVSS-

FIG. 1D

DNA sequence (SEQ ID NO:9)
atgCAGAAGTTGTGCGAAAGGCCAAGTGGGACATGGTCAGGAGTCTGTGGAAACAATAACGCATGCAAGAATC
AGTGCATTAACCTTGAGAAAGCACGACATGGATCTTGCAACTATGTCTTCCCAGCTCACAAGTGTATCTGCTAC
TTTCCTTGTGGTGGTGGTGGTTCTGGCGGCGGCGGCTCCGATATTGTTCTCTCCCAGTCTCCAACAATCATGTCT
GCATCTCCAGGGGAGAAGGTCACCATGACCTGCAGTGCCAGCTCAAGTGTAAGTTACATGCACTGGTACCAGC
AGAAGTCAGGCACCTCCCCCAAAAGATGGATTTATGACACATCCAAACTGGCTTCTGGAGTCCCTGCTCGCTTC
AGTGGCAGTGGGTCTGGGACCCCTTACCCTCTCACAATCAGCAGCATGGAGGCTGAAGATGCTGCCACTTATT
ACTGCCTGCAGTGGAGTAGTAACCCGTGGACGTTCGGTGGAGGCACCAAGCTGGAGCTGAAACGTGGTGGTGG
TGGTTCTGGTGGTGGTGGTTCTGGCGGCGGCGGCTCCGGTGGTGGTGGATCCCAGGTGCAGCTGAAGCAATCT
GGGGCTGAACTGGCAAAACCTGGGGCCTCAGTGAAGATGTCCTGCAAGGCTTCTGGCTACACCTTTACTAGCT
ACTGGATGCACTGGGTAAAACAGAGGCCTGGACAGGGTCTGGAATGGATTGGATACATTAATCCTAGCACTGG
TTATACTGAGTACAATCAGAAGTTCAAGGACAAGGCCACATTGACTGCAGACAAATCCTCCAGCACAGCCTAC
ATGCAACTGAGCAGCCTGACATCTGAGGACTCTGCAGTCTATTACTGTGCAAGAAAGTTCTATGGTAACTTCCC
TATGGACTACTGGGGTCAAGGAACCTCAGTCACCGTCTCCTCGtaa

Amino acid sequence (SEQ ID NO:10)
MQKLCERPSGTWSGVCGNNNACKNQCINLEKARHGSCNYVFPAHKCICYFPCGGGGSGGGGSDIVLSQSPTIMSAS
PGEKVTMTCSASSSVSYMHWYQQKSGTSPKRWIYDTSKLASGVPARFSGSGSGTPYPLTISSMEAEDAATYYCLQW
SSNPWTFGGGTKLELKRGGGGSGGGGSGGGGSGGGGSQVQLKQSGAELAKPGASVKMSCKASGYTFTSYWMHW
VKQRPGQGLEWIGYINPSTGYTEYNQKFKDKATLTADKSSSTAYMQLSSLTSEDSAVYYCARKFYGNFPMDYWGQ
GTSVTVSS-

FIG. 1E

DNA sequence (SEQ ID NO:11)
atgGCTAAGTTTGCGTCCATCATCGCACTTCTTTTTGCTGCTCTTGTTCTTTTTGCTGCTTTCGAAGCACCAACAAT
GGTGGAAGCACAGAAGTTGTGCGAAAGGCCAAGTGGGACATGGTCAGGAGTCTGTGGAAACAATAACGCATG
CAAGAATCAGTGCATTAACCTTGAGAAAGCACGACATGGATCTTGCAACTATGTCTTCCCAGCTCACAAGTGT
ATCTGCTACTTTCCTTGTGGTGGTGGTGGTTCTGGCGGCGGCGGCTCCGATATTGTTCTCTCCCAGTCTCCAACA
ATCATGTCTGCATCTCCAGGGGAGAAGGTCACCATGACCTGCAGTGCCAGCTCAAGTGTAAGTTACATGCACT
GGTACCAGCAGAAGTCAGGCACCTCCCCCAAAAGATGGATTTATGACACATCCAAACTGGCTTCTGGAGTCCC
TGCTCGCTTCAGTGGCAGTGGGTCTGGGACCCCTTACCCTCTCACAATCAGCAGCATGGAGGCTGAAGATGCTG
CCACTTATTACTGCCTGCAGTGGAGTAGTAACCCGTGGACGTTCGGTGGAGGCACCAAGCTGGAGCTGAAACG
TGGTGGTGGTGGTTCTGGTGGTGGTGGTTCTGGCGGCGGCGGCTCCGGTGGTGGTGGATCCCAGGTGCAGCTG
AAGCAATCTGGGGCTGAACTGGCAAAACCTGGGGCCTCAGTGAAGATGTCCTGCAAGGCTTCTGGCTACACCT
TTACTAGCTACTGGATGCACTGGGTAAAACAGAGGCCTGGACAGGGTCTGGAATGGATTGGATACATTAATCC
TAGCACTGGTTATACTGAGTACAATCAGAAGTTCAAGGACAAGGCCACATTGACTGCAGACAAATCCTCCAGC
ACAGCCTACATGCAACTGAGCAGCCTGACATCTGAGGACTCTGCAGTCTATTACTGTGCAAGAAAGTTCTATG
GTAACTTCCCTATGGACTACTGGGGTCAAGGAACCTCAGTCACCGTCTCCTCGtaa

Amino acid sequence (SEQ ID NO:12)
MAKFASIIALLFAALVLFAAFEAPTMVEAQKLCERPSGTWSGVCGNNNACKNQCINLEKARHGSCNYVFPAHKCIC
YFPCGGGGSGGGGSDIVLSQSPTIMSASPGEKVTMTCSASSSVSYMHWYQQKSGTSPKRWIYDTSKLASGVPARFS
GSGSGTPYPLTISSMEAEDAATYYCLQWSSNPWTFGGGTKLELKRGGGGSGGGGSGGGGSGGGGSQVQLKQSGAE
LAKPGASVKMSCKASGYTFTSYWMHWVKQRPGQGLEWIGYINPSTGYTEYNQKFKDKATLTADKSSSTAYMQLS
SLTSEDSAVYYCARKFYGNFPMDYWGQGTSVTVSS-

FIG. 1F

DNA sequence (SEQ ID NO:13)
atgAAGTCTTGTCTACTTCTCTTTCTCATCTTCTCATTTCTTTTATCATTTTCCTTAGCCGAGCAATGTGGTCGACA
AGCGGGAGGAGCTCTCTGCCCCAACGGTCTATGCTGCAGCGAGTTCGGATGGTGCGGTGACACCGAAGCTTAC
TGTAAGCAGCCTGGCTGCCAAAGCCAGTGCGGTGGTACTCCTCCTGGCCCCACCGGTGATCTTTCAGGCATCAT
TTCAAGATCTCAGTTCGACGACATGCTTAAACATAGAAATGATAATGCTTGTCCCGCTAGAGGTTTCTACACTT
ATGATGCCTTTATCAATGCCGCTAAGTCTTTCCCTGGCTTCGGCACCACCGGAGACACTGCCACAAGGAAGAA
AGAAATCGCTGCCTTCTTTGGTCAGACTTCCCACGAGACCACCGGTGGGTGGGCCACAGCACCAGACGGACCA
TATTCATGGGGATACTGTTTCAAACAAGAGCAGAACCCTTCTTCAAACTACTGTTCACCGAGTGCCGAATGGCC
ATGCGCATCTGGTAAAAGCTACTACGGAAGAGGACCAATGCAGCTATCATGGAACTACAACTACGGACAGTGT
GGAAGAGCCATCGGATCTGACTTACTCAACAACCCTGACCTTGTCTCCAACGATCCAGTGATCGCTTTCAAAGC
CGCGATTTGGTTTTGGATGACACCTCAGTCTCCAAAACCGTCGTGCCACGCCGTGATCGTCGGCCAGTGGCAGC
CTTCGGATGCTGACCGTGCCGCTGGGAGGTACCGGGTTACGGTGTGATTACGAATATTATTAACGGTGGTTTA
GAGTGTGGACGCGGCCAAGACGCTAGAGTCGCGGATAGAATTGGATTTTACCAGAGGTACTGTAACATTCTTG
GAGTTAATCCTGGAGGTAACCTTGATTGTTACAACCAAAGGTCCTTTGCTTCTGTTAACTTCTTCCTTGACGCTG
CTATTGGTGGTGGTGGTTCTGGCGGCGGCGGCTCCGATATTGTTCTCTCCCAGTCTCCAACAATCATGTCTGCAT
CTCCAGGGGAGAAGGTCACCATGACCTGCAGTGCCAGCTCAAGTGTAAGTTACATGCACTGGTACCAGCAGAA
GTCAGGCACCTCCCCCAAAAGATGGATTTATGACACATCCAAACTGGCTTCTGGAGTCCCTGCTCGCTTCAGTG
GCAGTGGGTCTGGGACCCCTTACCCTCTCACAATCAGCAGCATGGAGGCTGAAGATGCTGCCACTTATTACTGC
CTGCAGTGGAGTAGTAACCCGTGGACGTTCGGTGGAGGCACCAAGCTGGAGCTGAAACGTGGTGGTGGTGGTT
CTGGTGGTGGTGGTTCTGGCGGCGGCGGCTCCGGTGGTGGTGGATCCCAGGTGCAGCTGAAGCAATCTGGGGC
TGAACTGGCAAAACCTGGGGCCTCAGTGAAGATGTCCTGCAAGGCTTCTGGCTACACCTTTACTAGCTACTGGA
TGCACTGGGTAAAACAGAGGCCTGGACAGGGTCTGGAATGGATTGGATACATTAATCCTAGCACTGGTTATAC
TGAGTACAATCAGAAGTTCAAGGACAAGGCCACATTGACTGCAGACAAATCCTCCAGCACAGCCTACATGCAA
CTGAGCAGCCTGACATCTGAGGACTCTGCAGTCTATTACTGTGCAAGAAAGTTCTATGGTAACTTCCCTATGGA
CTACTGGGGTCAAGGAACCTCAGTCACCGTCTCCTCGtaa

Amino acid sequence (SEQ ID NO:14)
MKSCLLLFLIFSFLLSFSLAEQCGRQAGGALCPNGLCCSEFGWCGDTEAYCKQPGCQSQCGGTPPGPTGDLSGIISRS
QFDDMLKHRNDNACPARGFYTYDAFINAAKSFPGFGTTGDTATRKKEIAAFFGQTSHETTGGWATAPDGPYSWGY
CFKQEQNPSSNYCSPSAEWPCASGKSYYGRGPMQLSWNYNYGQCGRAIGSDLLNNPDLVSNDPVIAFKAAIWFWM
TPQSPKPSCHAVIVGQWQPSDADRAAGRVPGYGVITNIINGGLECGRGQDARVADRIGFYQRYCNILGVNPGGNLD
CYNQRSFASVNFFLDAAIGGGGSGGGGSDIVLSQSPTIMSASPGEKVTMTCSASSSVSYMHWYQQKSGTSPKRWIY
DTSKLASGVPARFSGSGSGTPYPLTISSMEAEDAATYYCLQWSSNPWTFGGGTKLELKRGGGGSGGGGSGGGGSGG
GGSQVQLKQSGAELAKPGASVKMSCKASGYTFTSYWMHWVKQRPGQGLEWIGYINPSTGYTEYNQKFKDKATLT
ADKSSSTAYMQLSSLTSEDSAVYYCARKFYGNFPMDYWGQGTSVTVSS-

FIG. 1G

DNA sequence (SEQ ID NO:15)
atgGATATTGTGATGACCCAGTCTCCAGCACTCATGTCTGCATCTCCAGGGGAGAAGGTCACCATGACCTGCAGT
GCCAGCTCAAGTGTAAGTTACATGTACTGGTACCAGCAGAAGCCAAGATCCTCCCCCAAACCCTGGATTTATCT
CACATCCAACCTGGCTTCTGGAGTCCCTGCTCGCTTCAGTGGCAGTGGGTCTGGGACCTCTTACTCTCTCACAA
TCAGCAGCATGGAGGCTGAAGATGCTGCCACTTATTACTGCCAGCAGTGGAGTAGTAACCCGTACACGTTCGG
AGGGGGGACCAAGCTGGAAATAAAACGTGGTGGTGGTGGTTCTGGTGGTGGTGGTTCTGGCGGCGGCGGCTCC
GGTGGTGGTGGATCCGACGTGATGGTGGTGGAGTCTGGGGGAGGCTTAGTGAAGCCTGGAGGGTCCCTGAAAC
TCTCCTGTGCAGCCTCTGGATTCACTTTCAGTAGCTATGCCATGTCTTGGGTTCGCCAGACTCCGGAGAAGAGG
CTGGAGTGGGTCGCAACCATTAGTAGTGGTGGTAGTTACACCTACTATCCAAACAGTGTGAAGGGGCGATTCA
CCATCTCCAGAGACAATGCCAAGAACACCCTGTACCTGCAAATGAGCCGTCTGAAGTCTGAGGACACAGCCAT
GTATTACTGTGCAAGACGGAGTGAACTGGGACTGTTTGCTTACTGGGGCCAAGGGACTCTGGTCACTGTCTCTG
CGtaa

Amino acid sequence (SEQ ID NO:16)
MDIVMTQSPALMSASPGEKVTMTCSASSSVSYMYWYQQKPRSSPKPWIYLTSNLASGVPARFSGSGSGTSYSLTISS
MEAEDAATYYCQQWSSNPYTFGGGTKLEIKRGGGGSGGGGSGGGGSGGGGSDVMVVESGGGLVKPGGSLKLSCA
ASGFTFSSYAMSWVRQTPEKRLEWVATISSGGSYTYYPNSVKGRFTISRDNAKNTLYLQMSRLKSEDTAMYYCARR
SELGLFAYWGQGTLVTVSA-

FIG. 1H

DNA sequence (SEQ ID NO:17)
atgGACTACAAAGATATTCAGATAAACCAGTCTCCATCTTCCATGTATGCATCTCTAGGAGAGAGAGTCACTATC
ACTTGCAAGGCGAGTCAGGACATTAATAGCTATTTAAGCTGGTTCCAGCAGAAACCAGGGAAATCTCCTAAGA
CCCTGATCTATCGTGCAAACAGATTGGTAGATGGGGTCCCATCAAGGTTCAGTGGCAGTGGATCTGGGCAAGA
TTATTCTCTCACCATCAGCAGCCTGGAGTATGAAGATATGGGAATTTATTATTGTCTACAGTATGATGAGTTTC
CTCTCACGTTCGGTGCTGGGACCAAGCTGGAAATCAAACGTGGTGGTGGTGGTTCTGGTGGTGGTGGTTCTGGC
GGCGGCGGCTCCGGTGGTGGTGGATCCGATGTACAGCTTCAGGAGTCTGGAGGAGGCTTGGTACAGCCTGGGG
GTTCTCTGAGACTCTCCTGTGCAACTTCTGGGTTCACCTTCACTGATTACTACATGAGCTGGGTCCGCCAGCCTC
CAGGAAAGGCACTTGAGTGGTTGGGTTTTATTAGAAACAAAGCTAATGGTTACACAACAGAGTACAGTGCATC
TGTGAAGGGTCGGTTCACCATCTCCAGAGATAATTCCCAAAGCATCCTCTATCTTCAAATGAACACCCTGAGAG
CTGAGGACAGTGCCACTTATTACTGTGCAAGAGATAAGGGATGGTTACACTTTGACTACTGGGGCCAAGGCAC
CACTCTCACAGTCTCCTCGtaa

Amino acid sequence (SEQ ID NO:18)
MDYKDIQINQSPSSMYASLGERVTITCKASQDINSYLSWFQQKPGKSPKTLIYRANRLVDGVPSRFSGSGSGQDYSLT
ISSLEYEDMGIYYCLQYDEFPLTFGAGTKLEIKRGGGGSGGGGSGGGGSGGGGSDVQLQESGGGLVQPGGSLRLSC
ATSGFTFTDYYMSWVRQPPGKALEWLGFIRNKANGYTTEYSASVKGRFTISRDNSQSILYLQMNTLRAEDSATYYC
ARDKGWLHFDYWGQGTTLTVSS-

FIG. 1I

DNA sequence (SEQ ID NO:19)
atgGACTACAAAGATATTCAGATGACACAGTCTCCATCCTCCTTATCTGCCTCTCTGGGAGAAAGAGTCAGTCTC
ACTTGTCGGGCAAGTCAGGACATTGGTAGTAGCTTAAACTGGCTTCAGCAGGAACCAGATGGAACTATTAAAC
GCCTGATCTACGCCACATCCAGTTTAGATTCTGGTGTCCCCAAAAGGTTCAGTGGCAGTAGGTCTGGGTCAGAT
TATTCTCTCACCATCAGCAGCCTTGAGTCTGAAGATTTTGTAGACTATTACTGTCTACAATATGCTAGTTCTCCG
TACACGTTCGGAGGGGGGACCAAGCTGGAAATAAAACGTGGTGGTGGTGGTTCTGGTGGTGGTGGTTCTGGCG
GCGGCGGCTCCTGTGGTGGTGGATCCCAGGTTCAACTGCAGCAGCCTGGGGCAGAGCTTGTGAGGTCAGGGGC
CTCAGTCAAGTTGTCCTGCACAGCTTCTGGCTTCAACATTAAAGACACCTATATGCACTGGGTGAAGCAGAGGC
CTGAACAGGGCCTGGAGTGGATTGGAAGGATTGATCCTGCGAATGGTAATACTAAATATGACCCGAAGTTCCA
GGGCAAGGCCACTATAACAGCAGACACATCCTCCAACACAGCCTACCTGCAGCTCAGCAGCCTGACATCTGAG
GACACTGCCGTCTATTACTGTGCTAGAAATTACCTCTTTGACTACTGGGGCCAAGGCACCACTCTCACAGTCTT
CCTCGtaa

Amino acid sequence (SEQ ID NO:20)
MDYKDIQMTQSPSSLSASLGERVSLTCRASQDIGSSLNWLQQEPDGTIKRLIYATSSLDSGVPKRFSGSRSGSDYSLTI
SSLESEDFVDYYCLQYASSPYTFGGGTKLEIKRGGGGSGGGGSGGGGSCGGGSQVQLQQPGAELVRSGASVKLSCT
ASGFNIKDTYMHWVKQRPEQGLEWIGRIDPANGNTKYDPKFQGKATITADTSSNTAYLQLSSLTSEDTAVYYCARN
YLFDYWGQGTTLTVFL-

FIG. 1J

DNA sequence (SEQ ID NO:21)
atgGACTACAAAGACATCCAGATGACACAGACTCCAGCAATCATGTCTGCATCTCTAGGGGAACGGGTCACCAT
GACCTGCACTGCCAGCTCAAGTGTAAGTTCCAGTTACTTGCACTGGTACCAGCAGAAGCCAGGATCCTCCCCCA
AACTCTGGATTTATAGCACATCCAACCTGGCTTCTGGAGTCCCAGCTCGCTTCAGTGGCAGTAGGTCTGGGACC
TCTTACTCTCTCACAATCAGCAGCATGGAGGCTGAAGATGCTGCCACTTATTACTGCCACCAGTATCATCGTTC
CCCCGTGGACGTTCGGTGGAGGCACCAAGCTGGAGCTGAAACGTGGTGGTGGTGGTTCTGGTGGTGGTGGTTCT
GGCGGCGGCGGCTCCGGTGGTGGTGGATCCGAGGTCCAACTGCAACAATCTGGGGCTGAACTGGCAAAACCTG
GGGCCTCAGTGAAGATGTCCTGCAAGGCTTCTGGCTACACCTTTACTAGCTACTGGATGCACTGGGTAAAACA
GAGGCCTGGACAGGGTCTGGAATGGATTGGATACATTAATCCTAGCACTGGTTATACTGAGTACAATCAGAAG
TTCAAGGACAAGGCCACATTGACTGCAGACAAATCCTCCAGCACAGCCTACATGCAACTGAGCAGCCTGACAT
CTGAGGACTCTGCAGTCTATTACTGTGCAAGTAGTAGCTTTGCTTACTGGGGCCAAGGGACTCTGGTCACTGTC
TCTGCGtaa

Amino acid sequence (SEQ ID NO:22)
MDYKDIQMTQTPAIMSASLGERVTMTCTASSSVSSSYLHWYQQKPGSSPKLWIYSTSNLASGVPARFSGSRSGTSYS
LTISSMEAEDAATYYCHQYHRSPWTFGGGTKLELKRGGGGSGGGGSGGGGSGGGGSEVQLQQSGAELAKPGASV
KMSCKASGYTFTSYWMHWVKQRPGQGLEWIGYINPSTGYTEYNQKFKDKATLTADKSSSTAYMQLSSLTSEDSAV
YYCASSSFAYWGQGTLVTVSA-

FIG. 1K

DNA sequence (SEQ ID NO:23)
atgGACTACAAAGACATTGAGCTGACCCAATCTCCAGCTTCTTTGGCTGTGTCTCTAGGGCAGAGGGCCACCATC
TCCTGCAGAGCCAGCGAAAGTGTTGATAATTATGGCATTAGTTTTATGAACTGGTTCCAACAGAAACCAGGAC
AGCCACCCAAACTCCTCATCTATGCTGCATCCAACCAAGGATCCGGGGTCCCTGCCAGGTTTAGTGGCAGTGG
GTCTGGGACAGACTTCAGCCTCAACATCCATCCTATGGAGGAGGATGATACTGCAATGTATTTCTGTCAGCAAA
GTAAGGAGGTTCCGTGGACGTTCGGTGGAGGCACCAAGCTGGAAATAAAACGTGGTGGTGGTGGTTCTGGTGG
TGGTGGTTCTGGCGGCGGCGGCTCCGGTGGTGGTGGATCCGAGGTCCAGCTGCAACAGTCAGGACCTGGCCTG
GTGGCGCCCTCACAGAGCCTGTCCATCACATGCACTGTCTCAGGGTTCTCATTAACCGACTATGGTGTAAGCTG
GATTCGCCAGCCTCCAGGAAAGGGTCTGGAGTGGCTGGGAGTAATATGGGGTGGTGGAAGCACATACTATAAT
TCAGCTCTCAAATCCAGACTGAGCATCAGCAAGGACAACTCCAAGAGCCAAGTTCTCTTAAAAATGAACAGTC
TGCAAACTGATGACACAGCCATGTACTACTGTGCCAAACATGGGGCTGGTTACTACTTTGACTACTGGGGCCA
AGGCACCACTCTCACAGTCTCCTCGtaa

Amino acid sequence (SEQ ID NO:24)
MDYKDIELTQSPASLAVSLGQRATISCRASESVDNYGISFMNWFQQKPGQPPKLLIYAASNQGSGVPARFSGSGSGT
DFSLNIHPMEEDDTAMYFCQQSKEVPWTFGGGTKLEIKRGGGGSGGGGSGGGGSGGGGSEVQLQQSGPGLVAPSQ
SLSITCTVSGFSLTDYGVSWIRQPPGKGLEWLGVIWGGGSTYYNSALKSRLSISKDNSKSQVLLKMNSLQTDDTAM
YYCAKHGAGYYFDYWGQGTTLTVSS-

FIG. 1L

DNA sequence (SEQ ID NO:25)
atgGACTACAAAGATATTGTGCTCACCCAATCTCCAGCAATCATGTCTGCATCTCCAGGGGAGAAGGTCACCATG
ACCTGCAGTGCCAGCTCAAGTGTAAGTTACATGCACTGGTACCAGCAGAAGTCAGGCACCTCCCCCAAAAGAT
GGATTTATGACACATCCAAACTGGCTTCTGGAGTCCCTGCTCGCTTCAGTGGCAGTGGGTCTGGGACCTCTTAC
CCTCTCACAATCAGCAGCATGGAGGCTGAAGATGCTGCCACTTATTACTGCCAGCAGTGGAGTAGTAACCCAC
TCACGTTCGGTGCTGGGACCAAACTGACTGTCCTAGGTGGTGGTGGTGGTTCTGGTGGTGGTGGTTCCGGCGGC
GGCGGCTCCGGTGGTGGTGGATCCGAGGTCCAGCTCCAGCAGTCCGGGGCTGAACTGGTGAAGCCTGGGGCTT
CAGTGAAGTTGTCCTGCAAGGCTTCTGGCTACACCTTCACCAGCTACTATATGTACTGGGTGAAGCAGAGGCCT
GGACAAGGCCTTGAGTGGATTGGAGAGATTTTACCTGGAAGTGGTAGTACTAACTTCAATGAGAAGTTCAAGA
GCAAGGCCACACTGACTGTAGACAAATCCTCCAGCACAGCCTACATGCAACTCAGCAGCCTGACATCTGAGGA
CTCTGCGGTCTATTACTGTACAAGAGGGCATTACTACGGCTGCTTTGACTACTGGGGCCAAGGCACCACTCTCA
CAGTCTCCTCGtaa

Amino acid sequence (SEQ ID NO:26)
MDYKDIVLTQSPAIMSASPGEKVTMTCSASSSVSYMHWYQQKSGTSPKRWIYDTSKLASGVPARFSGSGSGTSYPL
TISSMEAEDAATYYCQQWSSNPLTFGAGTKLTVLGGGGSGGGGSGGGGSGGGGSEVQLQQSGAELVKPGASVKL
SCKASGYTFTSYYMYWVKQRPGQGLEWIGEILPGSGSTNFNEKFKSKATLTVDKSSSTAYMQLSSLTSEDSAVYYC
TRGHYYGCFDYWGQGTTLTVSS-

FIG. 1M

Amino acid sequence (SEQ ID NO:40)
MKSCLLLFLIFSFLLSFSLAEQCGRQAGGALCPNGLCCSEFGWCGDTEAYCKQPGCQSQCGGTPPGPTGDLSGIISRSQFDDM
LKHRNDNACPARGFYTYDAFINAAKSFPGFGTTGDTATRKKEIAAFFGQTSHETTGGWATAPDGPYSWGYCFKQEQNPSSNYC
SPSAEWPCASGKSYYGRGPMQLSWNYNYGQCGRAIGSDLLNNPDLVSNDPVIAFKAAIWFWMTPQSPKPSCHAVIVGQWQPSD
ADRAAGRVPGYGVITNIINGGLECGRGQDARVADRIGFYQRYCNILGVNPGGNLDCYNQRSFASVNFFLDAAIGGGGSGGGGS
DIVLSQSPTIMSASPGEKVTMTCSASSSVSYMHWYQQKSGTSPKRWIYDTSKLASGVPARFSGSGSGTPYPLTISSMEAEDAA
TYYCLQWSSNPWTFGGGTKLELKRGGGGSGGGGSGGGGSGGGGSQVQLKQSGAELAKPGASVKMSCKASGYTFTSYWMHWVKQ
RPGQGLEWIGYINPSTGYTEYNQKFKDKATLTADKSSSTAYMQLSSLTSEDSAVYYCARKFYGNFPMDYWGQGTSVTVSSLEH
HHHHH-

FIG. 2

DNA sequence (SEQ ID NO:27)
atgGACATTGTGTTGACACAGTCTCCAGCAATCATGTCTGCATCTCCAGGGGAAAAGGTCACCATGACCTGCAGT
GCCAGCTCAAGTGTAAGTTACATGCACTGGTACCAGCAGAAGTCAAGCACCTCCCCCAAACTCTGGATTTATG
ACACATCCAAACTGGCTTCTGGAGTCCCAGGTCGCTTCAGTGGCAGTGGGTCTGGAAACTCTTACTCTCTCACG
ATCAGCAGCATGGAGGCTGAAGATGTTGCCACTTATTACTGTTTTCAGGGGAGTGGGTACCCGCTCACGTTCGG
TGCTGGGACCAAGCTGGAAATCAAACGTGGTGCTGGTGGTTCTGGTGGTGGTGGTTCTGGCGGCGGCGGCTCC
GGTGGTGGTGGATCCCAGGTCCAGCTTCAGCAATCTGGGGCTGAGCTGGTGAGGCCTGGGTCCTCAGTGAAGA
TTTCCTGCAAGGCTTCTGGCTATGCATTCAGTAACTACTGGATGAACTGGGTGAAGCAGAGGCCTGGACAGGG
TCTTGAGTGGATTGGACAGATTTATCCTGGATATGGTGATGCTAAATACAATGGAAAGTTCAAGGGTAAGGCC
ACGCTGACTGCAGACATATCCTCCAGCACAGCCTATATGCAGCTCAGCAGCCTAACATCTGAGGACTCTGCAG
TCTATTTCTGTGCAAGATCATCTTACGAGGCTAACTGGGGCCAAGGGACTCTGGTCACTGTCTCTGCGctcgagcacc
accaccaccaccactga

Amino acid sequence (SEQ ID NO:28)
MDIVLTQSPAIMSASPGEKVTMTCSASSSVSYMHWYQQKSSTSPKLWIYDTSKLASGVPGRFSGSGSGNSYSLTISS
MEAEDVATYYCFQGSGYPLTFGAGTKLEIKRGAGGSGGGGSGGGGSGGGGSQVQLQQSGAELVRPGSSVKISCKA
SGYAFSNYWMNWVKQRPGQGLEWIGQIYPGYGDAKYNGKFKGKATLTADISSSTAYMQLSSLTSEDSAVYFCARS
SYEANWGQGTLVTVSALEHHHHHH-

FIG. 2A

DNA sequence (SEQ ID NO:29)
atgGATATTGTGATGACCCAGTCTCACAAATTCATGTCCACATCAGTAGGAGACAGGGTCAGCATCACCTGCAA
GGCCAGTCAGGATGTGGGTACTGCTGTAGCCTGGTATCAACAGAAACCAGGGCAATCTCCTAAACTACTGATT
TACTGGGCATCCACCCGGCACACTGGAGTCCCTGATCGCTTCACAGGCAGTGGATCTGGGACAGATTTCACTCT
CACCATTAGCAATGTGCAGTCTGAAGACTTGGCAGATTATTTCTGTCAGCAATATAGCAGCTATCCTCGGACGT
TCGGTGGAGGCACCAAGCTGGAAATCAAACGTGGTGGTGGTGGTTCTGGTGGTGGTGGTTCTGGCGGCGGCGG
CTCCGGTGGTGGTGGATCCGAGGTGCAGCTTCAGCAGTCTGGGGCAGACCTTGTGAGGTCAGGGGCCTCAGTC
AAGTTGTCCTGCACAGCTTCTGGCTTCAACATTAAAGACTACTATATCCACTGGGTGAAGCAGAGGCCTGAAC
AGGGCCTGGCGTGGATTGGATGGATTGATCCTGAGAATGGTGATACTGAATATGCCCCGAAGTTCCAGGACAA
GGCCACTTTGACTGCAGACACATCTTCCAATACAGCCTACCTGCAGCTCAGCAGCCTGACATCTGAGGACACTG
CCGTCTATTACTGTAATGCATGGGCTGGGACGTCAGGGGCCTGGTTTGCTTACTGGGGCCAAGGGACTCTGGTC
ACTGTCTCTGCGctcgagcaccaccaccaccaccactga

Amino acid sequence (SEQ ID NO:30)
MDIVMTQSHKFMSTSVGDRVSITCKASQDVGTAVAWYQQKPGQSPKLLIYWASTRHTGVPDRFTGSGSGTDFTLTI
SNVQSEDLADYFCQQYSSYPRTFGGGTKLEIKRGGGGSGGGGSGGGGSGGGGSEVQLQQSGADLVRSGASVKLSC
TASGFNIKDYYIHWVKQRPEQGLAWIGWIDPENGDTEYAPKFQDKATLTADTSSNTAYLQLSSLTSEDTAVYYCNA
WAGTSGAWFAYWGQGTLVTVSALEHHHHHH-

FIG. 2B

DNA sequence (SEQ ID NO:31)
atgGATATTGTTCTCTCCCAGTCTCCAACAATCATGTCTGCATCTCCAGGGGAGAAGGTCACCATGACCTGCAGT
GCCAGCTCAAGTGTAAGTTACATGCACTGGTACCAGCAGAAGTCAGGCACCTCCCCCAAAAGATGGATTTATG
ACACATCCAAACTGGCTTCTGGAGTCCCTGCTCGCTTCAGTGGCAGTGGGTCTGGGACCCCTTACCCTCTCACA
ATCAGCAGCATGGAGGCTGAAGATGCTGCCACTTATTACTGCCTGCAGTGGAGTAGTAACCCGTGGACGTTCG
GTGGAGGCACCAAGCTGGAGCTGAAACGTGGTGGTGGTGGTTCTGGTGGTGGTGGTTCTGGCGGCGGCGGCTC
CGGTGGTGGTGGATCCCAGGTGCAGCTGAAGCAATCTGGGGCTGAACTGGCAAAACCTGGGGCCTCAGTGAAG
ATGTCCTGCAAGGCTTCTGGCTACACCTTTACTAGCTACTGGATGCACTGGGTAAAACAGAGGCCTGGACAGG
GTCTGGAATGGATTGGATACATTAATCCTAGCACTGGTTATACTGAGTACAATCAGAAGTTCAAGGACAAGGC
CACATTGACTGCAGACAAATCCTCCAGCACAGCCTACATGCAACTGAGCAGCCTGACATCTGAGGACTCTGCA
GTCTATTACTGTGCAAGAAAGTTCTATGGTAACTTCCCTATGGACTACTGGGGTCAAGGAACCTCAGTCACCGT
CTCCTCGctcgagcaccaccaccaccaccactga

Amino acid sequence (SEQ ID NO:32)
MDIVLSQSPTIMSASPGEKVTMTCSASSSVSYMHWYQQKSGTSPKRWIYDTSKLASGVPARFSGSGSGT
PYPLTISSMEAEDAATYYCLQWSSNPWTFGGGTKLELKRGGGGSGGGGSGGGGSGGGGSQVQLKQSG
AELAKPGASVKMSCKASGYTFTSYWMHWVKQRPGQGLEWIGYINPSTGYTEYNQKFKDKATLTADKS
SSTAYMQLSSLTSEDSAVYYCARKFYGNFPMDYWGQGTSVTVSSLEHHHHHH-

FIG. 2C

DNA sequence (SEQ ID NO:33)
atgGATATTGTTCTCTCCCAGTCTCCAACAATCATGTCTGCATCTCCAGGGGAGAAGGTCACCATGACCTGCAGT
GCCAGCTCAAGTGTAAGTTACATGCACTGGTACCAGCAGAAGTCAGGCACCTCCCCCAAAAGATGGATTTATG
ACACATCCAAACTGGCTTCTGGAGTCCCTGCTCGCTTCAGTGGCAGTGGGTCTGGGACCCCTTACCCTCTCACA
ATCAGCAGCATGGAGGCTGAAGATGCTGCCACTTATTACTGCCTGCAGTGGAGTAGTAACCCGTGGACGTTCG
GTGGAGGCACCAAGCTGGAGCTGAAACGTGGTGGTGGTGGTTCTGGTGGTGGTGGTTCTGGCGGCGGCGGCTC
CGGTGGTGGTGGATCCCAGGTGCAGCTGAAGCAATCTGGGGCTGAACTGGCAAAACCTGGGGCCTCAGTGAAG
ATGTCCTGCAAGGCTTCTGGCTACACCTTTACTAGCTACTGGATGCACTGGGTAAAACAGAGGCCTGGACAGG
GTCTGGAATGGATTGGATACATTAATCCTAGCACTGGTTATACTGAGTACAATCAGAAGTTCAAGGACAAGGC
CACATTGACTGCAGACAAATCCTCCAGCACAGCCTACATGCAACTGAGCAGCCTGACATCTGAGGACTCTGCA
GTCTATTACTGTGCAAGAAAGTTCTATGGTAACTTCCCTATGGACTACTGGGGTCAAGGAACCTCAGTCACCGT
CTCCTCGGGAGGAGGAGGATCAGGAGGAGGAGGATCA<u>CATATG</u>GATATTGTTCTCTCCCAGTCTCCAACAATC
ATGTCTGCATCTCCAGGGGAGAAGGTCACCATGACCTGCAGTGCCAGCTCAAGTGTAAGTTACATGCACTGGT
ACCAGCAGAAGTCAGGCACCTCCCCCAAAAGATGGATTTATGACACATCCAAACTGGCTTCTGGAGTCCCTGC
TCGCTTCAGTGGCAGTGGGTCTGGGACCCCTTACCCTCTCACAATCAGCAGCATGGAGGCTGAAGATGCTGCC
ACTTATTACTGCCTGCAGTGGAGTAGTAACCCGTGGACGTTCGGTGGAGGCACCAAGCTGGAGCTGAAACGTG
GTGGTGGTGGTTCTGGTGGTGGTGGTTCTGGCGGCGGCGGCTCCGGTGGTGGTGGATCCCAGGTGCAGCTGAA
GCAATCTGGGGCTGAACTGGCAAAACCTGGGGCCTCAGTGAAGATGTCCTGCAAGGCTTCTGGCTACACCTTT
ACTAGCTACTGGATGCACTGGGTAAAACAGAGGCCTGGACAGGGTCTGGAATGGATTGGATACATTAATCCTA
GCACTGGTTATACTGAGTACAATCAGAAGTTCAAGGACAAGGCCACATTGACTGCAGACAAATCCTCCAGCAC
AGCCTACATGCAACTGAGCAGCCTGACATCTGAGGACTCTGCAGTCTATTACTGTGCAAGAAAGTTCTATGGTA
ACTTCCCTATGGACTACTGGGGTCAAGGAACCTCAGTCACCGTCTCCTCGctcgagcaccaccaccaccaccactga

Amino acid sequence (SEQ ID NO:34)
MDIVLSQSPTIMSASPGEKVTMTCSASSSVSYMHWYQQKSGTSPKRWIYDTSKLASGVPARFSGSGSGTPYPLTI
SSMEAEDAATYYCLQWSSNPWTFGGGTKLELKRGGGGSGGGGSGGGGSGGGGSQVQLKQSGAELAKPGASVKMSC
KASGYTFTSYWMHWVKQRPGQGLEWIGYINPSTGYTEYNQKFKDKATLTADKSSSTAYMQLSSLTSEDSAVYYCA
RKFYGNFPMDYWGQGTSVTVSSGGGGSGGGGSHMDIVLSQSPTIMSASPGEKVTMTCSASSSVSYMHWYQQKSGT
SPKRWIYDTSKLASGVPARFSGSGSGTPYPLTISSMEAEDAATYYCLQWSSNPWTFGGGTKLELKRGGGGSGGGG
SGGGGSGGGGSQVQLKQSGAELAKPGASVKMSCKASGYTFTSYWMHWVKQRPGQGLEWIGYINPSTGYTEYNQKF
KDKATLTADKSSSTAYMQLSSLTSEDSAVYYCARKFYGNFPMDYWGQGTSVTVSSLEHHHHHH-

FIG. 2D

DNA sequence (SEQ ID NO:35)
atgCAGAAGTTGTGCGAAAGGCCAAGTGGGACATGGTCAGGAGTCTGTGGAAACAATAACGCATGCAAGAATC
AGTGCATTAACCTTGAGAAAGCACGACATGGATCTTGCAACTATGTCTTCCCAGCTCACAAGTGTATCTGCTAC
TTTCCTTGTGGTGGTGGTGGTTCTGGCGGCGGCGGCTCCGATATTGTTCTCTCCCAGTCTCCAACAATCATGTCT
GCATCTCCAGGGGAGAAGGTCACCATGACCTGCAGTGCCAGCTCAAGTGTAAGTTACATGCACTGGTACCAGC
AGAAGTCAGGCACCTCCCCCAAAAGATGGATTTATGACACATCCAAACTGGCTTCTGGAGTCCCTGCTCGCTTC
AGTGGCAGTGGGTCTGGGACCCCTTACCCTCTCACAATCAGCAGCATGGAGGCTGAAGATGCTGCCACTTATT
ACTGCCTGCAGTGGAGTAGTAACCCGTGGACGTTCGGTGGAGGCACCAAGCTGGAGCTGAAACGTGGTGGTGG
TGGTTCTGGTGGTGGTGGTTCTGGCGGCGGCGGCTCCGGTGGTGGTGGATCCCAGGTGCAGCTGAAGCAATCT
GGGGCTGAACTGGCAAAACCTGGGGCCTCAGTGAAGATGTCCTGCAAGGCTTCTGGCTACACCTTTACTAGCT
ACTGGATGCACTGGGTAAAACAGAGGCCTGGACAGGGTCTGGAATGGATTGGATACATTAATCCTAGCACTGG
TTATACTGAGTACAATCAGAAGTTCAAGGACAAGGCCACATTGACTGCAGACAAATCCTCCAGCACAGCCTAC
ATGCAACTGAGCAGCCTGACATCTGAGGACTCTGCAGTCTATTACTGTGCAAGAAAGTTCTATGGTAACTTCCC
TATGGACTACTGGGGTCAAGGAACCTCAGTCACCGTCTCCTCGctcgagcaccaccaccaccaccactga

Amino acid sequence (SEQ ID NO:36)
MQKLCERPSGTWSGVCGNNNACKNQCINLEKARHGSCNYVFPAHKCICYFPCGGGGSGGGGSDIVLSQSPTIMSAS
PGEKVTMTCSASSSVSYMHWYQQKSGTSPKRWIYDTSKLASGVPARFSGSGSGTPYPLTISSMEAEDAATYYCLQW
SSNPWTFGGGTKLELKRGGGGSGGGGSGGGGSGGGGSQVQLKQSGAELAKPGASVKMSCKASGYTFTSYWMHW
VKQRPGQGLEWIGYINPSTGYTEYNQKFKDKATLTADKSSSTAYMQLSSLTSEDSAVYYCARKFYGNFPMDYWGQ
GTSVTVSSLEHHHHHH-

FIG. 2E

DNA sequence (SEQ ID NO:37)
atgGCTAAGTTTGCGTCCATCATCGCACTTCTTTTTTGCTGCTCTTGTTCTTTTTGCTGCTTTCGAAGCACCAACAAT
GGTGGAAGCACAGAAGTTGTGCGAAAGGCCAAGTGGGACATGGTCAGGAGTCTGTGGAAACAATAACGCATG
CAAGAATCAGTGCATTAACCTTGAGAAAGCACGACATGGATCTTGCAACTATGTCTTCCCAGCTCACAAGTGT
ATCTGCTACTTTCCTTGTGGTGGTGGTGGTTCTGGCGGCGGCGGCTCCGATATTGTTCTCTCCCAGTCTCCAACA
ATCATGTCTGCATCTCCAGGGGAGAAGGTCACCATGACCTGCAGTGCCAGCTCAAGTGTAAGTTACATGCACT
GGTACCAGCAGAAGTCAGGCACCTCCCCCAAAAGATGGATTTATGACACATCCAAACTGGCTTCTGGAGTCCC
TGCTCGCTTCAGTGGCAGTGGGTCTGGGACCCCTTACCCTCTCACAATCAGCAGCATGGAGGCTGAAGATGCTG
CCACTTATTACTGCCTGCAGTGGAGTAGTAACCCGTGGACGTTCGGTGGAGGCACCAAGCTGGAGCTGAAACG
TGGTGGTGGTGGTTCTGGTGGTGGTGGTTCTGGCGGCGGCGGCTCCGGTGGTGGTGGATCCCAGGTGCAGCTG
AAGCAATCTGGGGCTGAACTGGCAAAACCTGGGGCCTCAGTGAAGATGTCCTGCAAGGCTTCTGGCTACACCT
TTACTAGCTACTGGATGCACTGGGTAAAACAGAGGCCTGGACAGGGTCTGGAATGGATTGGATACATTAATCC
TAGCACTGGTTATACTGAGTACAATCAGAAGTTCAAGGACAAGGCCACATTGACTGCAGACAAATCCTCCAGC
ACAGCCTACATGCAACTGAGCAGCCTGACATCTGAGGACTCTGCAGTCTATTACTGTGCAAGAAAGTTCTATG
GTAACTTCCCTATGGACTACTGGGGTCAAGGAACCTCAGTCACCGTCTCCTCGctcgagcaccaccaccaccaccactga

Amino acid sequence (SEQ ID NO:38)
MAKFASIIALLFAALVLFAAFEAPTMVEAQKLCERPSGTWSGVCGNNNACKNQCINLEKARHGSCNYVFPAHKCIC
YFPCGGGGSGGGGSDIVLSQSPTIMSASPGEKVTMTCSASSSVSYMHWYQQKSGTSPKRWIYDTSKLASGVPARFS
GSGSGTPYPLTISSMEAEDAATYYCLQWSSNPWTFGGGTKLELKRGGGGSGGGGSGGGGSGGGGSQVQLKQSGAE
LAKPGASVKMSCKASGYTFTSYWMHWVKQRPGQGLEWIGYINPSTGYTEYNQKFKDKATLTADKSSSTAYMQLS
SLTSEDSAVYYCARKFYGNFPMDYWGQGTSVTVSSLEHHHHHH-

FIG. 2F

DNA sequence (SEQ ID NO:39)
atgAAGTCTTGTCTACTTCTCTTTCTCATTTCTTTTATCATTTTCCTTAGCCGAGCAATGTGGTCGACA
AGCGGGAGGAGCTCTCTGCCCCAACGGTCTATGCTGCAGCGAGTTCGGATGGTGCGGTGACACCGAAGCTTAC
TGTAAGCAGCCTGGCTGCCAAAGCCAGTGCGGTGGTACTCCTCCTGGCCCCACCGGTGATCTTTCAGGCATCAT
TTCAAGATCTCAGTTCGACGACATGCTTAAACATAGAAATGATAATGCTTGTCCCGCTAGAGGTTTCTACACTT
ATGATGCCTTTATCAATGCCGCTAAGTCTTTCCCTGGCTTCGGCACCACCGGAGACACTGCCACAAGGAAGAA
AGAAATCGCTGCCTTCTTTGGTCAGACTTCCCACGAGACCACCGGTGGGTGGGCCACAGCACCAGACGGACCA
TATTCATGGGGATACTGTTTCAAACAAGAGCAGAACCCTTCTTCAAACTACTGTTCACCGAGTGCCGAATGGCC
ATGCGCATCTGGTAAAAGCTACTACGGAAGAGGACCAATGCAGCTATCATGGAACTACAACTACGGACAGTGT
GGAAGAGCCATCGGATCTGACTTACTCAACAACCCTGACCTTGTCTCCAACGATCCAGTGATCGCTTTCAAAGC
CGCGATTTGGTTTTGGATGACACCTCAGTCTCCAAAACCGTCGTGCCACGCCGTGATCGTCGGCCAGTGGCAGC
CTTCGGATGCTGACCGTGCCGCTGGGAGAGTACCGGGTTACGGTGTGATTACGAATATTATTAACGGTGGTTTA
GAGTGTGGACGCGGCCAAGACGCTAGAGTCGCGGATAGAATTGGATTTTACCAGAGGTACTGTAACATTCTTG
GAGTTAATCCTGGAGGTAACCTTGATTGTTACAACCAAAGGTCCTTTGCTTCTGTTAACTTCTTCCTTGACGCTG
CTATTGGTGGTGGTGGTTCTGGCGGCGGCGGCTCCGATATTGTTCTCTCCCAGTCTCCAACAATCATGTCTGCAT
CTCCAGGGGAGAAGGTCACCATGACCTGCAGTGCCAGCTCAAGTGTAAGTTACATGCACTGGTACCAGCAGAA
GTCAGGCACCTCCCCCAAAAGATGGATTTATGACACATCCAAACTGGCTTCTGGAGTCCCTGCTCGCTTCAGTG
GCAGTGGGTCTGGGACCCCTTACCCTCTCACAATCAGCAGCATGGAGGCTGAAGATGCTGCCACTTATTACTGC
CTGCAGTGGAGTAGTAACCCGTGGACGTTCGGTGGAGGCACCAAGCTGGAGCTGAAACGTGGTGGTGGTGGTT
CTGGTGGTGGTGGTTCTGGCGGCGGCGGCTCCGGTGGTGGTGGATCCCAGGTGCAGCTGAAGCAATCTGGGGC
TGAACTGGCAAAACCTGGGGCCTCAGTGAAGATGTCCTGCAAGGCTTCTGGCTACACCTTTACTAGCTACTGGA
TGCACTGGGTAAAACAGAGGCCTGGACAGGGTCTGGAATGGATTGGATACATTAATCCTAGCACTGGTTATAC
TGAGTACAATCAGAAGTTCAAGGACAAGGCCACATTGACTGCAGACAAATCCTCCAGCACAGCCTACATGCAA
CTGAGCAGCCTGACATCTGAGGACTCTGCAGTCTATTACTGTGCAAGAAAGTTCTATGGTAACTTCCCTATGGA
CTACTGGGGTCAAGGAACCTCAGTCACCGTCTCCTCGctcgagcaccaccaccaccaccactga

Amino acid sequence (SEQ ID NO:40)
MKSCLLLFLIFSPLLSFSLAEQCGRQAGGALCPNGLCCSEFGWCGDTEAYCKQPGCQSQCGGTPPGPTGDLSGIISRSQFDDM
LKHRNDNACPARGFYTYDAFINAAKSFPGFGTTGDTATRKKEIAAFFGQTSHETTGGWATAPDGPYSWGYCFKQEQNPSSNYC
SPSAEWPCASGKSYYGRGPMQLSWNYNYGQCGRAIGSDLLNNPDLVSNDPVIAFKAAIWFWMTPQSPKPSCHAVIVGQWQPSD
ADRAAGRVPGYGVITNIINGGLECGRGQDARVADRIGFYQRYCNILGVNPGGNLDCYNQRSFASVNFFLDAAIGGGGSGGGGS
DIVLSQSPTIMSASPGEKVTMTCSASSSVSYMHWYQQKSGTSPKRWIYDTSKLASGVPARFSGSGSGTPYPLTISSMEAEDAA
TYYCLQWSSNPWTFGGGTKLELKRGGGSGGGGSGGGGSQVQLKQSGAELAKPGASVKMSCKASGYTFTSYWMHWVKQ
RPGQGLEWIGYINPSTGYTEYNQKFKDKATLTADKSSSTAYMQLSSLTSEDSAVYYCARKFYGNFPMDYWGQGTSVTVSSLEH
HHHHH-

FIG. 2G

SEQUENCE LISTING

```
<160> NUMBER OF SEQ ID NOS: 90

<210> SEQ ID NO 1
<211> LENGTH: 732
<212> TYPE: DNA
<213> ORGANISM: Artificial
<220> FEATURE:
<223> OTHER INFORMATION: DNA sequence of scFv-SSPG1d-peptide

<400> SEQUENCE: 1
atggacattg tgttgacaca gtctccagca atcatgtctg catctccagg ggaaaaggtc      60
accatgacct gcagtgccag ctcaagtgta agttacatgc actggtacca gcagaagtca     120
```

```
agcacctccc ccaaactctg gatttatgac acatccaaac tggcttctgg agtcccaggt    180
cgcttcagtg gcagtgggtc tggaaactct tactctctca cgatcagcag catggaggct    240
gaagatgttg ccacttatta ctgttttcag gggagtgggt acccgctcac gttcggtgct    300
gggaccaagc tggaaatcaa acgtggtgct ggtggttctg gtggtggtgg ttctggcggc    360
ggcggctccg gtggtggtgg atcccaggtc cagcttcagc aatctggggc tgagctggtg    420
aggcctgggt cctcagtgaa gatttcctgc aaggcttctg gctatgcatt cagtaactac    480
tggatgaact gggtgaagca gaggcctgga cagggtcttg agtggattgg acagatttat    540
cctggatatg gtgatgctaa atacaatgga aagttcaagg gtaaggccac gctgactgca    600
gacatatcct ccagcacagc ctatatgcag ctcagcagcc taacatctga ggactctgca    660
gtctatttct gtgcaagatc atcttacgag gctaactggg gccaagggac tctggtcact    720
gtctctgcgt aa                                                       732
```

<210> SEQ ID NO 2
<211> LENGTH: 243
<212> TYPE: PRT
<213> ORGANISM: Artificial
<220> FEATURE:
<223> OTHER INFORMATION: Protein sequence of scFv-SSPG1d-peptide

<400> SEQUENCE: 2

```
Met Asp Ile Val Leu Thr Gln Ser Pro Ala Ile Met Ser Ala Ser Pro
1               5                   10                  15

Gly Glu Lys Val Thr Met Thr Cys Ser Ala Ser Ser Val Ser Tyr
            20                  25                  30

Met His Trp Tyr Gln Gln Lys Ser Ser Thr Pro Lys Leu Trp Ile
        35                  40                  45

Tyr Asp Thr Ser Lys Leu Ala Ser Gly Val Pro Gly Arg Phe Ser Gly
    50                  55                  60

Ser Gly Ser Gly Asn Ser Tyr Ser Leu Thr Ile Ser Ser Met Glu Ala
65                  70                  75                  80

Glu Asp Val Ala Thr Tyr Tyr Cys Phe Gln Gly Ser Gly Tyr Pro Leu
                85                  90                  95

Thr Phe Gly Ala Gly Thr Lys Leu Glu Ile Lys Arg Gly Ala Gly Gly
            100                 105                 110

Ser Gly Gly Gly Gly Ser Gly Gly Gly Ser Gly Gly Gly Gly Ser
            115                 120                 125

Gln Val Gln Leu Gln Gln Ser Gly Ala Glu Leu Val Arg Pro Gly Ser
        130                 135                 140

Ser Val Lys Ile Ser Cys Lys Ala Ser Gly Tyr Ala Phe Ser Asn Tyr
145                 150                 155                 160

Trp Met Asn Trp Val Lys Gln Arg Pro Gly Gln Gly Leu Glu Trp Ile
                165                 170                 175

Gly Gln Ile Tyr Pro Gly Tyr Gly Asp Ala Lys Tyr Asn Gly Lys Phe
            180                 185                 190

Lys Gly Lys Ala Thr Leu Thr Ala Asp Ile Ser Ser Ser Thr Ala Tyr
        195                 200                 205

Met Gln Leu Ser Ser Leu Thr Ser Glu Asp Ser Ala Val Tyr Phe Cys
    210                 215                 220

Ala Arg Ser Ser Tyr Glu Ala Asn Trp Gly Gln Gly Thr Leu Val Thr
225                 230                 235                 240

Val Ser Ala
```

<210> SEQ ID NO 3
<211> LENGTH: 750
<212> TYPE: DNA
<213> ORGANISM: Artificial
<220> FEATURE:
<223> OTHER INFORMATION: DNA sequence of scFv-SSPG1d-whole protein

<400> SEQUENCE: 3

```
atggatattg tgatgaccca gtctcacaaa ttcatgtcca catcagtagg agacagggtc      60
agcatcacct gcaaggccag tcaggatgtg ggtactgctg tagcctggta tcaacagaaa     120
ccagggcaat ctcctaaact actgatttac tgggcatcca cccggcacac tggagtccct     180
gatcgcttca caggcagtgg atctgggaca gatttcactc tcaccattag caatgtgcag     240
tctgaagact ggcagattat tttctgtcag caatatagca gctatcctcg gacgttcggt     300
ggaggcacca agctggaaat caaacgtggt ggtggtggtt ctggtggtgg tggttctggc     360
ggcggcggct ccggtggtgg tggatccgag gtgcagcttc agcagtctgg ggcagacctt     420
gtgaggtcag gggcctcagt caagttgtcc tgcacagctt ctggcttcaa cattaaagac     480
tactatatcc actgggtgaa gcagaggcct gaacagggcc tggcgtggat tggatggatt     540
gatcctgaga atggtgatac tgaatatgcc ccgaagttcc aggacaaggc cactttgact     600
gcagacacat cttccaatac agcctacctg cagctcagca gcctgacatc tgaggacact     660
gccgtctatt actgtaatgc atgggctggg acgtcagggg cctggtttgc ttactggggc     720
caagggactc tggtcactgt ctctgcgtaa                                      750
```

<210> SEQ ID NO 4
<211> LENGTH: 249
<212> TYPE: PRT
<213> ORGANISM: Artificial
<220> FEATURE:
<223> OTHER INFORMATION: Protein sequence of scFv-SSPG1d-whole protein

<400> SEQUENCE: 4

```
Met Asp Ile Val Met Thr Gln Ser His Lys Phe Met Ser Thr Ser Val
1               5                   10                  15

Gly Asp Arg Val Ser Ile Thr Cys Lys Ala Ser Gln Asp Val Gly Thr
            20                  25                  30

Ala Val Ala Trp Tyr Gln Gln Lys Pro Gly Gln Ser Pro Lys Leu Leu
        35                  40                  45

Ile Tyr Trp Ala Ser Thr Arg His Thr Gly Val Pro Asp Arg Phe Thr
    50                  55                  60

Gly Ser Gly Ser Gly Thr Asp Phe Thr Leu Thr Ile Ser Asn Val Gln
65                  70                  75                  80

Ser Glu Asp Leu Ala Asp Tyr Phe Cys Gln Gln Tyr Ser Ser Tyr Pro
                85                  90                  95

Arg Thr Phe Gly Gly Gly Thr Lys Leu Glu Ile Lys Arg Gly Gly Gly
            100                 105                 110

Gly Ser Gly Gly Gly Gly Ser Gly Gly Gly Ser Gly Gly Gly Gly
        115                 120                 125

Ser Glu Val Gln Leu Gln Gln Ser Gly Ala Asp Leu Val Arg Ser Gly
    130                 135                 140

Ala Ser Val Lys Leu Ser Cys Thr Ala Ser Gly Phe Asn Ile Lys Asp
145                 150                 155                 160

Tyr Tyr Ile His Trp Val Lys Gln Arg Pro Glu Gln Gly Leu Ala Trp
                165                 170                 175

Ile Gly Trp Ile Asp Pro Glu Asn Gly Asp Thr Glu Tyr Ala Pro Lys
            180                 185                 190
```

```
Phe Gln Asp Lys Ala Thr Leu Thr Ala Asp Thr Ser Ser Asn Thr Ala
        195                 200                 205

Tyr Leu Gln Leu Ser Ser Leu Thr Ser Glu Asp Thr Ala Val Tyr Tyr
        210                 215                 220

Cys Asn Ala Trp Ala Gly Thr Ser Gly Ala Trp Phe Ala Tyr Trp Gly
225                 230                 235                 240

Gln Gly Thr Leu Val Thr Val Ser Ala
                245

<210> SEQ ID NO 5
<211> LENGTH: 744
<212> TYPE: DNA
<213> ORGANISM: Artificial
<220> FEATURE:
<223> OTHER INFORMATION: DNA sequence of scFv-mycelia (monomer)

<400> SEQUENCE: 5
atggatattg ttctctccca gtctccaaca atcatgtctg catctccagg ggagaaggtc      60
accatgacct gcagtgccag ctcaagtgta agttacatgc actggtacca gcagaagtca     120
ggcacctccc ccaaaagatg gatttatgac acatccaaac tggcttctgg agtccctgct     180
cgcttcagtg gcagtgggtc tgggacccct taccctctca aatcagcag catggaggct      240 gaagatgctg ccacttatta ctgcctgcag tggagtagta cccgtggac gttcggtgga     300 ggcaccaagc tggagctgaa acgtggtggt ggtggttctg gtggtggtgg ttctggcggc     360
ggcggctccg gtggtggtgg atcccaggtg cagctgaagc aatctgggc tgaactggca    420 aaacctgggg cctcagtgaa gatgtcctgc aaggcttctg gctacacctt tactagctac     480
tggatgcact gggtaaaaca gaggcctgga cagggtctgg aatggattgg atacattaat     540
cctagcactg gttatactga gtacaatcag aagttcaagg acaaggccac attgactgca     600
gacaaatcct ccagcacagc ctacatgcaa ctgagcagcc tgacatctga ggactctgca     660
gtctattact gtgcaagaaa gttctatggt aacttcccta tggactactg gggtcaagga     720
acctcagtca ccgtctcctc gtaa                                            744

<210> SEQ ID NO 6
<211> LENGTH: 247
<212> TYPE: PRT
<213> ORGANISM: Artificial
<220> FEATURE:
<223> OTHER INFORMATION: Protein sequence of scFv-mycelia (monomer)

<400> SEQUENCE: 6

Met Asp Ile Val Leu Ser Gln Ser Pro Thr Ile Met Ser Ala Ser Pro
1               5                   10                  15

Gly Glu Lys Val Thr Met Thr Cys Ser Ala Ser Ser Val Ser Tyr
            20                  25                  30

Met His Trp Tyr Gln Gln Lys Ser Gly Thr Ser Pro Lys Arg Trp Ile
        35                  40                  45

Tyr Asp Thr Ser Lys Leu Ala Ser Gly Val Pro Ala Arg Phe Ser Gly
    50                  55                  60

Ser Gly Ser Gly Thr Pro Tyr Pro Leu Thr Ile Ser Ser Met Glu Ala
65                  70                  75                  80

Glu Asp Ala Ala Thr Tyr Tyr Cys Leu Gln Trp Ser Ser Asn Pro Trp
                85                  90                  95

Thr Phe Gly Gly Gly Thr Lys Leu Glu Leu Lys Arg Gly Gly Gly Gly
            100                 105                 110
```

```
Ser Gly Gly Gly Gly Ser Gly Gly Gly Ser Gly Gly Gly Gly Ser
            115                 120                 125

Gln Val Gln Leu Lys Gln Ser Gly Ala Glu Leu Ala Lys Pro Gly Ala
        130                 135                 140

Ser Val Lys Met Ser Cys Lys Ala Ser Gly Tyr Thr Phe Thr Ser Tyr
145                 150                 155                 160

Trp Met His Trp Val Lys Gln Arg Pro Gly Gln Gly Leu Glu Trp Ile
                165                 170                 175

Gly Tyr Ile Asn Pro Ser Thr Gly Tyr Thr Glu Tyr Asn Gln Lys Phe
            180                 185                 190

Lys Asp Lys Ala Thr Leu Thr Ala Asp Lys Ser Ser Ser Thr Ala Tyr
        195                 200                 205

Met Gln Leu Ser Ser Leu Thr Ser Glu Asp Ser Ala Val Tyr Tyr Cys
    210                 215                 220

Ala Arg Lys Phe Tyr Gly Asn Phe Pro Met Asp Tyr Trp Gly Gln Gly
225                 230                 235                 240

Thr Ser Val Thr Val Ser Ser
            245
```

<210> SEQ ID NO 7
<211> LENGTH: 1518
<212> TYPE: DNA
<213> ORGANISM: Artificial
<220> FEATURE:
<223> OTHER INFORMATION: DNA sequence of scFv-mycelia (dimer)

<400> SEQUENCE: 7

```
atggatattg ttctctccca gtctccaaca atcatgtctg catctccagg ggagaaggtc      60
accatgacct gcagtgccag ctcaagtgta agttacatgc actggtacca gcagaagtca     120
ggcacctccc ccaaaagatg gatttatgac acatccaaac tggcttctgg agtccctgct     180
cgcttcagtg gcagtgggtc tgggaccccct accctctca caatcagcag catggaggct     240
gaagatgctg ccacttatta ctgcctgcag tggagtagta acccgtggac gttcggtgga     300
ggcaccaagc tggagctgaa acgtggtggt ggtggttctg gtggtggtgg ttctggcggc     360
ggcggctccg gtggtggtgg atcccaggtg cagctgaagc aatctggggc tgaactggca     420
aaacctgggg cctcagtgaa gatgtcctgc aaggcttctg gctacacctt tactagctac     480
tggatgcact gggtaaaaca gaggcctgga cagggtctgg aatggattgg atacattaat     540
cctagcactg gttatactga gtacaatcag aagttcaagg acaaggccac attgactgca     600
gacaaatcct ccagcacagc ctacatgcaa ctgagcagcc tgacatctga ggactctgca     660
gtctattact gtgcaagaaa gttctatggt aacttcccta tggactactg ggtcaagga      720
acctcagtca ccgtctcctc gggaggagga ggatcaggag gaggaggatc acatatggat     780
attgttctct cccagtctcc aacaatcatg tctgcatctc aggggagaa ggtcaccatg      840
acctgcagtg ccagctcaag tgtaagttac atgcactggt accagcagaa gtcaggcacc     900
tcccccaaaa gatggattta tgacacatcc aaactggctt ctggagtccc tgctcgcttc     960
agtggcagtg ggtctgggac cccttaccct ctcacaatca gcagcatgga ggctgaagat    1020
gctgccactt attactgcct gcagtggagt agtaacccgt ggacgttcgg tggaggcacc    1080
aagctggagc tgaacgtgg tggtggtggt tctggtggtg gtggttctgg cggcggcggc    1140
tccggtggtg gtggatccca ggtgcagctg aagcaatctg gggctgaact ggcaaaacct    1200
ggggcctcag tgaagatgtc ctgcaaggct tctggctaca cctttactag ctactggatg    1260
cactgggtaa aacagaggcc tggacaggggt ctggaatgga ttggatacat taatcctagc    1320
```

-continued

```
actggttata ctgagtacaa tcagaagttc aaggacaagg ccacattgac tgcagacaaa    1380
tcctccagca cagcctacat gcaactgagc agcctgacat ctgaggactc tgcagtctat    1440
tactgtgcaa gaaagttcta tggtaacttc cctatggact actggggtca aggaacctca    1500
gtcaccgtct cctcgtaa                                                 1518
```

<210> SEQ ID NO 8
<211> LENGTH: 505
<212> TYPE: PRT
<213> ORGANISM: Artificial
<220> FEATURE:
<223> OTHER INFORMATION: Protein sequence of scFv-mycelia (dimer)

<400> SEQUENCE: 8

```
Met Asp Ile Val Leu Ser Gln Ser Pro Thr Ile Met Ser Ala Ser Pro
1               5                   10                  15

Gly Glu Lys Val Thr Met Thr Cys Ser Ala Ser Ser Ser Val Ser Tyr
                20                  25                  30

Met His Trp Tyr Gln Gln Lys Ser Gly Thr Ser Pro Lys Arg Trp Ile
            35                  40                  45

Tyr Asp Thr Ser Lys Leu Ala Ser Gly Val Pro Ala Arg Phe Ser Gly
        50                  55                  60

Ser Gly Ser Gly Thr Pro Tyr Pro Leu Thr Ile Ser Ser Met Glu Ala
65                  70                  75                  80

Glu Asp Ala Ala Thr Tyr Tyr Cys Leu Gln Trp Ser Ser Asn Pro Trp
                85                  90                  95

Thr Phe Gly Gly Gly Thr Lys Leu Glu Leu Lys Arg Gly Gly Gly Gly
            100                 105                 110

Ser Gly Gly Gly Gly Ser Gly Gly Gly Ser Gly Gly Gly Gly Ser
        115                 120                 125

Gln Val Gln Leu Lys Gln Ser Gly Ala Glu Leu Ala Lys Pro Gly Ala
130                 135                 140

Ser Val Lys Met Ser Cys Lys Ala Ser Gly Tyr Thr Phe Thr Ser Tyr
                145                 150                 155                 160

Trp Met His Trp Val Lys Gln Arg Pro Gly Gln Gly Leu Glu Trp Ile
            165                 170                 175

Gly Tyr Ile Asn Pro Ser Thr Gly Tyr Thr Glu Tyr Asn Gln Lys Phe
        180                 185                 190

Lys Asp Lys Ala Thr Leu Thr Ala Asp Lys Ser Ser Ser Thr Ala Tyr
    195                 200                 205

Met Gln Leu Ser Ser Leu Thr Ser Glu Asp Ser Ala Val Tyr Tyr Cys
210                 215                 220

Ala Arg Lys Phe Tyr Gly Asn Phe Pro Met Asp Tyr Trp Gly Gln Gly
225                 230                 235                 240

Thr Ser Val Thr Val Ser Ser Gly Gly Gly Ser Gly Gly Gly Gly
                245                 250                 255

Ser His Met Asp Ile Val Leu Ser Gln Ser Pro Thr Ile Met Ser Ala
            260                 265                 270

Ser Pro Gly Glu Lys Val Thr Met Thr Cys Ser Ala Ser Ser Ser Val
        275                 280                 285

Ser Tyr Met His Trp Tyr Gln Gln Lys Ser Gly Thr Ser Pro Lys Arg
    290                 295                 300

Trp Ile Tyr Asp Thr Ser Lys Leu Ala Ser Gly Val Pro Ala Arg Phe
305                 310                 315                 320

Ser Gly Ser Gly Ser Gly Thr Pro Tyr Pro Leu Thr Ile Ser Ser Met
                325                 330                 335
```

```
Glu Ala Glu Asp Ala Ala Thr Tyr Tyr Cys Leu Gln Trp Ser Ser Asn
                340                 345                 350

Pro Trp Thr Phe Gly Gly Gly Thr Lys Leu Glu Leu Lys Arg Gly Gly
            355                 360                 365

Gly Gly Ser Gly Gly Gly Gly Ser Gly Gly Gly Ser Gly Gly Gly Gly
        370                 375                 380

Gly Ser Gln Val Gln Leu Lys Gln Ser Gly Ala Glu Leu Ala Lys Pro
385                 390                 395                 400

Gly Ala Ser Val Lys Met Ser Cys Lys Ala Ser Gly Tyr Thr Phe Thr
                405                 410                 415

Ser Tyr Trp Met His Trp Val Lys Gln Arg Pro Gly Gln Gly Leu Glu
            420                 425                 430

Trp Ile Gly Tyr Ile Asn Pro Ser Thr Gly Tyr Thr Glu Tyr Asn Gln
        435                 440                 445

Lys Phe Lys Asp Lys Ala Thr Leu Thr Ala Asp Lys Ser Ser Ser Thr
    450                 455                 460

Ala Tyr Met Gln Leu Ser Ser Leu Thr Ser Glu Asp Ser Ala Val Tyr
465                 470                 475                 480

Tyr Cys Ala Arg Lys Phe Tyr Gly Asn Phe Pro Met Asp Tyr Trp Gly
                485                 490                 495

Gln Gly Thr Ser Val Thr Val Ser Ser
            500                 505

<210> SEQ ID NO 9
<211> LENGTH: 927
<212> TYPE: DNA
<213> ORGANISM: Artificial
<220> FEATURE:
<223> OTHER INFORMATION: DNA sequence of scFv-defensin (partial)

<400> SEQUENCE: 9
atgcagaagt tgtgcgaaag gccaagtggg acatggtcag gagtctgtgg aaacaataac      60
gcatgcaaga atcagtgcat taaccttgag aaagcacgac atggatcttg caactatgtc     120
ttcccagctc acaagtgtat ctgctacttt ccttgtggtg gtggtggttc tggcggcggc     180
ggctccgata ttgttctctc ccagtctcca acaatcatgt ctgcatctcc aggggagaag     240
gtcaccatga cctgcagtgc cagctcaagt gtaagttaca tgcactggta ccagcagaag     300
tcaggcacct cccccaaaag atggatttat gacacatcca actggcttc tggagtccct     360
gctcgcttca gtggcagtgg gtctgggacc ccttaccctc tcacaatcag cagcatggag     420
gctgaagatg ctgccactta ttactgcctg cagtggagta gtaacccgtg gacgttcggt     480
ggaggcacca agctggagct gaaacgtggt ggtggtggtt ctggtggtgg tggttctggc     540
ggcggcggct ccggtggtgg tggatcccag gtgcagctga agcaatctgg ggctgaactg     600
gcaaaacctg gggcctcagt gaagatgtcc tgcaaggctt ctggctacac ctttactagc     660
tactggatgc actgggtaaa cagaggcct ggacagggtc tggaatggat tggatacatt     720
aatcctagca ctggttatac tgagtacaat cagaagttca aggacaaggc cacattgact     780
gcagacaaat cctccagcac agcctacatg caactgagca gcctgacatc tgaggactct     840
gcagtctatt actgtgcaag aaagttctat ggtaacttcc ctatggacta ctggggtcaa     900
ggaacctcag tcaccgtctc ctcgtaa                                          927

<210> SEQ ID NO 10
<211> LENGTH: 308
<212> TYPE: PRT
<213> ORGANISM: Artificial
```

<220> FEATURE:
<223> OTHER INFORMATION: Protein sequence of scFv-defensin (partial)

<400> SEQUENCE: 10

```
Met Gln Lys Leu Cys Glu Arg Pro Ser Gly Thr Trp Ser Gly Val Cys
1               5                   10                  15

Gly Asn Asn Ala Cys Lys Asn Gln Cys Ile Asn Leu Glu Lys Ala
            20                  25                  30

Arg His Gly Ser Cys Asn Tyr Val Phe Pro Ala His Lys Cys Ile Cys
            35                  40                  45

Tyr Phe Pro Cys Gly Gly Gly Ser Gly Gly Gly Gly Ser Asp Ile
    50                  55                  60

Val Leu Ser Gln Ser Pro Thr Ile Met Ser Ala Ser Pro Gly Glu Lys
65              70                  75                  80

Val Thr Met Thr Cys Ser Ala Ser Ser Val Ser Tyr Met His Trp
                85                  90                  95

Tyr Gln Gln Lys Ser Gly Thr Ser Pro Lys Arg Trp Ile Tyr Asp Thr
                100                 105                 110

Ser Lys Leu Ala Ser Gly Val Pro Ala Arg Phe Ser Gly Ser Gly Ser
            115                 120                 125

Gly Thr Pro Tyr Pro Leu Thr Ile Ser Ser Met Glu Ala Glu Asp Ala
    130                 135                 140

Ala Thr Tyr Tyr Cys Leu Gln Trp Ser Ser Asn Pro Trp Thr Phe Gly
145                 150                 155                 160

Gly Gly Thr Lys Leu Glu Leu Lys Arg Gly Gly Gly Ser Gly Gly
                165                 170                 175

Gly Gly Ser Gly Gly Gly Ser Gly Gly Gly Ser Gln Val Gln
            180                 185                 190

Leu Lys Gln Ser Gly Ala Glu Leu Ala Lys Pro Gly Ala Ser Val Lys
            195                 200                 205

Met Ser Cys Lys Ala Ser Gly Tyr Thr Phe Thr Ser Tyr Trp Met His
        210                 215                 220

Trp Val Lys Gln Arg Pro Gly Gln Gly Leu Glu Trp Ile Gly Tyr Ile
225                 230                 235                 240

Asn Pro Ser Thr Gly Tyr Thr Glu Tyr Asn Gln Lys Phe Lys Asp Lys
                245                 250                 255

Ala Thr Leu Thr Ala Asp Lys Ser Ser Ser Thr Ala Tyr Met Gln Leu
            260                 265                 270

Ser Ser Leu Thr Ser Glu Asp Ser Ala Val Tyr Tyr Cys Ala Arg Lys
            275                 280                 285

Phe Tyr Gly Asn Phe Pro Met Asp Tyr Trp Gly Gln Gly Thr Ser Val
    290                 295                 300

Thr Val Ser Ser
305
```

<210> SEQ ID NO 11
<211> LENGTH: 1011
<212> TYPE: DNA
<213> ORGANISM: Artificial
<220> FEATURE:
<223> OTHER INFORMATION: DNA sequence of scFv-defensin (full)

<400> SEQUENCE: 11

```
atggctaagt tgcgtccat catcgcactt ctttttgctg ctcttgttct ttttgctgct      60
ttcgaagcac caacaatggt ggaagcacag aagttgtgcg aaaggccaag tgggacatgg     120
tcaggagtct gtggaaacaa taacgcatgc aagaatcagt gcattaacct tgagaaagca     180
```

```
cgacatggat cttgcaacta tgtcttccca gctcacaagt gtatctgcta ctttccttgt      240
ggtggtggtg gttctggcgg cggcggctcc gatattgttc tctcccagtc tccaacaatc      300
atgtctgcat ctccagggga gaaggtcacc atgacctgca gtgccagctc aagtgtaagt      360
tacatgcact ggtaccagca gaagtcaggc acctccccca aaagatggat ttatgacaca      420
tccaaactgg cttctggagt ccctgctcgc ttcagtggca gtgggtctgg gaccccttac      480
cctctcacaa tcagcagcat ggaggctgaa gatgctgcca cttattactg cctgcagtgg      540
agtagtaacc cgtggacgtt cggtggaggc accaagctgg agctgaaacg tggtggtggt      600
ggttctggtg gtggtggttc tggcggcggc ggctccggtg gtggtggatc ccaggtgcag      660
ctgaagcaat ctggggctga actggcaaaa cctggggcct cagtgaagat gtcctgcaag      720
gcttctggct acacctttac tagctactgg atgcactggg taaaacagag gcctggacag      780
ggtctggaat ggattggata cattaatcct agcactggtt atactgagta caatcagaag      840
ttcaaggaca aggccacatt gactgcagac aaatcctcca gcacagccta catgcaactg      900
agcagcctga catctgagga ctctgcagtc tattactgtg caagaaagtt ctatggtaac      960
ttccctatgg actactgggg tcaaggaacc tcagtcaccg tctcctcgta a             1011
```

<210> SEQ ID NO 12
<211> LENGTH: 336
<212> TYPE: PRT
<213> ORGANISM: Artificial
<220> FEATURE:
<223> OTHER INFORMATION: Protein sequence of scFv-defensin (full)

<400> SEQUENCE: 12

```
Met Ala Lys Phe Ala Ser Ile Ile Ala Leu Leu Phe Ala Ala Leu Val
1               5                   10                  15

Leu Phe Ala Ala Phe Glu Ala Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80

Gly Gly Gly Gly Ser Gly Gly Gly Ser Asp Ile Val Leu Ser Gln
                85                  90                  95

Ser Pro Thr Ile Met Ser Ala Ser Pro Gly Glu Lys Val Thr Met Thr
            100                 105                 110

Cys Ser Ala Ser Ser Val Ser Tyr Met His Trp Tyr Gln Gln Lys
        115                 120                 125

Ser Gly Thr Ser Pro Lys Arg Trp Ile Tyr Asp Thr Ser Lys Leu Ala
    130                 135                 140

Ser Gly Val Pro Ala Arg Phe Ser Gly Ser Gly Ser Gly Thr Pro Tyr
145                 150                 155                 160

Pro Leu Thr Ile Ser Ser Met Glu Ala Glu Asp Ala Ala Thr Tyr Tyr
                165                 170                 175

Cys Leu Gln Trp Ser Ser Asn Pro Trp Thr Phe Gly Gly Gly Thr Lys
            180                 185                 190

Leu Glu Leu Lys Arg Gly Gly Gly Ser Gly Gly Gly Gly Ser Gly
        195                 200                 205

Gly Gly Gly Ser Gly Gly Gly Ser Gln Val Gln Leu Lys Gln Ser
    210                 215                 220
```

```
Gly Ala Glu Leu Ala Lys Pro Gly Ala Ser Val Lys Met Ser Cys Lys
225                 230                 235                 240

Ala Ser Gly Tyr Thr Phe Thr Ser Tyr Trp Met His Trp Val Lys Gln
            245                 250                 255

Arg Pro Gly Gln Gly Leu Glu Trp Ile Gly Tyr Ile Asn Pro Ser Thr
        260                 265                 270

Gly Tyr Thr Glu Tyr Asn Gln Lys Phe Lys Asp Lys Ala Thr Leu Thr
    275                 280                 285

Ala Asp Lys Ser Ser Ser Thr Ala Tyr Met Gln Leu Ser Ser Leu Thr
290                 295                 300

Ser Glu Asp Ser Ala Val Tyr Tyr Cys Ala Arg Lys Phe Tyr Gly Asn
305                 310                 315                 320

Phe Pro Met Asp Tyr Trp Gly Gln Gly Thr Ser Val Thr Val Ser Ser
            325                 330                 335
```

<210> SEQ ID NO 13
<211> LENGTH: 1737
<212> TYPE: DNA
<213> ORGANISM: Artificial
<220> FEATURE:
<223> OTHER INFORMATION: DNA sequence of scFv-chitinase

<400> SEQUENCE: 13

```
atgaagtctt gtctacttct ctttctcatc ttctcatttc ttttatcatt ttccttagcc      60
gagcaatgtg gtcgacaagc gggaggagct ctctgcccca acggtctatg ctgcagcgag     120
ttcggatggt gcggtgacac cgaagcttac tgtaagcagc ctggctgcca agccagtgc      180 ggtggtactc ctcctggccc caccggtgat ctttcaggca tcatttcaag atctcagttc     240
gacgacatgc ttaaacatag aaatgataat gcttgtcccg ctagaggttt ctacacttat     300
gatgccttta tcaatgccgc taagtctttc cctggcttcg gcaccaccgg agacactgcc     360
acaaggaaga agaaaatcgc tgccttcttt ggtcagactt cccacgagac acccggtggg     420
tgggccacag caccagacgg accatattca tggggatact gtttcaaaca agagcagaac     480
ccttcttcaa actactgttc accgagtgcc gaatggccat cgcatctgg taaaagctac      540 tacggaagag gaccaatgca gctatcatgg aactacaact acggacagtg tggaagagcc     600
atcggatctg acttactcaa caaccctgac cttgtctcca cgatccagt gatcgctttc      660 aaagccgcga tttggttttg gatgacacct cagtctccaa aaccgtcgtg ccacgccgtg     720
atcgtcggcc agtggcagcc ttcggatgct gaccgtgccg ctgggagagt accgggttac     780
ggtgtgatta cgaatattat taacggtggt ttagagtgtg gacgcggcca agacgctaga     840
gtcgcggata gaattggatt ttaccagagg tactgtaaca ttcttggagt taatcctgga     900
ggtaaccttg attgttacaa ccaaaggtcc tttgcttctg ttaacttctt ccttgacgct     960
gctattggtg gtggtggttc tggcggcggc ggctccgata ttgttctctc ccagtctcca    1020
acaatcatgt ctgcatctcc aggggagaag gtcaccatga cctgcagtgc cagctcaagt    1080
gtaagttaca tgcactggta ccagcagaag tcaggcacct cccccaaaag atggatttat    1140
gacacatcca actggcttc tggagtccct gctcgcttca gtggcagtgg gtctgggacc     1200
ccttaccctc tcacaatcag cagcatggag gctgaagatg ctgccactta ttactgcctg    1260
cagtggagta gtaacccgtg gacgttcggt ggaggcacca agctgagct gaaacgtggt     1320 ggtggtggtt ctggtggtgg tggttctggc ggcggcggct ccggtggtgg tggatcccag    1380
gtgcagctga gcaatctgg ggctgaactg gcaaaacctg ggcctcagt gaagatgtcc      1440 tgcaaggctt ctggctacac ctttactagc tactggatgc actgggtaaa acagaggcct    1500
```

```
ggacagggtc tggaatggat tggatacatt aatcctagca ctggttatac tgagtacaat    1560
cagaagttca aggacaaggc cacattgact gcagacaaat cctccagcac agcctacatg    1620
caactgagca gcctgacatc tgaggactct gcagtctatt actgtgcaag aaagttctat    1680
ggtaacttcc ctatggacta ctggggtcaa ggaacctcag tcaccgtctc ctcgtaa      1737

<210> SEQ ID NO 14
<211> LENGTH: 578
<212> TYPE: PRT
<213> ORGANISM: Artificial
<220> FEATURE:
<223> OTHER INFORMATION: Protein sequence of scFv-chitinase

<400> SEQUENCE: 14

Met Lys Ser Cys Leu Leu Phe Leu Ile Phe Ser Phe Leu Leu Ser
1               5                   10                  15

Phe Ser Leu Ala Glu Gln Cys Gly Arg Gln Ala Gly Gly Ala Leu Cys
            20                  25                  30

Pro Asn Gly Leu Cys Cys Ser Glu Phe Gly Trp Cys Gly Asp Thr Glu
        35                  40                  45

Ala Tyr Cys Lys Gln Pro Gly Cys Gln Ser Cys Gly Gly Thr Pro
    50                  55                  60

Pro Gly Pro Thr Gly Asp Leu Ser Gly Ile Ile Ser Arg Ser Gln Phe
65                  70                  75                  80

Asp Asp Met Leu Lys His Arg Asn Asp Asn Ala Cys Pro Ala Arg Gly
                85                  90                  95

Phe Tyr Thr Tyr Asp Ala Phe Ile Asn Ala Ala Lys Ser Phe Pro Gly
            100                 105                 110

Phe Gly Thr Thr Gly Asp Thr Ala Thr Arg Lys Lys Glu Ile Ala Ala
        115                 120                 125

Phe Phe Gly Gln Thr Ser His Glu Thr Thr Gly Gly Trp Ala Thr Ala
    130                 135                 140

Pro Asp Gly Pro Tyr Ser Trp Gly Tyr Cys Phe Lys Gln Glu Gln Asn
145                 150                 155                 160

Pro Ser Ser Asn Tyr Cys Ser Pro Ser Ala Glu Trp Pro Cys Ala Ser
                165                 170                 175

Gly Lys Ser Tyr Tyr Gly Arg Gly Pro Met Gln Leu Ser Trp Asn Tyr
            180                 185                 190

Asn Tyr Gly Gln Cys Gly Arg Ala Ile Gly Ser Asp Leu Leu Asn Asn
        195                 200                 205

Pro Asp Leu Val Ser Asn Asp Pro Val Ile Ala Phe Lys Ala Ala Ile
    210                 215                 220

Trp Phe Trp Met Thr Pro Gln Ser Pro Lys Pro Ser Cys His Ala Val
225                 230                 235                 240

Ile Val Gly Gln Trp Gln Pro Ser Asp Ala Asp Arg Ala Ala Gly Arg
                245                 250                 255

Val Pro Gly Tyr Gly Val Ile Thr Asn Ile Ile Asn Gly Gly Leu Glu
            260                 265                 270

Cys Gly Arg Gly Gln Asp Ala Arg Val Ala Asp Arg Ile Gly Phe Tyr
        275                 280                 285

Gln Arg Tyr Cys Asn Ile Leu Gly Val Asn Pro Gly Gly Asn Leu Asp
    290                 295                 300

Cys Tyr Asn Gln Arg Ser Phe Ala Ser Val Asn Phe Phe Leu Asp Ala
305                 310                 315                 320

Ala Ile Gly Gly Gly Gly Ser Gly Gly Gly Gly Ser Asp Ile Val Leu
                325                 330                 335
```

-continued

```
Ser Gln Ser Pro Thr Ile Met Ser Ala Ser Pro Gly Glu Lys Val Thr
            340                 345                 350

Met Thr Cys Ser Ala Ser Ser Val Ser Tyr Met His Trp Tyr Gln
            355                 360                 365

Gln Lys Ser Gly Thr Ser Pro Lys Arg Trp Ile Tyr Asp Thr Ser Lys
        370                 375                 380

Leu Ala Ser Gly Val Pro Ala Arg Phe Ser Gly Ser Gly Ser Gly Thr
385                 390                 395                 400

Pro Tyr Pro Leu Thr Ile Ser Ser Met Glu Ala Glu Asp Ala Ala Thr
                405                 410                 415

Tyr Tyr Cys Leu Gln Trp Ser Ser Asn Pro Trp Thr Phe Gly Gly Gly
            420                 425                 430

Thr Lys Leu Glu Leu Lys Arg Gly Gly Gly Gly Ser Gly Gly Gly Gly
            435                 440                 445

Ser Gly Gly Gly Gly Ser Gly Gly Gly Gly Ser Gln Val Gln Leu Lys
        450                 455                 460

Gln Ser Gly Ala Glu Leu Ala Lys Pro Gly Ala Ser Val Lys Met Ser
465                 470                 475                 480

Cys Lys Ala Ser Gly Tyr Thr Phe Thr Ser Tyr Trp Met His Trp Val
                485                 490                 495

Lys Gln Arg Pro Gly Gln Gly Leu Glu Trp Ile Gly Tyr Ile Asn Pro
            500                 505                 510

Ser Thr Gly Tyr Thr Glu Tyr Asn Gln Lys Phe Lys Asp Lys Ala Thr
        515                 520                 525

Leu Thr Ala Asp Lys Ser Ser Thr Ala Tyr Met Gln Leu Ser Ser
530                 535                 540

Leu Thr Ser Glu Asp Ser Ala Val Tyr Tyr Cys Ala Arg Lys Phe Tyr
545                 550                 555                 560

Gly Asn Phe Pro Met Asp Tyr Trp Gly Gln Gly Thr Ser Val Thr Val
                565                 570                 575

Ser Ser
```

<210> SEQ ID NO 15
<211> LENGTH: 741
<212> TYPE: DNA
<213> ORGANISM: Artificial
<220> FEATURE:
<223> OTHER INFORMATION: DNA sequence of scFv-aspartyl protease

<400> SEQUENCE: 15

```
atggatattg tgatgaccca gtctccagca ctcatgtctg catctccagg ggagaaggtc    60
accatgacct gcagtgccag ctcaagtgta agttacatgt actggtacca gcagaagcca   120
agatcctccc ccaaaccctg gatttatctc acatccaacc tggcttctgg agtccctgct   180
cgcttcagtg gcagtgggtc tgggacctct tactctctca caatcagcag catggaggct   240
gaagatgctg ccacttatta ctgccagcag tggagtagta cccgtacac gttcggaggg   300 gggaccaagc tggaaataaa acgtggtggt ggtggttctg gtggtggtgg ttctggcggc   360
ggcggctccg gtggtggtgg atccgacgtg atggtggtgg agtctggggg aggcttagtg   420
aagcctggag ggtccctgaa actctcctgt gcagcctctg gattcacttt cagtagctat   480
gccatgtctt gggttcgcca gactccggag aagaggctgg agtgggtcgc aaccattagt   540
agtggtggta gttacaccta ctatccaaac agtgtgaagg gccgattcac catctccaga   600
gacaatgcca agaacaccct gtacctgcaa atgagccgtc tgaagtctga ggacacagcc   660
```

```
atgtattact gtgcaagacg gagtgaactg ggactgtttg cttactgggg ccaagggact    720
ctggtcactg tctctgcgta a                                              741
```

<210> SEQ ID NO 16
<211> LENGTH: 246
<212> TYPE: PRT
<213> ORGANISM: Artificial
<220> FEATURE:
<223> OTHER INFORMATION: Protein sequence of scFv-aspartyl protease

<400> SEQUENCE: 16

```
Met Asp Ile Val Met Thr Gln Ser Pro Ala Leu Met Ser Ala Ser Pro
1               5                   10                  15

Gly Glu Lys Val Thr Met Thr Cys Ser Ala Ser Ser Ser Val Ser Tyr
                20                  25                  30

Met Tyr Trp Tyr Gln Gln Lys Pro Arg Ser Ser Pro Lys Pro Trp Ile
            35                  40                  45

Tyr Leu Thr Ser Asn Leu Ala Ser Gly Val Pro Ala Arg Phe Ser Gly
        50                  55                  60

Ser Gly Ser Gly Thr Ser Tyr Ser Leu Thr Ile Ser Ser Met Glu Ala
65                  70                  75                  80

Glu Asp Ala Ala Thr Tyr Tyr Cys Gln Gln Trp Ser Ser Asn Pro Tyr
                85                  90                  95

Thr Phe Gly Gly Gly Thr Lys Leu Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Asp Val Met Val Val Glu Ser Gly Gly Gly Leu Val Lys Pro Gly Gly
    130                 135                 140

Ser Leu Lys Leu Ser Cys Ala Ala Ser Gly Phe Thr Phe Ser Ser Tyr
145                 150                 155                 160

Ala Met Ser Trp Val Arg Gln Thr Pro Glu Lys Arg Leu Glu Trp Val
                165                 170                 175

Ala Thr Ile Ser Ser Gly Gly Ser Tyr Thr Tyr Tyr Pro Asn Ser Val
            180                 185                 190

Lys Gly Arg Phe Thr Ile Ser Arg Asp Asn Ala Lys Asn Thr Leu Tyr
        195                 200                 205

Leu Gln Met Ser Arg Leu Lys Ser Glu Asp Thr Ala Met Tyr Tyr Cys
    210                 215                 220

Ala Arg Arg Ser Glu Leu Gly Leu Phe Ala Tyr Trp Gly Gln Gly Thr
225                 230                 235                 240

Leu Val Thr Val Ser Ala
                245
```

<210> SEQ ID NO 17
<211> LENGTH: 759
<212> TYPE: DNA
<213> ORGANISM: Artificial
<220> FEATURE:
<223> OTHER INFORMATION: DNA sequence of scFv-pAK-May 2 #6

<400> SEQUENCE: 17

```
atggactaca aagatattca gataaaccag tctccatctt ccatgtatgc atctctagga    60
gagagagtca ctatcacttg caaggcgagt caggacatta atagctattt aagctggttc    120
cagcagaaac cagggaaatc tcctaagacc ctgatctatc gtgcaaacag attggtagat    180
```

```
ggggtcccat caaggttcag tggcagtgga tctgggcaag attattctct caccatcagc      240
agcctggagt atgaagatat gggaatttat tattgtctac agtatgatga gtttcctctc      300
acgttcggtg ctgggaccaa gctggaaatc aaacgtggtg gtggtggttc tggtggtggt      360
ggttctggcg gcggcggctc cggtggtggt ggatccgatg tacagcttca ggagtctgga      420
ggaggcttgg tacagcctgg gggttctctg agactctcct gtgcaacttc tgggttcacc      480
ttcactgatt actacatgag ctgggtccgc cagcctccag aaaggcact tgagtggttg        540 ggttttatta gaaacaaagc taatggttac aacagagt acagtgcatc tgtgaagggt         600
cggttcacca tctccagaga taattcccaa agcatcctct atcttcaaat gaacaccctg      660
agagctgagg acagtgccac ttattactgt gcaagagata agggatggtt acactttgac      720
tactggggcc aaggcaccac tctcacagtc tcctcgtaa                             759
```

<210> SEQ ID NO 18
<211> LENGTH: 252
<212> TYPE: PRT
<213> ORGANISM: Artificial
<220> FEATURE:
<223> OTHER INFORMATION: Protein sequence of scFv-pAK-May 2 #6

<400> SEQUENCE: 18

```
Met Asp Tyr Lys Asp Ile Gln Ile Asn Gln Ser Pro Ser Ser Met Tyr
1               5                   10                  15

Ala Ser Leu Gly Glu Arg Val Thr Ile Thr Cys Lys Ala Ser Gln Asp
            20                  25                  30

Ile Asn Ser Tyr Leu Ser Trp Phe Gln Gln Lys Pro Gly Lys Ser Pro
        35                  40                  45

Lys Thr Leu Ile Tyr Arg Ala Asn Arg Leu Val Asp Gly Val Pro Ser
    50                  55                  60

Arg Phe Ser Gly Ser Gly Ser Gly Gln Asp Tyr Ser Leu Thr Ile Ser
65                  70                  75                  80

Ser Leu Glu Tyr Glu Asp Met Gly Ile Tyr Tyr Cys Leu Gln Tyr Asp
                85                  90                  95

Glu Phe Pro Leu Thr Phe Gly Ala Gly Thr Lys Leu Glu Ile Lys Arg
            100                 105                 110

Gly Gly Gly Gly Ser Gly Gly Gly Gly Ser Gly Gly Gly Gly Ser Gly
        115                 120                 125

Gly Gly Gly Ser Asp Val Gln Leu Gln Glu Ser Gly Gly Gly Leu Val
    130                 135                 140

Gln Pro Gly Gly Ser Leu Arg Leu Ser Cys Ala Thr Ser Gly Phe Thr
145                 150                 155                 160

Phe Thr Asp Tyr Tyr Met Ser Trp Val Arg Gln Pro Pro Gly Lys Ala
                165                 170                 175

Leu Glu Trp Leu Gly Phe Ile Arg Asn Lys Ala Asn Gly Tyr Thr Thr
            180                 185                 190

Glu Tyr Ser Ala Ser Val Lys Gly Arg Phe Thr Ile Ser Arg Asp Asn
        195                 200                 205

Ser Gln Ser Ile Leu Tyr Leu Gln Met Asn Thr Leu Arg Ala Glu Asp
    210                 215                 220

Ser Ala Thr Tyr Tyr Cys Ala Arg Asp Lys Gly Trp Leu His Phe Asp
225                 230                 235                 240

Tyr Trp Gly Gln Gly Thr Thr Leu Thr Val Ser Ser
                245                 250
```

<210> SEQ ID NO 19
<211> LENGTH: 745
<212> TYPE: DNA
<213> ORGANISM: Artificial
<220> FEATURE:
<223> OTHER INFORMATION: DNA sequence of scFv-pAK-3

<400> SEQUENCE: 19

```
atggactaca aagatattca gatgacacag tctccatcct ccttatctgc ctctctggga    60
gaaagagtca gtctcacttg tcgggcaagt caggacattg gtagtagctt aaactggctt   120
cagcaggaac cagatggaac tattaaacgc ctgatctacg ccacatccag tttagattct   180
ggtgtcccca aaaggttcag tggcagtagg tctgggtcag attattctct caccatcagc   240
agccttgagt ctgaagattt tgtagactat tactgtctac aatatgctag ttctccgtac   300
acgttcggag gggggaccaa gctggaaata aaacgtggtg gtggtggttc tggtggtggt   360
ggttctggcg cggcggctc ctgtggtggt ggatcccagg ttcaactgca gcagcctggg   420
gcagagcttg tgaggtcagg gcctcagtc aagttgtcct gcacagcttc tggcttcaac   480
attaaagaca cctatatgca ctgggtgaag cagaggcctg aacagggcct ggagtggatt   540
ggaaggattg atcctgcgaa tggtaatact aaatatgacc cgaagttcca gggcaaggcc   600
actataacag cagacacatc ctccaacaca gcctacctgc agctcagcag cctgacatct   660
gaggacactg ccgtctatta ctgtgctaga aattacctct ttgactactg gggccaaggc   720
accactctca cagtcttcct cgtaa                                         745
```

<210> SEQ ID NO 20
<211> LENGTH: 247
<212> TYPE: PRT
<213> ORGANISM: Artificial
<220> FEATURE:
<223> OTHER INFORMATION: Protein sequence of scFv-pAK-3

<400> SEQUENCE: 20

```
Met Asp Tyr Lys Asp Ile Gln Met Thr Gln Ser Pro Ser Ser Leu Ser
1               5                   10                  15

Ala Ser Leu Gly Glu Arg Val Ser Leu Thr Cys Arg Ala Ser Gln Asp
            20                  25                  30

Ile Gly Ser Ser Leu Asn Trp Leu Gln Gln Glu Pro Asp Gly Thr Ile
        35                  40                  45

Lys Arg Leu Ile Tyr Ala Thr Ser Ser Leu Asp Ser Gly Val Pro Lys
    50                  55                  60

Arg Phe Ser Gly Ser Arg Ser Gly Ser Asp Tyr Ser Leu Thr Ile Ser
65                  70                  75                  80

Ser Leu Glu Ser Glu Asp Phe Val Asp Tyr Tyr Cys Leu Gln Tyr Ala
                85                  90                  95

Ser Ser Pro Tyr Thr Phe Gly Gly Gly Thr Lys Leu Glu Ile Lys Arg
            100                 105                 110

Gly Gly Gly Gly Ser Gly Gly Gly Gly Ser Gly Gly Gly Gly Ser Cys
        115                 120                 125

Gly Gly Gly Ser Gln Val Gln Leu Gln Gln Pro Gly Ala Glu Leu Val
    130                 135                 140

Arg Ser Gly Ala Ser Val Lys Leu Ser Cys Thr Ala Ser Gly Phe Asn
145                 150                 155                 160

Ile Lys Asp Thr Tyr Met His Trp Val Lys Gln Arg Pro Glu Gln Gly
                165                 170                 175

Leu Glu Trp Ile Gly Arg Ile Asp Pro Ala Asn Gly Asn Thr Lys Tyr
            180                 185                 190
```

```
Asp Pro Lys Phe Gln Gly Lys Ala Thr Ile Thr Ala Asp Thr Ser Ser
        195                 200                 205

Asn Thr Ala Tyr Leu Gln Leu Ser Ser Leu Thr Ser Glu Asp Thr Ala
    210                 215                 220

Val Tyr Tyr Cys Ala Arg Asn Tyr Leu Phe Asp Tyr Trp Gly Gln Gly
225                 230                 235                 240

Thr Thr Leu Thr Val Phe Leu
            245
```

<210> SEQ ID NO 21
<211> LENGTH: 744
<212> TYPE: DNA
<213> ORGANISM: Artificial
<220> FEATURE:
<223> OTHER INFORMATION: DNA sequence of scFv-pAK-6

<400> SEQUENCE: 21

```
atggactaca aagacatcca gatgacacag actccagcaa tcatgtctgc atctctaggg      60
gaacgggtca ccatgacctg cactgccagc tcaagtgtaa gttccagtta cttgcactgg     120
taccagcaga agccaggatc ctcccccaaa ctctggattt atagcacatc caacctggct     180
tctggagtcc cagctcgctt cagtggcagt aggtctggga cctcttactc tctcacaatc     240
agcagcatgg aggctgaaga tgctgccact tattactgcc accagtatca tcgttccccg     300
tggacgttcg gtggaggcac caagctggag ctgaaacgtg gtggtggtgg ttctggtggt     360
ggtggttctg gcggcggcgg ctccggtggt ggtggatccg aggtccaact gcaacaatct     420
ggggctgaac tggcaaaacc tggggcctca gtgaagatgt cctgcaaggc ttctggctac     480
acctttacta gctactggat gcactgggta aaacagaggc ctggacaggg tctggaatgg     540
attggataca ttaatcctag cactggttat actgagtaca tcagaagtt caaggacaag     600 gccacattga ctgcagacaa atcctccagc acagcctaca tgcaactgag cagcctgaca     660
tctgaggact ctgcagtcta ttactgtgca agtagtagct tgcttactg gggccaaggg     720 actctggtca ctgtctctgc gtaa                                            744
```

<210> SEQ ID NO 22
<211> LENGTH: 247
<212> TYPE: PRT
<213> ORGANISM: Artificial
<220> FEATURE:
<223> OTHER INFORMATION: Protein sequence of scFv-pAK-6

<400> SEQUENCE: 22

```
Met Asp Tyr Lys Asp Ile Gln Met Thr Gln Thr Pro Ala Ile Met Ser
1               5                   10                  15

Ala Ser Leu Gly Glu Arg Val Thr Met Thr Cys Thr Ala Ser Ser Ser
            20                  25                  30

Val Ser Ser Tyr Leu His Trp Tyr Gln Gln Lys Pro Gly Ser Ser
        35                  40                  45

Pro Lys Leu Trp Ile Tyr Ser Thr Ser Asn Leu Ala Ser Gly Val Pro
    50                  55                  60

Ala Arg Phe Ser Gly Ser Arg Ser Gly Thr Ser Tyr Ser Leu Thr Ile
65                  70                  75                  80

Ser Ser Met Glu Ala Glu Asp Ala Ala Thr Tyr Tyr Cys His Gln Tyr
                85                  90                  95

His Arg Ser Pro Trp Thr Phe Gly Gly Gly Thr Lys Leu Glu Leu Lys
            100                 105                 110
```

```
Arg Gly Gly Gly Gly Ser Gly Gly Gly Ser Gly Gly Gly Gly Ser
            115                 120                 125

Gly Gly Gly Gly Ser Glu Val Gln Leu Gln Gln Ser Gly Ala Glu Leu
        130                 135                 140

Ala Lys Pro Gly Ala Ser Val Lys Met Ser Cys Lys Ala Ser Gly Tyr
145                 150                 155                 160

Thr Phe Thr Ser Tyr Trp Met His Trp Val Lys Gln Arg Pro Gly Gln
                165                 170                 175

Gly Leu Glu Trp Ile Gly Tyr Ile Asn Pro Ser Thr Gly Tyr Thr Glu
            180                 185                 190

Tyr Asn Gln Lys Phe Lys Asp Lys Ala Thr Leu Thr Ala Asp Lys Ser
        195                 200                 205

Ser Ser Thr Ala Tyr Met Gln Leu Ser Ser Leu Thr Ser Glu Asp Ser
210                 215                 220

Ala Val Tyr Tyr Cys Ala Ser Ser Ser Phe Ala Tyr Trp Gly Gln Gly
225                 230                 235                 240

Thr Leu Val Thr Val Ser Ala
                245

<210> SEQ ID NO 23
<211> LENGTH: 762
<212> TYPE: DNA
<213> ORGANISM: Artificial
<220> FEATURE:
<223> OTHER INFORMATION: DNA sequence of scFv-pAK-9

<400> SEQUENCE: 23
atggactaca aagacattga gctgacccaa tctccagctt ctttggctgt gtctctaggg     60
cagagggcca ccatctcctg cagagccagc gaaagtgttg ataattatgg cattagtttt    120
atgaactggt tccaacagaa accaggacag ccacccaaac tcctcatcta tgctgcatcc    180
aaccaaggat ccggggtccc tgccaggttt agtggcagtg gtctgggac  agacttcagc    240 ctcaacatcc atcctatgga ggaggatgat actgcaatgt atttctgtca gcaaagtaag    300
gaggttccgt ggacgttcgg tggaggcacc aagctggaaa taaaacgtgg tggtggtggt    360
tctggtggtg gtggttctgg cggcggcggc tccggtggtg gtggatccga ggtccagctg    420
caacagtcag gacctggcct ggtggcgccc tcacagagcc tgtccatcac atgcactgtc    480
tcagggttct cattaaccga ctatggtgta agctggattc gccagcctcc aggaaagggt    540
ctggagtggc tgggagtaat atggggtggt ggaagcacat actataattc agctctcaaa    600
tccagactga gcatcagcaa ggacaactcc aagagccaag ttctcttaaa aatgaacagt    660
ctgcaaactg atgacacagc catgtactac tgtgccaaac atggggctgg ttactacttt    720
gactactggg gccaaggcac cactctcaca gtctcctcgt aa                       762

<210> SEQ ID NO 24
<211> LENGTH: 253
<212> TYPE: PRT
<213> ORGANISM: Artificial
<220> FEATURE:
<223> OTHER INFORMATION: Protein sequence of scFv-pAK-9

<400> SEQUENCE: 24

Met Asp Tyr Lys Asp Ile Glu Leu Thr Gln Ser Pro Ala Ser Leu Ala
1               5                   10                  15

Val Ser Leu Gly Gln Arg Ala Thr Ile Ser Cys Arg Ala Ser Glu Ser
            20                  25                  30
```

Val Asp Asn Tyr Gly Ile Ser Phe Met Asn Trp Phe Gln Gln Lys Pro
         35                  40                  45
Gly Gln Pro Pro Lys Leu Leu Ile Tyr Ala Ala Ser Asn Gln Gly Ser
         50                  55                  60
Gly Val Pro Ala Arg Phe Ser Gly Ser Gly Thr Asp Phe Ser
65                  70                  75                  80
Leu Asn Ile His Pro Met Glu Glu Asp Thr Ala Met Tyr Phe Cys
                 85                  90                  95
Gln Gln Ser Lys Glu Val Pro Trp Thr Phe Gly Gly Thr Lys Leu
                100                 105                 110
Glu Ile Lys Arg Gly Gly Gly Ser Gly Gly Gly Ser Gly Gly
            115                 120                 125
Gly Ser Gly Gly Gly Gly Ser Glu Val Gln Leu Gln Gln Ser Gly
            130                 135                 140
Pro Gly Leu Val Ala Pro Ser Gln Ser Leu Ser Ile Thr Cys Thr Val
145                 150                 155                 160
Ser Gly Phe Ser Leu Thr Asp Tyr Gly Val Ser Trp Ile Arg Gln Pro
                165                 170                 175
Pro Gly Lys Gly Leu Glu Trp Leu Gly Val Ile Trp Gly Gly Gly Ser
            180                 185                 190
Thr Tyr Tyr Asn Ser Ala Leu Lys Ser Arg Leu Ser Ile Ser Lys Asp
                195                 200                 205
Asn Ser Lys Ser Gln Val Leu Leu Lys Met Asn Ser Leu Gln Thr Asp
            210                 215                 220
Asp Thr Ala Met Tyr Tyr Cys Ala Lys His Gly Ala Gly Tyr Tyr Phe
225                 230                 235                 240
Asp Tyr Trp Gly Gln Gly Thr Thr Leu Thr Val Ser Ser
                245                 250

<210> SEQ ID NO 25
<211> LENGTH: 750
<212> TYPE: DNA
<213> ORGANISM: Artificial
<220> FEATURE:
<223> OTHER INFORMATION: DNA sequence of scFv-pAK-10

<400> SEQUENCE: 25

```
atggactaca aagatattgt gctcacccaa tctccagcaa tcatgtctgc atctccaggg      60
gagaaggtca ccatgacctg cagtgccagc tcaagtgtaa gttacatgca ctggtaccag     120
cagaagtcag gcacctcccc caaaagatgg atttatgaca catccaaact ggcttctgga     180
gtccctgctc gcttcagtgg cagtgggtct gggacctctt accctctcac aatcagcagc     240
atggaggctg aagatgctgc cacttattac tgccagcagt ggagtagtaa cccactcacg     300
ttcggtgctg ggaccaaact gactgtccta ggtggtggtg gtggttctgg tggtggtggt     360
tccggcggcg gcggctccgg tggtggtgga tccgaggtcc agctccagca gtccggggct     420
gaactggtga agcctggggc ttcagtgaag ttgtcctgca aggcttctgg ctacaccttc     480
accagctact atatgtactg ggtgaagcag aggcctggac aaggccttga gtggattgga     540
gagattttac ctggaagtgg tagtactaac ttcaatgaga agttcaagag caaggccaca     600
ctgactgtag acaaatcctc cagcacagcc tacatgcaac tcagcagcct gacatctgag     660
gactctgcgt ctattactg tacaagaggg cattactacg ctgctttga ctactggggc      720 caaggcacca ctctcacagt ctcctcgtaa                                     750
```

```
<210> SEQ ID NO 26
<211> LENGTH: 249
<212> TYPE: PRT
<213> ORGANISM: Artificial
<220> FEATURE:
<223> OTHER INFORMATION: Protein sequence of scFv-pAK-10

<400> SEQUENCE: 26

Met Asp Tyr Lys Asp Ile Val Leu Thr Gln Ser Pro Ala Ile Met Ser
1               5                   10                  15

Ala Ser Pro Gly Glu Lys Val Thr Met Thr Cys Ser Ala Ser Ser Ser
            20                  25                  30

Val Ser Tyr Met His Trp Tyr Gln Gln Lys Ser Gly Thr Ser Pro Lys
        35                  40                  45

Arg Trp Ile Tyr Asp Thr Ser Lys Leu Ala Ser Gly Val Pro Ala Arg
    50                  55                  60

Phe Ser Gly Ser Gly Ser Gly Thr Ser Tyr Pro Leu Thr Ile Ser Ser
65                  70                  75                  80

Met Glu Ala Glu Asp Ala Ala Thr Tyr Tyr Cys Gln Gln Trp Ser Ser
                85                  90                  95

Asn Pro Leu Thr Phe Gly Ala Gly Thr Lys Leu Thr Val Leu Gly Gly
            100                 105                 110

Gly Gly Gly Ser Gly Gly Gly Gly Ser Gly Gly Gly Ser Gly Gly
        115                 120                 125

Gly Gly Ser Glu Val Gln Leu Gln Gln Ser Gly Ala Glu Leu Val Lys
    130                 135                 140

Pro Gly Ala Ser Val Lys Leu Ser Cys Lys Ala Ser Gly Tyr Thr Phe
145                 150                 155                 160

Thr Ser Tyr Tyr Met Tyr Trp Val Lys Gln Arg Pro Gly Gln Gly Leu
                165                 170                 175

Glu Trp Ile Gly Glu Ile Leu Pro Gly Ser Gly Ser Thr Asn Phe Asn
            180                 185                 190

Glu Lys Phe Lys Ser Lys Ala Thr Leu Thr Val Asp Lys Ser Ser Ser
        195                 200                 205

Thr Ala Tyr Met Gln Leu Ser Ser Leu Thr Ser Glu Asp Ser Ala Val
    210                 215                 220

Tyr Tyr Cys Thr Arg Gly His Tyr Tyr Gly Cys Phe Asp Tyr Trp Gly
225                 230                 235                 240

Gln Gly Thr Thr Leu Thr Val Ser Ser
                245

<210> SEQ ID NO 27
<211> LENGTH: 756
<212> TYPE: DNA
<213> ORGANISM: Artificial
<220> FEATURE:
<223> OTHER INFORMATION: DNA sequence of polyhistidine tagged
      scFv-SSPG1d-peptide

<400> SEQUENCE: 27
atggacattg tgttgacaca gtctccagca atcatgtctg catctccagg ggaaaaggtc      60
accatgacct gcagtgccag ctcaagtgta agttacatgc actggtacca gcagaagtca     120
agcacctccc ccaaactctg gatttatgac acatccaaac tggcttctgg agtcccaggt     180
cgcttcagtg gcagtgggtc tggaaactct tactctctca cgatcagcag catggaggct     240
gaagatgttg ccacttatta ctgttttcag gggagtgggt acccgctcac gttcggtgct     300
gggaccaagc tggaaatcaa acgtggtgct ggtggttctg gtggtggtgg ttctggcggc     360
```

```
ggcggctccg gtggtggtgg atcccaggtc cagcttcagc aatctggggc tgagctggtg      420
aggcctgggt cctcagtgaa gatttcctgc aaggcttctg gctatgcatt cagtaactac      480
tggatgaact gggtgaagca gaggcctgga cagggtcttg agtggattgg acagatttat      540
cctggatatg gtgatgctaa atacaatgga aagttcaagg gtaaggccac gctgactgca      600
gacatatcct ccagcacagc ctatatgcag ctcagcagcc taacatctga ggactctgca      660
gtctatttct gtgcaagatc atcttacgag gctaactggg gccaagggac tctggtcact      720
gtctctgcgc tcgagcacca ccaccaccac cactga                                756
```

```
<210> SEQ ID NO 28
<211> LENGTH: 251
<212> TYPE: PRT
<213> ORGANISM: Artificial
<220> FEATURE:
<223> OTHER INFORMATION: Protein sequence of polyhistidine tagged
      scFv-SSPG1d-peptide

<400> SEQUENCE: 28

Met Asp Ile Val Leu Thr Gln Ser Pro Ala Ile Met Ser Ala Ser Pro
1               5                   10                  15

Gly Glu Lys Val Thr Met Thr Cys Ser Ala Ser Ser Ser Val Ser Tyr
            20                  25                  30

Met His Trp Tyr Gln Gln Lys Ser Ser Thr Ser Pro Lys Leu Trp Ile
        35                  40                  45

Tyr Asp Thr Ser Lys Leu Ala Ser Gly Val Pro Gly Arg Phe Ser Gly
    50                  55                  60

Ser Gly Ser Gly Asn Ser Tyr Ser Leu Thr Ile Ser Ser Met Glu Ala
65                  70                  75                  80

Glu Asp Val Ala Thr Tyr Tyr Cys Phe Gln Gly Ser Gly Tyr Pro Leu
                85                  90                  95

Thr Phe Gly Ala Gly Thr Lys Leu Glu Ile Lys Arg Gly Ala Gly Gly
            100                 105                 110

Ser Gly Gly Gly Gly Ser Gly Gly Gly Ser Gly Gly Gly Gly Ser
        115                 120                 125

Gln Val Gln Leu Gln Gln Ser Gly Ala Glu Leu Val Arg Pro Gly Ser
    130                 135                 140

Ser Val Lys Ile Ser Cys Lys Ala Ser Gly Tyr Ala Phe Ser Asn Tyr
145                 150                 155                 160

Trp Met Asn Trp Val Lys Gln Arg Pro Gly Gln Gly Leu Glu Trp Ile
                165                 170                 175

Gly Gln Ile Tyr Pro Gly Tyr Gly Asp Ala Lys Tyr Asn Gly Lys Phe
            180                 185                 190

Lys Gly Lys Ala Thr Leu Thr Ala Asp Ile Ser Ser Ser Thr Ala Tyr
        195                 200                 205

Met Gln Leu Ser Ser Leu Thr Ser Glu Asp Ser Ala Val Tyr Phe Cys
    210                 215                 220

Ala Arg Ser Ser Tyr Glu Ala Asn Trp Gly Gln Gly Thr Leu Val Thr
225                 230                 235                 240

Val Ser Ala Leu Glu His His His His His
                245                 250

<210> SEQ ID NO 29
<211> LENGTH: 774
<212> TYPE: DNA
<213> ORGANISM: Artificial
```

<220> FEATURE:
<223> OTHER INFORMATION: DNA sequence of polyhistidine tagged scFv-SSPG1d-whole protein

<400> SEQUENCE: 29

```
atggatattg tgatgaccca gtctcacaaa ttcatgtcca catcagtagg agacagggtc    60
agcatcacct gcaaggccag tcaggatgtg gtactgctg tagcctggta tcaacagaaa   120
ccagggcaat ctcctaaact actgatttac tgggcatcca cccggcacac tggagtccct   180
gatcgcttca caggcagtgg atctgggaca gatttcactc tcaccattag caatgtgcag   240
tctgaagact tggcagatta tttctgtcag caatatagca gctatcctcg acgttcggt   300
ggaggcacca agctggaaat caaacgtggt ggtggtggtt ctggtggtgg tggttctggc   360
ggcggcggct ccgtggtggt ggatccgag gtgcagcttc agcagtctgg ggcagacctt   420
gtgaggtcag gggcctcagt caagttgtcc tgcacagctt ctggcttcaa cattaaagac   480
tactatatcc actgggtgaa gcagaggcct gaacagggcc tggcgtggat tggatggatt   540
gatcctgaga tggtgatac tgaatatgcc ccgaagttcc aggacaaggc cactttgact   600
gcagacacat cttccaatac agcctacctg cagctcagca gcctgacatc tgaggacact   660
gccgtctatt actgtaatgc atgggctggg acgtcagggg cctggtttgc ttactggggc   720
caagggactc tggtcactgt ctctgcgctc gagcaccacc accaccacca ctga         774
```

<210> SEQ ID NO 30
<211> LENGTH: 257
<212> TYPE: PRT
<213> ORGANISM: Artificial
<220> FEATURE:
<223> OTHER INFORMATION: Protein sequence of polyhistidine tagged scFv-SSPG1d-whole protein

<400> SEQUENCE: 30

```
Met Asp Ile Val Met Thr Gln Ser His Lys Phe Met Ser Thr Ser Val
  1               5                  10                  15

Gly Asp Arg Val Ser Ile Thr Cys Lys Ala Ser Gln Asp Val Gly Thr
             20                  25                  30

Ala Val Ala Trp Tyr Gln Gln Lys Pro Gly Gln Ser Pro Lys Leu Leu
         35                  40                  45

Ile Tyr Trp Ala Ser Thr Arg His Thr Gly Val Pro Asp Arg Phe Thr
     50                  55                  60

Gly Ser Gly Ser Gly Thr Asp Phe Thr Leu Thr Ile Ser Asn Val Gln
 65                  70                  75                  80

Ser Glu Asp Leu Ala Asp Tyr Phe Cys Gln Gln Tyr Ser Ser Tyr Pro
                 85                  90                  95

Arg Thr Phe Gly Gly Gly Thr Lys Leu Glu Ile Lys Arg Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Gln Gln Ser Gly Ala Asp Leu Val Arg Ser Gly
    130                 135                 140

Ala Ser Val Lys Leu Ser Cys Thr Ala Ser Gly Phe Asn Ile Lys Asp
145                 150                 155                 160

Tyr Tyr Ile His Trp Val Lys Gln Arg Pro Glu Gln Gly Leu Ala Trp
                165                 170                 175

Ile Gly Trp Ile Asp Pro Glu Asn Gly Asp Thr Glu Tyr Ala Pro Lys
            180                 185                 190
```

Phe Gln Asp Lys Ala Thr Leu Thr Ala Asp Thr Ser Ser Asn Thr Ala
    195                 200                 205

Tyr Leu Gln Leu Ser Ser Leu Thr Ser Glu Asp Thr Ala Val Tyr Tyr
    210                 215                 220

Cys Asn Ala Trp Ala Gly Thr Ser Gly Ala Trp Phe Ala Tyr Trp Gly
225                 230                 235                 240

Gln Gly Thr Leu Val Thr Val Ser Ala Leu Glu His His His His
            245                 250                 255

His

<210> SEQ ID NO 31
<211> LENGTH: 768
<212> TYPE: DNA
<213> ORGANISM: Artificial
<220> FEATURE:
<223> OTHER INFORMATION: DNA sequence of polyhistidine tagged
      scFv-mycelia (monomer)

<400> SEQUENCE: 31
atggatattg ttctctccca gtctccaaca atcatgtctg catctccagg ggagaaggtc    60
accatgacct gcagtgccag ctcaagtgta agttacatgc actggtacca gcagaagtca   120
ggcacctccc ccaaaagatg gatttatgac acatccaaac tggcttctgg agtccctgct   180
cgcttcagtg gcagtgggtc tgggacccct accctctca caatcagcag catggaggct   240
gaagatgctg ccacttatta ctgcctgcag tggagtagta acccgtggac gttcggtgga   300
ggcaccaagc tggagctgaa acgtggtggt ggtggttctg gtggtggtgg ttctggcggc   360
ggcggctccg gtggtggtgg atcccaggtg cagctgaagc aatctggggc tgaactggca   420
aaacctgggg cctcagtgaa gatgtcctgc aaggcttctg gctacacctt tactagctac   480
tggatgcact gggtaaaaca gaggcctgga cagggtctgg aatggattgg atacattaat   540
cctagcactg gttatactga gtacaatcag aagttcaagg acaaggccac attgactgca   600
gacaaatcct ccagcacagc ctacatgcaa ctgagcagcc tgacatctga ggactctgca   660
gtctattact gtgcaagaaa gttctatggt aacttcccta tggactactg gggtcaagga   720
acctcagtca ccgtctcctc gctcgagcac caccaccacc accactga              768

<210> SEQ ID NO 32
<211> LENGTH: 255
<212> TYPE: PRT
<213> ORGANISM: Artificial
<220> FEATURE:
<223> OTHER INFORMATION: Protein sequence of polyhistidine tagged
      scFv-mycelia (monomer)

<400> SEQUENCE: 32

Met Asp Ile Val Leu Ser Gln Ser Pro Thr Ile Met Ser Ala Ser Pro
1               5                   10                  15

Gly Glu Lys Val Thr Met Thr Cys Ser Ala Ser Ser Val Ser Tyr
            20                  25                  30

Met His Trp Tyr Gln Gln Lys Ser Gly Thr Ser Pro Lys Arg Trp Ile
        35                  40                  45

Tyr Asp Thr Ser Lys Leu Ala Ser Gly Val Pro Ala Arg Phe Ser Gly
    50                  55                  60

Ser Gly Ser Gly Thr Pro Tyr Pro Leu Thr Ile Ser Ser Met Glu Ala
65                  70                  75                  80

Glu Asp Ala Ala Thr Tyr Tyr Cys Leu Gln Trp Ser Ser Asn Pro Trp
                85                  90                  95

```
Thr Phe Gly Gly Gly Thr Lys Leu Glu Leu Lys Arg Gly Gly Gly
                100                 105                 110
Ser Gly Gly Gly Gly Ser Gly Gly Gly Ser Gly Gly Gly Gly Ser
            115                 120                 125
Gln Val Gln Leu Lys Gln Ser Gly Ala Glu Leu Ala Lys Pro Gly Ala
130                 135                 140
Ser Val Lys Met Ser Cys Lys Ala Ser Gly Tyr Thr Phe Thr Ser Tyr
145                 150                 155                 160
Trp Met His Val Lys Gln Arg Pro Gly Gln Gly Leu Glu Trp Ile
                165                 170                 175
Gly Tyr Ile Asn Pro Ser Thr Gly Tyr Thr Glu Tyr Asn Gln Lys Phe
                180                 185                 190
Lys Asp Lys Ala Thr Leu Thr Ala Asp Lys Ser Ser Ser Thr Ala Tyr
            195                 200                 205
Met Gln Leu Ser Ser Leu Thr Ser Glu Asp Ser Ala Val Tyr Tyr Cys
        210                 215                 220
Ala Arg Lys Phe Tyr Gly Asn Phe Pro Met Asp Tyr Trp Gly Gln Gly
225                 230                 235                 240
Thr Ser Val Thr Val Ser Ser Leu Glu His His His His His
                245                 250                 255

<210> SEQ ID NO 33
<211> LENGTH: 1542
<212> TYPE: DNA
<213> ORGANISM: Artificial
<220> FEATURE:
<223> OTHER INFORMATION: DNA sequence of polyhistidine tagged
      scFv-mycelia (dimer)

<400> SEQUENCE: 33
atggatattg ttctctccca gtctccaaca atcatgtctg catctccagg ggagaaggtc      60
accatgacct gcagtgccag ctcaagtgta agttacatgc actggtacca gcagaagtca     120
ggcacctccc ccaaaagatg gatttatgac acatccaaac tggcttctgg agtccctgct     180
cgcttcagtg gcagtgggtc tgggaccct taccctctca caatcagcag catgaggct      240
gaagatgctg ccacttatta ctgcctgcag tggagtagta cccgtggac gttcggtgga     300
ggcaccaagc tggagctgaa acgtggtggt ggtggttctg gtggtggtgg ttctggcggc    360
ggcggctccg gtggtggtgg atcccaggtg cagctgaagc aatctggggc tgaactggca    420
aaacctgggg cctcagtgaa gatgtcctgc aaggcttctg gctacacctt tactagctac    480
tggatgcact gggtaaaaca gaggcctgga cagggtctgg aatggattgg atacattaat    540
cctagcactg gttatactga gtacaatcag aagttcaagg acaaggccac attgactgca    600
gacaaatcct ccagcacagc ctacatgcaa ctgagcagcc tgacatctga ggactctgca    660
gtctattact gtgcaagaaa gttctatggt aacttcccta tggactactg ggtcaagga     720
acctcagtca ccgtctcctc gggaggagga ggatcaggag gaggaggatc acatatggat    780
attgttctct cccagtctcc aacaatcatg tctgcatctc aggggagaa ggtcaccatg    840
acctgcagtc cagctcaag tgtaagttac atgcactggt accagcagaa gtcaggcacc    900
tcccccaaaa gatggattta tgacacatcc aaactggctt ctggagtccc tgctcgcttc    960
agtggcagtg ggtctgggac cccttaccct ctcacaatca gcagcatgga ggctgaagat    1020
gctgccactt attactgcct gcagtggagt agtaacccgt ggacgttcgg tggaggcacc    1080
aagctggagc tgaaacgtgg tggtggtggt tctggtggtg gtggttctgg cggcggcggc    1140
tccggtggtg gtggatccca ggtgcagctg aagcaatctg gggctgaact ggcaaaacct    1200
```

-continued

```
ggggcctcag tgaagatgtc ctgcaaggct tctggctaca ccttactag ctactggatg      1260 cactgggtaa acagaggcc tggacagggt ctggaatgga ttggatacat taatcctagc      1320
actggttata ctgagtacaa tcagaagttc aaggacaagg ccacattgac tgcagacaaa    1380
tcctccagca cagcctacat gcaactgagc agcctgacat ctgaggactc tgcagtctat    1440
tactgtgcaa gaaagttcta tggtaacttc cctatggact actggggtca aggaacctca    1500
gtcaccgtct cctcgctcga gcaccaccac caccaccact ga                        1542

<210> SEQ ID NO 34
<211> LENGTH: 513
<212> TYPE: PRT
<213> ORGANISM: Artificial
<220> FEATURE:
<223> OTHER INFORMATION: Protein sequence of polyhistidine tagged
      scFv-mycelia (dimer)

<400> SEQUENCE: 34

Met Asp Ile Val Leu Ser Gln Ser Pro Thr Ile Met Ser Ala Ser Pro
1               5                   10                  15

Gly Glu Lys Val Thr Met Thr Cys Ser Ala Ser Ser Ser Val Ser Tyr
            20                  25                  30

Met His Trp Tyr Gln Gln Lys Ser Gly Thr Ser Pro Lys Arg Trp Ile
        35                  40                  45

Tyr Asp Thr Ser Lys Leu Ala Ser Gly Val Pro Ala Arg Phe Ser Gly
    50                  55                  60

Ser Gly Ser Gly Thr Pro Tyr Pro Leu Thr Ile Ser Ser Met Glu Ala
65                  70                  75                  80

Glu Asp Ala Ala Thr Tyr Tyr Cys Leu Gln Trp Ser Ser Asn Pro Trp
                85                  90                  95

Thr Phe Gly Gly Gly Thr Lys Leu Glu Leu Lys Arg Gly Gly Gly Gly
            100                 105                 110

Ser Gly Gly Gly Gly Ser Gly Gly Gly Ser Gly Gly Gly Gly Ser
        115                 120                 125

Gln Val Gln Leu Lys Gln Ser Gly Ala Glu Leu Ala Lys Pro Gly Ala
    130                 135                 140

Ser Val Lys Met Ser Cys Lys Ala Ser Gly Tyr Thr Phe Thr Ser Tyr
145                 150                 155                 160

Trp Met His Trp Val Lys Gln Arg Pro Gly Gln Gly Leu Glu Trp Ile
                165                 170                 175

Gly Tyr Ile Asn Pro Ser Thr Gly Tyr Thr Glu Tyr Asn Gln Lys Phe
            180                 185                 190

Lys Asp Lys Ala Thr Leu Thr Ala Asp Lys Ser Ser Ser Thr Ala Tyr
        195                 200                 205

Met Gln Leu Ser Ser Leu Thr Ser Glu Asp Ser Ala Val Tyr Tyr Cys
    210                 215                 220

Ala Arg Lys Phe Tyr Gly Asn Phe Pro Met Asp Tyr Trp Gly Gln Gly
225                 230                 235                 240

Thr Ser Val Thr Val Ser Ser Gly Gly Gly Ser Gly Gly Gly Gly
                245                 250                 255

Ser His Met Asp Ile Val Leu Ser Gln Ser Pro Thr Ile Met Ser Ala
            260                 265                 270

Ser Pro Gly Glu Lys Val Thr Met Thr Cys Ser Ala Ser Ser Ser Val
        275                 280                 285

Ser Tyr Met His Trp Tyr Gln Gln Lys Ser Gly Thr Ser Pro Lys Arg
    290                 295                 300
```

```
Trp Ile Tyr Asp Thr Ser Lys Leu Ala Ser Gly Val Pro Ala Arg Phe
305                 310                 315                 320

Ser Gly Ser Gly Ser Gly Thr Pro Tyr Pro Leu Thr Ile Ser Ser Met
            325                 330                 335

Glu Ala Glu Asp Ala Ala Thr Tyr Tyr Cys Leu Gln Trp Ser Ser Asn
        340                 345                 350

Pro Trp Thr Phe Gly Gly Gly Thr Lys Leu Glu Leu Lys Arg Gly Gly
            355                 360                 365

Gly Gly Ser Gly Gly Gly Gly Ser Gly Gly Gly Gly Ser Gly Gly Gly
    370                 375                 380

Gly Ser Gln Val Gln Leu Lys Gln Ser Gly Ala Glu Leu Ala Lys Pro
385                 390                 395                 400

Gly Ala Ser Val Lys Met Ser Cys Lys Ala Ser Gly Tyr Thr Phe Thr
                405                 410                 415

Ser Tyr Trp Met His Trp Val Lys Gln Arg Pro Gly Gln Gly Leu Glu
            420                 425                 430

Trp Ile Gly Tyr Ile Asn Pro Ser Thr Gly Tyr Thr Glu Tyr Asn Gln
        435                 440                 445

Lys Phe Lys Asp Lys Ala Thr Leu Thr Ala Asp Lys Ser Ser Ser Thr
450                 455                 460

Ala Tyr Met Gln Leu Ser Ser Leu Thr Ser Glu Asp Ser Ala Val Tyr
465                 470                 475                 480

Tyr Cys Ala Arg Lys Phe Tyr Gly Asn Phe Pro Met Asp Tyr Trp Gly
                485                 490                 495

Gln Gly Thr Ser Val Thr Val Ser Ser Leu Glu His His His His His
            500                 505                 510

His
```

<210> SEQ ID NO 35
<211> LENGTH: 951
<212> TYPE: DNA
<213> ORGANISM: Artificial
<220> FEATURE:
<223> OTHER INFORMATION: DNA sequence of polyhistidine tagged
      scFv-defensin (partial)

<400> SEQUENCE: 35

```
atgcagaagt tgtgcgaaag gccaagtggg acatggtcag gagtctgtgg aaacaataac      60
gcatgcaaga tcagtgcat taaccttgag aaagcacgac atggatcttg caactatgtc     120
ttcccagctc acaagtgtat ctgctacttt ccttgtggtg gtggtggttc tggcggcggc     180
ggctccgata ttgttctctc ccagtctcca acaatcatgt ctgcatctcc aggggagaag     240
gtcaccatga cctgcagtgc cagctcaagt gtaagttaca tgcactggta ccagcagaag     300
tcaggcacct cccccaaaag atggatttat gacacatcca aactggcttc tggagtccct     360
gctcgcttca gtggcagtgg gtctgggacc ccttaccctc tcacaatcag cagcatggag     420
gctgaagatg ctgccactta ttactgcctg cagtggagta gtaacccgtg gacgttcggt     480
ggaggcacca agctggagct gaaacgtggt ggtggtggtt ctggtggtgg tggttctggc     540
ggcggcggct ccggtggtgg tggatcccag gtgcagctga agcaatctgg ggctgaactg     600
gcaaaacctg gggcctcagt gaagatgtcc tgcaaggctt ctggctacac ctttactagc     660
tactggatgc actgggtaaa acagaggcct ggacagggtc tggaatggat tggatacatt     720
aatcctagca ctggttatac tgagtacaat cagaagttca aggacaaggc cacattgact     780
gcagacaaat cctccagcac agcctacatg caactgagca gcctgacatc tgaggactct     840
```

```
gcagtctatt actgtgcaag aaagttctat ggtaacttcc ctatggacta ctggggtcaa    900
ggaacctcag tcaccgtctc ctcgctcgag caccaccacc accaccactg a             951
```

<210> SEQ ID NO 36
<211> LENGTH: 316
<212> TYPE: PRT
<213> ORGANISM: Artificial
<220> FEATURE:
<223> OTHER INFORMATION: Protein sequence of polyhistidine tagged
      scFv-defensin (partial)

<400> SEQUENCE: 36

```
Met Gln Lys Leu Cys Glu Arg Pro Ser Gly Thr Trp Ser Gly Val Cys
1               5                   10                  15

Gly Asn Asn Ala Cys Lys Asn Gln Cys Ile Asn Leu Glu Lys Ala
            20                  25                  30

Arg His Gly Ser Cys Asn Tyr Val Phe Pro Ala His Lys Cys Ile Cys
        35                  40                  45

Tyr Phe Pro Cys Gly Gly Gly Ser Gly Gly Gly Ser Asp Ile
    50                  55                  60

Val Leu Ser Gln Ser Pro Thr Ile Met Ser Ala Ser Pro Gly Glu Lys
65                  70                  75                  80

Val Thr Met Thr Cys Ser Ala Ser Ser Val Ser Tyr Met His Trp
                85                  90                  95

Tyr Gln Gln Lys Ser Gly Thr Ser Pro Lys Arg Trp Ile Tyr Asp Thr
                100                 105                 110

Ser Lys Leu Ala Ser Gly Val Pro Ala Arg Phe Ser Gly Ser Gly Ser
            115                 120                 125

Gly Thr Pro Tyr Pro Leu Thr Ile Ser Ser Met Glu Ala Glu Asp Ala
        130                 135                 140

Ala Thr Tyr Tyr Cys Leu Gln Trp Ser Ser Asn Pro Trp Thr Phe Gly
145                 150                 155                 160

Gly Gly Thr Lys Leu Glu Leu Lys Arg Gly Gly Gly Ser Gly Gly
                165                 170                 175

Gly Gly Ser Gly Gly Gly Gly Ser Gly Gly Gly Ser Gln Val Gln
            180                 185                 190

Leu Lys Gln Ser Gly Ala Glu Leu Ala Lys Pro Gly Ala Ser Val Lys
        195                 200                 205

Met Ser Cys Lys Ala Ser Gly Tyr Thr Phe Thr Ser Tyr Trp Met His
210                 215                 220

Trp Val Lys Gln Arg Pro Gly Gln Gly Leu Glu Trp Ile Gly Tyr Ile
225                 230                 235                 240

Asn Pro Ser Thr Gly Tyr Thr Glu Tyr Asn Gln Lys Phe Lys Asp Lys
                245                 250                 255

Ala Thr Leu Thr Ala Asp Lys Ser Ser Thr Ala Tyr Met Gln Leu
            260                 265                 270

Ser Ser Leu Thr Ser Glu Asp Ser Ala Val Tyr Tyr Cys Ala Arg Lys
        275                 280                 285

Phe Tyr Gly Asn Phe Pro Met Asp Tyr Trp Gly Gln Gly Thr Ser Val
    290                 295                 300

Thr Val Ser Ser Leu Glu His His His His His
305                 310                 315
```

<210> SEQ ID NO 37
<211> LENGTH: 1035
<212> TYPE: DNA
<213> ORGANISM: Artificial
<220> FEATURE:
<223> OTHER INFORMATION: DNA sequence of polyhistidine tagged
      scFv-defensin (full)

<400> SEQUENCE: 37

```
atggctaagt tgcgtccat catcgcactt cttttgctg ctcttgttct ttttgctgct      60
ttcgaagcac caacaatggt ggaagcacag aagttgtgcg aaaggccaag tgggacatgg    120
tcaggagtct gtggaaacaa taacgcatgc aagaatcagt gcattaacct tgagaaagca    180
cgacatggat cttgcaacta tgtcttccca gctcacaagt gtatctgcta ctttccttgt    240
ggtggtggtg gttctggcgg cggcggctcc gatattgttc tctcccagtc tccaacaatc    300
atgtctgcat ctccagggga aaggtcacc atgacctgca gtgccagctc aagtgtaagt     360
tacatgcact ggtaccagca gaagtcaggc acctccccca aaagatggat ttatgacaca    420
tccaaactgg cttctggagt ccctgctcgc ttcagtggca gtgggtctgg gacccccttac   480
cctctcacaa tcagcagcat ggaggctgaa gatgctgcca cttattactg cctgcagtgg    540
agtagtaacc cgtggacgtt cggtggaggc accaagctgg agctgaaacg tggtggtggt    600
ggttctggtg gtggtggttc tggcggcggc ggctccggtg gtggtggatc ccaggtgcag    660
ctgaagcaat ctggggctga actggcaaaa cctggggcct cagtgaagat gtcctgcaag    720
gcttctggct acacctttac tagctactgg atgcactggg taaaacagag gcctggacag    780
ggtctggaat ggattggata cattaatcct agcactggtt atactgagta caatcagaag    840
ttcaaggaca aggccacatt gactgcagac aaatcctcca gcacagccta catgcaactg    900
agcagcctga catctgagga ctctgcagtc tattactgtg caagaaagtt ctatggtaac    960
ttccctatgg actactgggg tcaaggaacc tcagtcaccg tctcctcgct cgagcaccac   1020
caccaccacc actga                                                  1035
```

<210> SEQ ID NO 38
<211> LENGTH: 344
<212> TYPE: PRT
<213> ORGANISM: Artificial
<220> FEATURE:
<223> OTHER INFORMATION: Protein sequence of polyhistidine tagged
      scFv-defensin (full)

<400> SEQUENCE: 38

```
Met Ala Lys Phe Ala Ser Ile Ile Ala Leu Leu Phe Ala Ala Leu Val
1               5                   10                  15

Leu Phe Ala Ala Phe Glu Ala Pro Thr Met Val Glu Ala Gln Lys Leu
            20                  25                  30

Cys Glu Arg Pro Ser Gly Thr Trp Ser Gly Val Cys Gly Asn Asn Asn
        35                  40                  45

Ala Cys Lys Asn Gln Cys Ile Asn Leu Glu Lys Ala Arg His Gly Ser
    50                  55                  60

Cys Asn Tyr Val Phe Pro Ala His Lys Cys Ile Cys Tyr Phe Pro Cys
65                  70                  75                  80

Gly Gly Gly Gly Ser Gly Gly Gly Gly Ser Asp Ile Val Leu Ser Gln
                85                  90                  95

Ser Pro Thr Ile Met Ser Ala Ser Pro Gly Glu Lys Val Thr Met Thr
            100                 105                 110

Cys Ser Ala Ser Ser Ser Val Ser Tyr Met His Trp Tyr Gln Gln Lys
        115                 120                 125

Ser Gly Thr Ser Pro Lys Arg Trp Ile Tyr Asp Thr Ser Lys Leu Ala
    130                 135                 140
```

```
Ser Gly Val Pro Ala Arg Phe Ser Gly Ser Gly Ser Gly Thr Pro Tyr
145                 150                 155                 160

Pro Leu Thr Ile Ser Ser Met Glu Ala Glu Asp Ala Ala Thr Tyr Tyr
            165                 170                 175

Cys Leu Gln Trp Ser Ser Asn Pro Trp Thr Phe Gly Gly Gly Thr Lys
        180                 185                 190

Leu Glu Leu Lys Arg Gly Gly Gly Ser Gly Gly Gly Gly Ser Gly
    195                 200                 205

Gly Gly Ser Gly Gly Gly Ser Gln Val Gln Leu Lys Gln Ser
210                 215                 220

Gly Ala Glu Leu Ala Lys Pro Gly Ala Ser Val Lys Met Ser Cys Lys
225                 230                 235                 240

Ala Ser Gly Tyr Thr Phe Thr Ser Tyr Trp Met His Trp Val Lys Gln
            245                 250                 255

Arg Pro Gly Gln Gly Leu Glu Trp Ile Gly Tyr Ile Asn Pro Ser Thr
        260                 265                 270

Gly Tyr Thr Glu Tyr Asn Gln Lys Phe Lys Asp Lys Ala Thr Leu Thr
    275                 280                 285

Ala Asp Lys Ser Ser Thr Ala Tyr Met Gln Leu Ser Ser Leu Thr
290                 295                 300

Ser Glu Asp Ser Ala Val Tyr Tyr Cys Ala Arg Lys Phe Tyr Gly Asn
305                 310                 315                 320

Phe Pro Met Asp Tyr Trp Gly Gln Gly Thr Ser Val Thr Val Ser Ser
            325                 330                 335

Leu Glu His His His His His His
            340

<210> SEQ ID NO 39
<211> LENGTH: 1761
<212> TYPE: DNA
<213> ORGANISM: Artificial
<220> FEATURE:
<223> OTHER INFORMATION: DNA sequence of polyhistidine tagged
      scFv-chitinase

<400> SEQUENCE: 39
atgaagtctt gtctacttct ctttctcatc ttctcattc ttttatcatt ttccttagcc    60
gagcaatgtg tcgacaagc gggaggagct ctctgcccca cgtctatg ctgcagcgag    120 ttcggatggt gcggtgacac cgaagcttac tgtaagcagc ctggctgcca aagccagtgc    180
ggtggtactc ctcctggccc caccggtgat ctttcaggca tcatttcaag atctcagttc    240
gacgacatgc ttaaacatag aaatgataat gcttgtcccg ctagaggttt ctacacttat    300
gatgccttta tcaatgccgc taagtctttc cctggcttcg gcaccaccgg agacactgcc    360
acaaggaaga agaaatcgc tgccttcttt ggtcagactt cccacgagac caccggtggg    420
tgggccacag caccagacgg accatattca tggggatact gtttcaaaca agagcagaac    480
ccttcttcaa actactgttc accgagtgcc gaatggccat gcgcatctgg taaaagctac    540
tacggaagag gaccaatgca gctatcatgg aactacaact acggacagtg tggaagagcc    600
atcggatctg acttactcaa caaccctgac cttgtctcca cgatccagt gatcgctttc    660 aaagccgcga tttggttttg gatgacacct cagtctccaa aaccgtcgtg ccacgccgtg    720
atcgtcggcc agtggcagcc ttcggatgct gaccgtgccg ctgggagagt accgggttac    780
ggtgtgatta cgaatattat taacggtggt ttagagtgtg acgcggcca agacgctaga    840 gtcgcggata gaattggatt ttaccagagg tactgtaaca ttcttggagt taatcctgga    900
```

```
ggtaaccttg attgttacaa ccaaaggtcc tttgcttctg ttaacttctt ccttgacgct   960
gctattggtg gtggtggttc tggcggcggc ggctccgata ttgttctctc ccagtctcca  1020
acaatcatgt ctgcatctcc aggggagaag gtcaccatga cctgcagtgc cagctcaagt  1080
gtaagttaca tgcactggta ccagcagaag tcaggcacct cccccaaaag atggatttat  1140
gacacatcca aactggcttc tggagtccct gctcgcttca gtggcagtgg gtctgggacc  1200
ccttaccctc tcacaatcag cagcatggag gctgaagatg ctgccactta ttactgcctg  1260
cagtggagta gtaacccgtg gacgttcggt ggaggcacca agctggagct gaaacgtggt  1320
ggtggtggtt ctggtggtgg tggttctggc ggcggcggct ccggtggtgg tggatcccag  1380
gtgcagctga agcaatctgg ggctgaactg gcaaaacctg gggcctcagt gaagatgtcc  1440
tgcaaggctt ctggctacac ctttactagc tactggatgc actgggtaaa acagaggcct  1500
ggacagggtc tggaatggat tggatacatt aatcctagca ctggttatac tgagtacaat  1560
cagaagttca aggacaaggc cacattgact gcagacaaat cctccagcac agcctacatg  1620
caactgagca gcctgacatc tgaggactct gcagtctatt actgtgcaag aaagttctat  1680
ggtaacttcc ctatggacta ctggggtcaa ggaacctcag tcaccgtctc ctcgctcgag  1740
caccaccacc accaccactg a                                            1761
```

<210> SEQ ID NO 40
<211> LENGTH: 586
<212> TYPE: PRT
<213> ORGANISM: Artificial
<220> FEATURE:
<223> OTHER INFORMATION: Protein sequence of polyhistidine tagged scFv-chitinase

<400> SEQUENCE: 40

Met Lys Ser Cys Leu Leu Leu Phe Leu Ile Phe Ser Phe Leu Leu Ser
1               5                   10                  15

Phe Ser Leu Ala Glu Gln Cys Gly Arg Gln Ala Gly Gly Ala Leu Cys
            20                  25                  30

Pro Asn Gly Leu Cys Cys Ser Glu Phe Gly Trp Cys Gly Asp Thr Glu
        35                  40                  45

Ala Tyr Cys Lys Gln Pro Gly Cys Gln Ser Gln Cys Gly Gly Thr Pro
    50                  55                  60

Pro Gly Pro Thr Gly Asp Leu Ser Gly Ile Ile Ser Arg Ser Gln Phe
65                  70                  75                  80

Asp Asp Met Leu Lys His Arg Asn Asp Asn Ala Cys Pro Ala Arg Gly
                85                  90                  95

Phe Tyr Thr Tyr Asp Ala Phe Ile Asn Ala Ala Lys Ser Phe Pro Gly
            100                 105                 110

Phe Gly Thr Thr Gly Asp Thr Ala Thr Arg Lys Lys Glu Ile Ala Ala
        115                 120                 125

Phe Phe Gly Gln Thr Ser His Glu Thr Thr Gly Gly Trp Ala Thr Ala
    130                 135                 140

Pro Asp Gly Pro Tyr Ser Trp Gly Tyr Cys Phe Lys Gln Glu Gln Asn
145                 150                 155                 160

Pro Ser Ser Asn Tyr Cys Ser Pro Ser Ala Glu Trp Pro Cys Ala Ser
                165                 170                 175

Gly Lys Ser Tyr Tyr Gly Arg Gly Pro Met Gln Leu Ser Trp Asn Tyr
            180                 185                 190

Asn Tyr Gly Gln Cys Gly Arg Ala Ile Gly Ser Asp Leu Leu Asn Asn
        195                 200                 205

```
Pro Asp Leu Val Ser Asn Asp Pro Val Ile Ala Phe Lys Ala Ala Ile
    210                 215                 220
Trp Phe Trp Met Thr Pro Gln Ser Pro Lys Pro Ser Cys His Ala Val
225                 230                 235                 240
Ile Val Gly Gln Trp Gln Pro Ser Asp Ala Asp Arg Ala Ala Gly Arg
                245                 250                 255
Val Pro Gly Tyr Gly Val Ile Thr Asn Ile Ile Asn Gly Gly Leu Glu
                260                 265                 270
Cys Gly Arg Gly Gln Asp Ala Arg Val Ala Asp Arg Ile Gly Phe Tyr
            275                 280                 285
Gln Arg Tyr Cys Asn Ile Leu Gly Val Asn Pro Gly Gly Asn Leu Asp
        290                 295                 300
Cys Tyr Asn Gln Arg Ser Phe Ala Ser Val Asn Phe Phe Leu Asp Ala
305                 310                 315                 320
Ala Ile Gly Gly Gly Ser Gly Gly Gly Gly Ser Asp Ile Val Leu
                325                 330                 335
Ser Gln Ser Pro Thr Ile Met Ser Ala Ser Pro Gly Glu Lys Val Thr
            340                 345                 350
Met Thr Cys Ser Ala Ser Ser Ser Val Ser Tyr Met His Trp Tyr Gln
        355                 360                 365
Gln Lys Ser Gly Thr Ser Pro Lys Arg Trp Ile Tyr Asp Thr Ser Lys
    370                 375                 380
Leu Ala Ser Gly Val Pro Ala Arg Phe Ser Gly Ser Gly Ser Gly Thr
385                 390                 395                 400
Pro Tyr Pro Leu Thr Ile Ser Ser Met Glu Ala Glu Asp Ala Ala Thr
                405                 410                 415
Tyr Tyr Cys Leu Gln Trp Ser Ser Asn Pro Trp Thr Phe Gly Gly Gly
            420                 425                 430
Thr Lys Leu Glu Leu Lys Arg Gly Gly Gly Ser Gly Gly Gly Gly
        435                 440                 445
Ser Gly Gly Gly Gly Ser Gly Gly Gly Gly Ser Gln Val Gln Leu Lys
    450                 455                 460
Gln Ser Gly Ala Glu Leu Ala Lys Pro Gly Ala Ser Val Lys Met Ser
465                 470                 475                 480
Cys Lys Ala Ser Gly Tyr Thr Phe Thr Ser Tyr Trp Met His Trp Val
                485                 490                 495
Lys Gln Arg Pro Gly Gln Gly Leu Glu Trp Ile Gly Tyr Ile Asn Pro
            500                 505                 510
Ser Thr Gly Tyr Thr Glu Tyr Asn Gln Lys Phe Lys Asp Lys Ala Thr
        515                 520                 525
Leu Thr Ala Asp Lys Ser Ser Ser Thr Ala Tyr Met Gln Leu Ser Ser
    530                 535                 540
Leu Thr Ser Glu Asp Ser Ala Val Tyr Tyr Cys Ala Arg Lys Phe Tyr
545                 550                 555                 560
Gly Asn Phe Pro Met Asp Tyr Trp Gly Gln Gly Thr Ser Val Thr Val
                565                 570                 575
Ser Ser Leu Glu His His His His His His
            580                 585

<210> SEQ ID NO 41
<211> LENGTH: 14
<212> TYPE: PRT
<213> ORGANISM: Artificial
<220> FEATURE:
<223> OTHER INFORMATION: Peptide sequence from SSPG1d
      endopolygalacturonase
```

```
<400> SEQUENCE: 41

Asn Gly Ser Pro Thr Gly Lys Pro Thr Ser Gly Val Pro Ile
1               5                   10

<210> SEQ ID NO 42
<211> LENGTH: 14
<212> TYPE: PRT
<213> ORGANISM: Artificial
<220> FEATURE:
<223> OTHER INFORMATION: Peptide sequence from aspartyl protease

<400> SEQUENCE: 42

Met Thr Met Asp Phe Asp Ser Gly Ser Ser Asp Leu Trp Ser
1               5                   10

<210> SEQ ID NO 43
<211> LENGTH: 37
<212> TYPE: DNA
<213> ORGANISM: Artificial
<220> FEATURE:
<223> OTHER INFORMATION: primer VL back, scback

<400> SEQUENCE: 43
ttactcgcgg cccagccggc catggcggac tacaaag                          37

<210> SEQ ID NO 44
<211> LENGTH: 38
<212> TYPE: DNA
<213> ORGANISM: Artificial
<220> FEATURE:
<223> OTHER INFORMATION: primer VL back, LB1

<400> SEQUENCE: 44
gccatggcgg actacaaaga yatccagctg actcagcc                         38

<210> SEQ ID NO 45
<211> LENGTH: 38
<212> TYPE: DNA
<213> ORGANISM: Artificial
<220> FEATURE:
<223> OTHER INFORMATION: primer VL back, LB2

<400> SEQUENCE: 45
gccatggcgg actacaaaga yattgttctc wcccagtc                         38

<210> SEQ ID NO 46
<211> LENGTH: 38
<212> TYPE: DNA
<213> ORGANISM: Artificial
<220> FEATURE:
<223> OTHER INFORMATION: primer VL back, LB3

<400> SEQUENCE: 46
gccatggcgg actacaaaga yattgtgmtm actcagtc                         38

<210> SEQ ID NO 47
<211> LENGTH: 38
<212> TYPE: DNA
<213> ORGANISM: Artificial
<220> FEATURE:
<223> OTHER INFORMATION: primer VL back, LB4

<400> SEQUENCE: 47
gccatggcgg actacaaaga yattgtgytr acacagtc                         38
```

<210> SEQ ID NO 48
<211> LENGTH: 38
<212> TYPE: DNA
<213> ORGANISM: Artificial
<220> FEATURE:
<223> OTHER INFORMATION: primer VL back, LB5

<400> SEQUENCE: 48
gccatggcgg actacaaaga yattgtratg acmcagtc    38

<210> SEQ ID NO 49
<211> LENGTH: 38
<212> TYPE: DNA
<213> ORGANISM: Artificial
<220> FEATURE:
<223> OTHER INFORMATION: primer VL back, LB6

<400> SEQUENCE: 49
gccatggcgg actacaaaga yattmagatr amccagtc    38

<210> SEQ ID NO 50
<211> LENGTH: 38
<212> TYPE: DNA
<213> ORGANISM: Artificial
<220> FEATURE:
<223> OTHER INFORMATION: primer VL back, LB7

<400> SEQUENCE: 50
gccatggcgg actacaaaga yattcagatg aydcagtc    38

<210> SEQ ID NO 51
<211> LENGTH: 38
<212> TYPE: DNA
<213> ORGANISM: Artificial
<220> FEATURE:
<223> OTHER INFORMATION: primer VL back, LB8

<400> SEQUENCE: 51
gccatggcgg actacaaaga yatycagatg acacagac    38

<210> SEQ ID NO 52
<211> LENGTH: 38
<212> TYPE: DNA
<213> ORGANISM: Artificial
<220> FEATURE:
<223> OTHER INFORMATION: primer VL back, LB9

<400> SEQUENCE: 52
gccatggcgg actacaaaga yattgttctc awccagtc    38

<210> SEQ ID NO 53
<211> LENGTH: 38
<212> TYPE: DNA
<213> ORGANISM: Artificial
<220> FEATURE:
<223> OTHER INFORMATION: primer VL back, LB10

<400> SEQUENCE: 53
gccatggcgg actacaaaga yattgwgcts acccaatc    38

<210> SEQ ID NO 54
<211> LENGTH: 38
<212> TYPE: DNA
<213> ORGANISM: Artificial
<220> FEATURE:
<223> OTHER INFORMATION: primer VL back, LB11

<210> SEQ ID NO 55
<211> LENGTH: 38
<212> TYPE: DNA
<213> ORGANISM: Artificial
<220> FEATURE:
<223> OTHER INFORMATION: primer VL back, LB12

<400> SEQUENCE: 55
gccatggcgg actacaaaga yrttktgatg acccarac                          38

<210> SEQ ID NO 56
<211> LENGTH: 38
<212> TYPE: DNA
<213> ORGANISM: Artificial
<220> FEATURE:
<223> OTHER INFORMATION: primer VL back, LB13

<400> SEQUENCE: 56
gccatggcgg actacaaaga yattgtgatg acbcagkc                          38

<210> SEQ ID NO 57
<211> LENGTH: 38
<212> TYPE: DNA
<213> ORGANISM: Artificial
<220> FEATURE:
<223> OTHER INFORMATION: primer VL back, LB14

<400> SEQUENCE: 57
gccatggcgg actacaaaga yattgtgata acycagga                          38

<210> SEQ ID NO 58
<211> LENGTH: 38
<212> TYPE: DNA
<213> ORGANISM: Artificial
<220> FEATURE:
<223> OTHER INFORMATION: primer VL back, LB15

<400> SEQUENCE: 58
gccatggcgg actacaaaga yattgtgatg acccagwt                          38

<210> SEQ ID NO 59
<211> LENGTH: 38
<212> TYPE: DNA
<213> ORGANISM: Artificial
<220> FEATURE:
<223> OTHER INFORMATION: primer VL back, LB16

<400> SEQUENCE: 59
gccatggcgg actacaaaga yattgtgatg acacaacc                          38

<210> SEQ ID NO 60
<211> LENGTH: 38
<212> TYPE: DNA
<213> ORGANISM: Artificial
<220> FEATURE:
<223> OTHER INFORMATION: primer VL back, LB17

<400> SEQUENCE: 60
gccatggcgg actacaaaga yattttgctg actcagtc                          38

```
<210> SEQ ID NO 61
<211> LENGTH: 41
<212> TYPE: DNA
<213> ORGANISM: Artificial
<220> FEATURE:
<223> OTHER INFORMATION: primer VL back, LB lambda

<400> SEQUENCE: 61
gccatggcgg actacaaaga tgctgttgtg actcaggaat c                    41

<210> SEQ ID NO 62
<211> LENGTH: 65
<212> TYPE: DNA
<213> ORGANISM: Artificial
<220> FEATURE:
<223> OTHER INFORMATION: primer VL for, LF1

<400> SEQUENCE: 62
ggagccgccg ccgccagaac caccaccacc agaaccacca ccaccacgtt tgatttccag    60
cttgg                                                                65

<210> SEQ ID NO 63
<211> LENGTH: 65
<212> TYPE: DNA
<213> ORGANISM: Artificial
<220> FEATURE:
<223> OTHER INFORMATION: primer VL for, LF2

<400> SEQUENCE: 63
ggagccgccg ccgccagaac caccaccacc agaaccacca ccaccacgtt ttatttccag    60
cttgg                                                                65

<210> SEQ ID NO 64
<211> LENGTH: 65
<212> TYPE: DNA
<213> ORGANISM: Artificial
<220> FEATURE:
<223> OTHER INFORMATION: primer VL for, LF4

<400> SEQUENCE: 64
ggagccgccg ccgccagaac caccaccacc agaaccacca ccaccacgtt ttatttccaa    60
ctttg                                                                65

<210> SEQ ID NO 65
<211> LENGTH: 65
<212> TYPE: DNA
<213> ORGANISM: Artificial
<220> FEATURE:
<223> OTHER INFORMATION: primer VL for, LF5

<400> SEQUENCE: 65
ggagccgccg ccgccagaac caccaccacc agaaccacca ccaccacgtt tcagctccag    60
cttgg                                                                65

<210> SEQ ID NO 66
<211> LENGTH: 65
<212> TYPE: DNA
<213> ORGANISM: Artificial
<220> FEATURE:
<223> OTHER INFORMATION: primer VL for, LF lambda

<400> SEQUENCE: 66
ggagccgccg ccgccagaac caccaccacc agaaccacca ccaccaccta ggacagtcag    60
tttgg                                                                65
```

<210> SEQ ID NO 67
<211> LENGTH: 50
<212> TYPE: DNA
<213> ORGANISM: Artificial
<220> FEATURE:
<223> OTHER INFORMATION: primer VH back, HB1

<400> SEQUENCE: 67
ggcggcggcg gctccggtgg tggtggatcc gakgtrmagc ttcaggagtc    50

<210> SEQ ID NO 68
<211> LENGTH: 50
<212> TYPE: DNA
<213> ORGANISM: Artificial
<220> FEATURE:
<223> OTHER INFORMATION: primer VH back, HB2

<400> SEQUENCE: 68
ggcggcggcg gctccggtgg tggtggatcc gaggtbcagc tbcagcagtc    50

<210> SEQ ID NO 69
<211> LENGTH: 50
<212> TYPE: DNA
<213> ORGANISM: Artificial
<220> FEATURE:
<223> OTHER INFORMATION: primer VH back, HB3

<400> SEQUENCE: 69
ggcggcggcg gctccggtgg tggtggatcc caggtgcagc tgaagsastc    50

<210> SEQ ID NO 70
<211> LENGTH: 50
<212> TYPE: DNA
<213> ORGANISM: Artificial
<220> FEATURE:
<223> OTHER INFORMATION: primer VH back, HB4

<400> SEQUENCE: 70
ggcggcggcg gctccggtgg tggtggatcc gaggtccarc tgcaacartc    50

<210> SEQ ID NO 71
<211> LENGTH: 50
<212> TYPE: DNA
<213> ORGANISM: Artificial
<220> FEATURE:
<223> OTHER INFORMATION: primer VH back, HB5

<400> SEQUENCE: 71
ggcggcggcg gctccggtgg tggtggatcc caggtycagc tbcagcartc    50

<210> SEQ ID NO 72
<211> LENGTH: 50
<212> TYPE: DNA
<213> ORGANISM: Artificial
<220> FEATURE:
<223> OTHER INFORMATION: primer VH back, HB6

<400> SEQUENCE: 72
ggcggcggcg gctccggtgg tggtggatcc caggtycarc tgcagcagtc    50

<210> SEQ ID NO 73
<211> LENGTH: 50
<212> TYPE: DNA
<213> ORGANISM: Artificial
<220> FEATURE:
<223> OTHER INFORMATION: primer VH back, HB7

<400> SEQUENCE: 73
ggcggcggcg gctccggtgg tggtggatcc caggtccacg tgaagcagtc          50

<210> SEQ ID NO 74
<211> LENGTH: 50
<212> TYPE: DNA
<213> ORGANISM: Artificial
<220> FEATURE:
<223> OTHER INFORMATION: primer VH back, HB8

<400> SEQUENCE: 74
ggcggcggcg gctccggtgg tggtggatcc gaggtgaass tggtggaatc          50

<210> SEQ ID NO 75
<211> LENGTH: 50
<212> TYPE: DNA
<213> ORGANISM: Artificial
<220> FEATURE:
<223> OTHER INFORMATION: primer VH back, HB9

<400> SEQUENCE: 75
ggcggcggcg gctccggtgg tggtggatcc gavgtgawgy tggtggagtc          50

<210> SEQ ID NO 76
<211> LENGTH: 50
<212> TYPE: DNA
<213> ORGANISM: Artificial
<220> FEATURE:
<223> OTHER INFORMATION: primer VH back, HB10

<400> SEQUENCE: 76
ggcggcggcg gctccggtgg tggtggatcc gaggtgcags kggtggagtc          50

<210> SEQ ID NO 77
<211> LENGTH: 50
<212> TYPE: DNA
<213> ORGANISM: Artificial
<220> FEATURE:
<223> OTHER INFORMATION: primer VH back, HB11

<400> SEQUENCE: 77
ggcggcggcg gctccggtgg tggtggatcc gakgtgcamc tggtggagtc          50

<210> SEQ ID NO 78
<211> LENGTH: 50
<212> TYPE: DNA
<213> ORGANISM: Artificial
<220> FEATURE:
<223> OTHER INFORMATION: primer VH back, HB12

<400> SEQUENCE: 78
ggcggcggcg gctccggtgg tggtggatcc gaggtgaagc tgatggartc          50

<210> SEQ ID NO 79
<211> LENGTH: 50
<212> TYPE: DNA
<213> ORGANISM: Artificial
<220> FEATURE:
<223> OTHER INFORMATION: primer VH back, HB13

<400> SEQUENCE: 79
ggcggcggcg gctccggtgg tggtggatcc gaggtgcarc ttgttgagtc          50

```
<210> SEQ ID NO 80
<211> LENGTH: 50
<212> TYPE: DNA
<213> ORGANISM: Artificial
<220> FEATURE:
<223> OTHER INFORMATION: primer VH back, HB14

<400> SEQUENCE: 80
ggcggcggcg gctccggtgg tggtggatcc gargtraagc ttctcgagtc          50

<210> SEQ ID NO 81
<211> LENGTH: 50
<212> TYPE: DNA
<213> ORGANISM: Artificial
<220> FEATURE:
<223> OTHER INFORMATION: primer VH back, HB15

<400> SEQUENCE: 81
ggcggcggcg gctccggtgg tggtggatcc gaagtgaars ttgaggagtc          50

<210> SEQ ID NO 82
<211> LENGTH: 52
<212> TYPE: DNA
<213> ORGANISM: Artificial
<220> FEATURE:
<223> OTHER INFORMATION: primer VH back, HB16

<400> SEQUENCE: 82
ggcggcggcg gctccggtgg tggtggatcc caggttactc traaacwgts tg       52

<210> SEQ ID NO 83
<211> LENGTH: 50
<212> TYPE: DNA
<213> ORGANISM: Artificial
<220> FEATURE:
<223> OTHER INFORMATION: primer VH back, HB17

<400> SEQUENCE: 83
ggcggcggcg gctccggtgg tggtggatcc caggtccaac tvcagcarcc          50

<210> SEQ ID NO 84
<211> LENGTH: 50
<212> TYPE: DNA
<213> ORGANISM: Artificial
<220> FEATURE:
<223> OTHER INFORMATION: primer VH back, HB18

<400> SEQUENCE: 84
ggcggcggcg gctccggtgg tggtggatcc gatgtgaact tggaagtgtc          50

<210> SEQ ID NO 85
<211> LENGTH: 50
<212> TYPE: DNA
<213> ORGANISM: Artificial
<220> FEATURE:
<223> OTHER INFORMATION: primer VH back, HB19

<400> SEQUENCE: 85
ggcggcggcg gctccggtgg tggtggatcc gaggtgaagg tcatcgagtc          50

<210> SEQ ID NO 86
<211> LENGTH: 17
<212> TYPE: DNA
<213> ORGANISM: Artificial
<220> FEATURE:
<223> OTHER INFORMATION: primer VH for, scfor
```

```
<400> SEQUENCE: 86
ggaattcggc ccccgag                                                    17

<210> SEQ ID NO 87
<211> LENGTH: 40
<212> TYPE: DNA
<213> ORGANISM: Artificial
<220> FEATURE:
<223> OTHER INFORMATION: primer VH for, HF1

<400> SEQUENCE: 87
ggaattcggc ccccgaggcc gaggaaacgg tgaccgtggt                           40

<210> SEQ ID NO 88
<211> LENGTH: 40
<212> TYPE: DNA
<213> ORGANISM: Artificial
<220> FEATURE:
<223> OTHER INFORMATION: primer VH for, HF2

<400> SEQUENCE: 88
ggaattcggc ccccgaggcc gaggagactg tgagagtggt                           40

<210> SEQ ID NO 89
<211> LENGTH: 40
<212> TYPE: DNA
<213> ORGANISM: Artificial
<220> FEATURE:
<223> OTHER INFORMATION: primer VH for, HF3

<400> SEQUENCE: 89
ggaattcggc ccccgaggcc gcagagacag tgaccagagt                           40

<210> SEQ ID NO 90
<211> LENGTH: 40
<212> TYPE: DNA
<213> ORGANISM: Artificial
<220> FEATURE:
<223> OTHER INFORMATION: primer VH for, HF4

<400> SEQUENCE: 90
ggaattcggc ccccgaggcc gaggagacgg tgactgaggt                           40
```

RECOMBINANT ANTIBODIES TO SCLEROTINIA ANTIGENS

CROSS REFERENCE TO RELATED APPLICATIONS

The present application claims priority from U.S. Provisional Patent Application No. 60/820,626 filed on Jul. 28, 2006 and is incorporated herein in its entirety by reference.

FIELD OF THE INVENTION

The present invention relates to recombinant antibodies to *Sclerotinia* antigens.

BACKGROUND

The production of *Brassica napus*, commonly known as canola, is an important part of the overall agricultural industry of western Canada. White stem rot of canola caused by *Sclerotinia sclerotiorum* is one of the most serious fungal diseases limiting the yield of canola production in western Canada. Among the many cell wall degrading enzymes secreted by this fungus, endo-polygalacturonase (endo PG) SSPG1d and aspartyl protease are considered to be important for pathogenesis. It is known to use recombinant antibodies to engineer resistance in plants to viral as well as fungal diseases, however, no such approach has been used to target SSPG1d, aspartyl protease or the fungal mycelia to reduce the pathogenicity of this fungus.

Therefore, there is a need in the art for recombinant antibodies to *Sclerotinia* antigens, which may then be used to engineer resistance in plants to *Sclerotinia* infections.

SUMMARY OF THE INVENTION

The present invention comprises recombinant antibodies to *Sclerotinia sclerotiorum* antigens. In one aspect of the invention, the invention comprises an isolated antibody which specifically binds to a *Sclerotinia sclerotiorum* antigen, the antibody comprising a single chain variable fragment (scFv), or modified forms, subsequences or fragments thereof. In one embodiment, the antigen is selected from SSPG1d or a portion thereof, aspartyl protease or a portion thereof, or whole *Sclerotinia sclerotiorum* mycelium. In one embodiment, the antibody comprises an amino acid sequence selected from SEQ ID NO:2, SEQ ID NO:4, SEQ ID NO:6, SEQ ID NO:8, SEQ ID NO:10, SEQ ID NO:12, SEQ ID NO:14 or SEQ ID NO:16. In a further embodiment, the antibody comprises a polyhistidine tag. In another embodiment, the antibody comprises an amino acid sequence selected from SEQ ID NO:28, SEQ ID NO:30, SEQ ID NO:32, SEQ ID NO:34, SEQ ID NO:36, SEQ ID NO:38 or SEQ ID NO:40.

In another aspect, the invention provides an antibody which specifically binds to a *Sclerotinia sclerotiorum* antigen, linked to an anti-fungal polypeptide. In one embodiment, the anti-fungal protein comprises Rs-AFP1 (ATCC U18557) or Bn-Ch25 endochitinase (ATCC M95835).

Amino acid sequences which are substantially similar to the amino acid sequences described above, and which are capable of specifically binding to a *Sclerotinia sclerotiorum* antigen are within the scope of this invention.

In another aspect of the invention, the invention comprises a nucleic acid
 (a) encoding an scFv antibody described herein; or
 (b) having a nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23 or SEQ ID NO:25; or
 (c) having a nucleic acid sequence which is at least 80% homologous to one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23 or SEQ ID NO:25; or
 (d) which hybridizes to a nucleic acid sequence which encodes an scFv antibody under at least moderately stringent conditions.

In another aspect, the invention comprises a nucleic acid encoding an antibody as described herein and comprising a polyhistidine tag. In one embodiment, the nucleic acid comprises the nucleic acid sequence of SEQ ID NO:27, SEQ ID NO:29, SEQ ID NO:31, SEQ ID NO:33, SEQ ID NO:35, SEQ ID NO:37 or SEQ ID NO:39.

Nucleic acid sequences having at least 80% homology, more preferably at least 85% homology, more preferably at least 90% homology, more preferably at least 95% homology, or more preferably at least 96%, 97%, 98%, or 99% homology with any of the nucleic acid sequences described herein, and which encode polypeptides, or modified forms, subsequences or fragments thereof, capable of specifically binding to a *Sclerotinia sclerotiorum* antigen are within the scope of this invention.

In another aspect of the invention, the invention comprises an expression vector comprising a nucleic acid sequence according to any one of the nucleic acids described above in functional combination with a plant expressible promoter.

In another aspect of the invention, the invention comprises a transgenic plant, plant seed, plant tissue or plant cell transformed with the expression vector described above, wherein the plant, plant seed, plant tissue or plant cell is susceptible to *Sclerotinia sclerotiorum*. In one embodiment, the plant, seed, tissue or cell is a canola, mustard or *Arabidopsis thaliana* plant, seed, tissue or cell.

In another aspect of the invention, the invention comprises a method for producing a transgenic plant that is resistant to *Sclerotinia sclerotiorum* comprising the steps of: a) introducing into a plant seed, plant tissue or plant cell the expression vector as described above to produce a transformed plant seed, plant tissue or plant cell; and b) regenerating a transgenic plant from the transformed plant seed, transformed plant tissue or transformed plant cell, wherein the transgenic plant is resistant to *Sclerotinia sclerotiorum*. In one embodiment, the transgenic plant is a canola, mustard or *Arabidopsis thaliana* plant.

In another aspect of the invention, the invention comprises an immunoassay method to detect *Sclerotinia sclerotiorum* in a biological sample utilizing an scFv antibody which binds to *Sclerotinia sclerotiorum* antigen, comprising the steps of: (a) contacting the sample containing *Sclerotinia sclerotiorum* antigen with the antibody as described above under conditions which allow binding of the *Sclerotinia sclerotiorum* antigen to the antibody; and (b) detecting the presence of the *Sclerotinia sclerotiorum* antigen in the sample. In one embodiment, the detection step comprises performing an immunoassay such as an ELISA.

In another aspect of the invention, the invention comprises an immunoassay kit for the detection of *Sclerotinia sclerotiorum* in a biological sample, comprising an antibody as described above, and reagents for detection of specific binding of *Sclerotinia sclerotiorum* antigen to the antibody in the sample. In one embodiment, the immunoassay is an ELISA-based immunoassay.

In another aspect of the invention, the invention comprises an antibody which specifically binds to a *Sclerotinia sclerotiorum* antigen with cross-reactivity to *Botrytis cinerea*, comprising a single chain variable fragment (scFv). In one embodiment, the antibody comprises the amino acid sequence of SEQ ID NO:6.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows:

FIGS. 1A-H show DNA and amino acid sequences for (A) scFv-SSPG1d-peptide (SEQ ID NOS: 1 and 2), (B) scFv-SSPG1d-whole protein (SEQ ID NOS: 3 and 4), (C) scFv-mycelia (monomer) (SEQ ID NOS: 5 and 6), (D) scFv-mycelia (dimer) (SEQ ID NOS: 7 and 8), (E) scFv-defensin fusion (partial) (SEQ ID NOS: 9 and 10), (F) scFv-defensin fusion (full) (SEQ ID NOS: 11 and 12), (G) scFv-chitinase fusion (SEQ ID NOS: 13 and 14) and (H) scFv-aspartyl protease fusion (SEQ ID NOS: 15 and 16).

FIGS. 1I-M show DNA and amino acid sequences for (I) scFv-pAK-May 2 #6 (SEQ ID NOS: 17 and 18), (J) scFv-pAK-3 (SEQ ID NOS: 19 and 20), (K) scFv-pAK-6 (SEQ ID NOS: 21 and 22), (L) scFv-pAK-9 (SEQ ID NOS: 23 and 24) and (M) scFv-pAK-10 (SEQ ID NOS: 25 and 26).

FIGS. 2A-G shows DNA and amino acid sequences for the polyhistidine tagged (A) scFv-SSPG1d-peptide (SEQ ID NOS: 27 and 28), (B) scFv-SSPG1d-whole protein (SEQ ID NOS: 29 and 30) and (C) scFv-mycelia (monomer) (SEQ ID NOS: 31 and 32), (D) scFv-mycelia (dimer) (SEQ ID NOS: 33 and 34), (E) scFv-defensin (partial) (SEQ ID NOS: 35 and 36), (F) scFv-defensin (full) (SEQ ID NOS: 37 and 38) and (G) scFv-chitinase (SEQ ID NOS: 39 and 40).

DETAILED DESCRIPTION OF PREFERRED EMBODIMENTS

Figure 3:
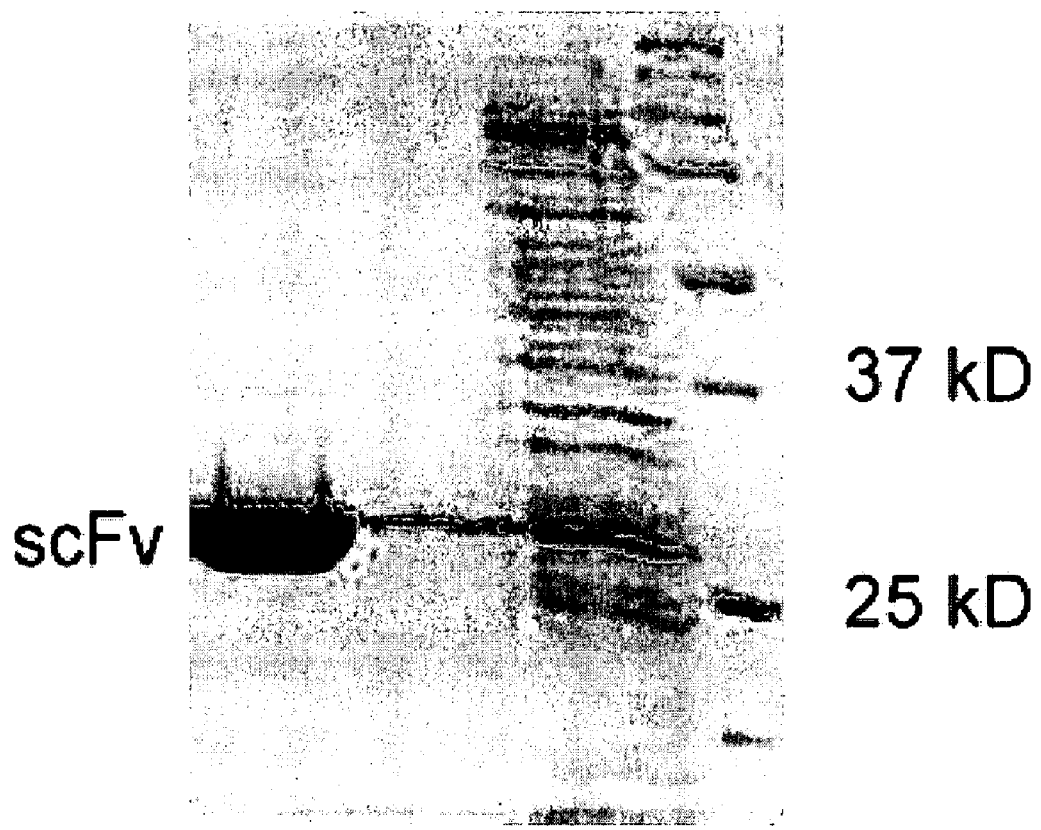
FIG. 3 shows an image of a representative 13% SDS-PAGE gel indicating purity of scFv.

The present invention relates to recombinant antibodies and recombinant antibody-antifungal protein fusions, which specifically bind to *Sclerotinia sclerotiorum* antigens, and includes nucleic acids encoding for such antibodies, and expression vectors comprising such nucleic acids. The present invention also extends to plants, plant cells and seeds transformed with such nucleic acids, and to immunoassay methods and kits using the recombinant antibodies and recombinant antibody-antifungal protein fusions for detecting *Sclerotinia sclerotiorum* antigens in a biological sample.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

A "single chain variable fragment (scFv) antibody" is a fusion of the variable regions of the heavy and light chains of immunoglobulin linked together with a short linker. This chimeric molecule retains the specificity of the original immunoglobulin, despite removal of the constant regions and the introduction of a linker peptide. Methods for producing scFv antibodies are described, for example, by Whitlow et al., (1991) In: Methods: A Companion to Methods in Enzymology 2:97; U.S. Pat. No. 4,946,778; and Pack et al., (1993) Bio/Technology 11:1271. An scFv antibody-antifungal protein fusion is a chimeric protein in which the scFv antibody is linked to a protein/peptide that has been previously identified as having anti-fungal activities. The antifungal proteins that have been used in specific embodiments described herein include Rs-AFP1 (GenBank accession number U18557) and Bn-Ch25 endochitinase (GenBank accession number M95835).

As used herein, the term "bind" or "binding" means that the scFv antibodies of the present invention have affinity for *Sclerotinia sclerotiorum* antigens. The term "specific" or "selective", when used in reference to binding, means that the binding between the scFv antibodies and *Sclerotinia sclerotiorum* antigens is such that it can be distinguished from non-specific or non-selective binding to other molecules using an assay such as ELISA, immunoprecipitation, coprecipitation, western blotting, two-hybrid assays and the like. Appropriate controls can be used to distinguish between "specific" and "non-specific" binding. For example, specific or selective binding typically has a dissociation constant ($K_D$) of less than about $1 \times 10^{-5}$ M or less than about $1 \times 10^{-6}$ M, $1 \times 10^{-7}$ M, $1 \times 10^{-8}$ M, $1 \times 10^{-9}$, or $1 \times 10^{-10}$ M. In contrast, non-specific binding typically has significantly less affinity, for example, a $K_D$ greater than $10^{-3}$ M. Thus, selective binding can be distinguished from non-selective binding by measuring dissociation constant of the antibody-antigen complex. Selective binding can also be distinguished form non-selective binding by increasing the stringency of the binding assay.

The term "significant" or "substantial" when used in reference to the binding affinity of the scFv antibodies to the *Sclerotinia sclerotiorum* antigens, means that the dissociation constant ($K_D$) of the scFv antibody—*Sclerotinia sclerotiorum* antigen complex) is not more than $10^{-3}$ M. For significant binding affinity, the $K_D$ must be less than $10^{-3}$ M, $10^{-4}$ M, $10^{-5}$ M, $10^{-6}$ M, $10^{-7}$ M, $10^{-8}$ M, etc. Typically, the $K_D$ of an antibody-antigen complex is about $10^{-5}$ M to about $10^{-6}$ M or less.

The scFv antibodies of the present invention may be produced by assembling gene fragments from antibodies that can specifically recognize antigens of interest. In a preferred embodiment, the antigens include one or more of SSPG1d peptide, whole SSPG1d, aspartyl protease peptide and whole *S. sclerotiorum* mycelium. Thus, the well-established protocol involving the immunization of mice with the target antigens and the isolation of the antibody-producing spleen cells may be utilized.

Total RNA and messenger RNA (mRNA) may then be isolated from the splenocytes and the corresponding cDNA synthesized using conventional methods. cDNA coding the variable heavy chain ($V_H$) and variable light chain ($V_L$) antibody fragments may then be linked and amplified using PCR using appropriate primers to generate full length scFv.

The PCR amplified antibody fragments may then be purified, by gel purification for example, and the scFv genes may then be inserted into plasmids using restriction endonucleases. Suitable enzymes include SfiI (New England Biolabs) and suitable plasmids may include pAK100 or pJB12 vectors. The construction of the phage display scFv library, panning and phage rescue may be performed using conventional methods, well known to those skilled in the art, including those essentially as described in Krebber et al. (1997) and Tout et al. (2001).

The recombinant antibodies produced as described above specifically bind to *Sclerotinia sclerotiorum* antigens. In one aspect of the invention, the invention comprises an isolated antibody which specifically binds to a *Sclerotinia sclerotiorum* antigen, the antibody comprising a single chain variable fragment (scFv). In one embodiment, the antigen comprises SSPG1d or a portion thereof, aspartyl protease or portion thereof, or whole *Sclerotinia sclerotiorum* mycelium. In one embodiment, the antibody comprises an amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24 or SEQ ID NO:26. In a further embodiment, the antibody comprises a polyhistidine tag. In one embodiment, the antibody comprises an amino acid sequence of SEQ ID NO:28, SEQ ID NO:30, SEQ ID NO:32, SEQ ID NO:34, SEQ ID NO:36, SEQ ID NO:38 or SEQ ID NO:40.

Nucleic acid sequences encoding the above scFv antibodies are provided. The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

In one embodiment, the nucleic acid comprises the nucleic acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23 or SEQ ID NO:25. In a further embodiment, the encoded antibody has a polyhistidine tag. In one embodiment, the nucleic acid comprises the nucleic acid sequence of SEQ ID NO:27, SEQ ID NO:29, SEQ ID NO:31, SEQ ID NO:33, SEQ ID NO:35, SEQ ID NO:37 or SEQ ID NO:39.

As described in the Examples, in one embodiment, the invention provides an antibody which binds to a *Sclerotinia sclerotiorum* antigen and a *Botrytis cinerea* antigen, comprising a single chain variable fragment (scFv). In one embodiment, the antibody comprises an amino acid sequence of SEQ ID NO:6.

The invention extends to homologous or substantially identical amino acid sequences functionally equivalent to the amino acid sequences described above. By the terms "homologous" or "substantially identical" it is meant that two amino acid sequences are at least 80% identical, more preferably are at least 85% identical, more preferably 90% identical, and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

The phrase "nucleic acid sequence encoding an scFv antibody" refer to any and all nucleic acid sequences encoding an scFv antibody which specifically binds to a *Sclerotinia sclerotiorum* antigen. Such nucleic acid sequences further include any and all nucleic acid sequences which (i) encode polypeptides that are substantially identical to the scFv amino acid sequences set forth herein; or (ii) hybridize to any nucleic acid sequences set forth herein under at least moderately stringent hybridization conditions or which would hybridize thereto under at least moderately stringent conditions but for the use of synonymous codons.

By the phrase "at least moderately stringent hybridization conditions", it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the $T_m$, which in sodium containing buffers is a function of the sodium ion concentration and temperature ($T_m$=81.5° C.−16.6 ($Log_{10}[Na^+]$)+0.41(% (G+C)−600/1), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in $T_m$, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at $T_m$ (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

In view of the foregoing, amino acid sequences having at least 80% homology, more preferably at least 85% homology, more preferably at least 90% homology, more preferably at least 95% homology, for example, 96%, 97%, 98% or 99% homology with any of the amino acid sequences described above, and which are capable of specifically binding to a *Sclerotinia sclerotiorum* antigen are within the scope of this invention.

In addition, the invention may comprise a subsequence or fragment of an scFv antibody which specifically binds to a *Sclerotinia sclerotiorum* antigen. As used herein, the term "subsequence" or "fragment" means a portion of the full length molecule. For example, a subsequence of an antibody is at least one amino acid less in length than full length antibody having intact heavy and light chain sequence (e.g. one or more internal or terminal amino acid deletions from either amino or carboxy-termini). Subsequences therefore can be any length up to the full length molecule. Subsequences include portions which retain at least part of the function or activity of a full length antibody or a reference antibody sequence. For example, an antibody subsequence will retain the ability to selectively bind to an antigen, even though the binding affinity of the subsequence may be greater or less than the binding affinity of the full length reference antibody. Fragments are known in the art and described, for example, in Hudson, Curr. Opin. Biotechnol. 9:395 (1998).

Pepsin or papain digestion of whole antibodies can be used to generate subsequences. For example, Fab can be produced by digestion of a whole antibody with the enzyme papain, to yield a fragment consisting of an intact light chain and a portion of a heavy chain. (Fab')$_2$ can be produced by treating a whole antibody with the enzyme pepsin, without subsequent reduction. An Fab' antibody fragment can be produced from (Fab')$_2$ by reduction with a thiol reducing agent, which yields a molecule consisting of an intact light chain and a portion of a heavy chain. Two Fab' fragments are produced per antibody molecule treated in this manner.

Other methods of producing antibody subsequences, such as separation of heavy chains to form monovalent light-heavy chain fragments, further cleavage of fragments, or other enzymatic, chemical, or genetic techniques may also be used, provided that the subsequences have a function or activity, e.g., bind to the antigen to which the intact antibody binds.

Modified forms of the scFv antibodies of the present invention also include derivatized sequences, for example, amino acids in which free amino groups form amine hydrochlorides, p-toluene sulfonyl groups, carbobenzoxy groups; the free carboxy groups from salts, methyl and ethyl esters; free hydroxyl groups that form O-acyl or O-alkyl derivatives, as well as naturally occurring amino acid derivatives, for example, 4-hydroxyproline, for proline, 5-hydroxylysine for lysine, homoserine for serine, ornithine for lysine, etc. Modifications can be produced using any of a variety of methods well known in the art (e.g., PCR based sited-directed, deletion and insertion mutagenesis, chemical modification and mutagenesis, cross-linking, etc.).

ScFv antibodies of the invention can be either joined directly or indirectly through covalent or non-covalent binding, e.g. via a multimerization domain, to produce multimers. Specific examples of domains that confer multimer formation include coiled-coil (e.g., leucine zipper structures) and alpha-helical protein sequences. Sequences that mediate protein-protein binding via Van der Waals' forces, hydrogen bonding or charge-charge bonds are also contemplated as multimerization domains. The antibodies of the invention therefore also include multimers. A multimer can be a dimer, trimer, tetramer or other higher order oligomer. Multimers can be combinations of the same antibodies (homo-oligomers) or different antibodies (hetero-oligomers), the different antibodies being human, humanized or non-human.

ScFv antibodies of the invention can be modified to include one or more functions or activities in addition to binding a particular antigen. For example, an antibody can include a region that binds to a different antigen, or have a function distinct from antigen binding. Such modified antibodies are referred to herein as "multifunctional antibodies," and include, for example, multispecific (e.g., bispecific, trispecific, tetraspecific, etc.) antibodies. The term "multispecific" refers to an antibody that binds to two or more different antigenic epitopes. The different epitopes may be present on the same antigen or different antigens. For example, a multi-specific antibody oligomer comprises a mixture of two or more antibodies each having different epitope binding specificity and which form a multimer. The different epitopes may be expressed by the same or a different cell.

The term "multifunctional" means that the composition referred to has two or more activities or functions. Particular non-limiting examples include, for example, antigen binding, enzyme activity, ligand or receptor binding (substrates, agonists and antagonists), detection, purification, and toxicity.

The term "detectable label" refers to a molecule that can be conjugated to another molecule so as to enable detection of the conjugated molecule. Examples of detectable labels include chelators, photoactive agents, radionuclides (alpha, beta and gamma emitters), fluorescent agents and paramagnetic ions. The term "tag" refers to a molecule conjugated to another that allows detection or purification. Specific examples of tags include immunoglobulins, T7, polyhistidine tags, glutathione-S-transferase, a chitin-binding tag, calmodulin-binding tag, myc tag, and a Xpress epitope (detectable by anti-Xpress antibody; Invitrogen, Carlsbad, Calif., USA).

An antibody that has an attached polypeptide with enzyme activity (e.g., green fluorescent protein, acetyltransferase, galactosidase, glucose oxidase, peroxidase, horseradish peroxidase (HRP), urease and alkaline phosphatase) is one particular example of a multifunctional antibody. Attached polypeptides also include apoptotic factors, differentiative factors, chemokines and cytokines (interleukins, interferons).

Additional candidate functions for multifunctional antibodies other than antigen binding include, for example, radioactive (e.g., $^3$H, $^{14}$C, $^{32}$P, $^{33}$P, $^{35}$S, $^{125}$I, $^{131}$I) and non-radioactive moieties (e.g., gold particles, colored glass or plastic polystyrene, polypropylene, or latex beads) and amino acid sequences (e.g., tags, as set forth herein) for detection.

Detectable moieties also include fluorescent compounds (e.g., fluorescein isothiocyanate, rhodamine, phycoerytherin, phycocyanin, allophycocyanin, o-phthaldehyde, fluorescamine, and commercially available fluorophores such as Alexa Fluor 350, Alexa Fluor 488, Alexa Fluor 532, Alexa Fluor 546, Alexa Fluor 568, Alexa Fluor 594, Alexa Fluor 647, and BODIPY dyes such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine and Texas Red, from Molecular Probes, Inc., Eugene, Oreg.), colloidal metals, chemiluminescent compounds (e.g., luminol, isoluminol, an aromatic acridinium ester, an imidazole, an acridinium salt and oxalate esters), bioluminescent compounds (e.g., luciferin, luciferase and aequorin), paramagnetic labels (e.g., chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III)) which can be detected by MRI, and adhesion proteins (e.g., biotin, streptavidin, avidin, and other lectins).

Additional candidate functions include cytotoxicity (e.g., bacterial cholera toxin, pertussis toxin, anthrax toxin lethal factor, *Pseudomonas* exotoxin A, diphtheria toxin, plant toxin ricin, radionuclides and cytotoxic drugs). Modified antibodies therefore also include addition of functional entities, covalently or non-covalently attached to the antibodies of the invention.

Multifunctional antibodies can be produced through chemical crosslinking of the selected molecules (which have been produced by synthetic means or by expression of nucleic acid that encode the polypeptides), via an amino acid linker sequence or through recombinant DNA technology combined with in vitro, or cellular expression of the polypeptide. Multispecific antibodies can be similarly produced through recombinant technology and expression, fusion of hybridomas (e.g., to produce quadromas) that produce antibodies with different epitopic specificities, or expression of multiple nucleic acid encoding antibody variable chains with different epitopic specificities in a single cell. The coupling of such agents can be performed using conventional methods known in the art (see, for example, R. Reisfeld and S. Sell Eds. Monoclonal Antibodies and Cancer Therapy, Alan R. Liss Inc. NY, 1985; and U.S. Pat. Nos. 5,558,852 and 5,624,659)

Nucleic acids encoding the scFv antibodies of the present invention are useful for transforming plants and conferring full or partial resistance to *Sclerotinia sclerotiorum* to those plants. Plant species of interest include, without limitation, crops used for commercial production and which are susceptible to *Sclerotinia*. Examples include *Arabidopsis thaliana*, borage or starflower (*Borago officinalis*); Brazil nut (*Betholettia excelsa*); canola (*Brassica napus*), carrot (*Daucus carota*), castor bean (*Riccinus communes*); coconut (*Cocus nucifera*); coriander (*Coriandrum sativum*); corn (*Zea mays*); cotton (*Gossypium* spp.); evening primrose (*Oenothera* spp); groundnut (*Arachis hypogaea*); jojoba (*Simmondsia chinensis*); linseed/flax (*Linum usitatissimum*); maize (*Zea mays*); mustard (*Brassica* spp. and *Sinapis alba*); oil palm (*Elaeis guineensis*); olive (*Olea europaea*); rapeseed (*Brassica* spp.); rice (*Oryza sativa*); safflower (*Carthamus tinctorius*); soybean (*Glycine max*); squash (*Cucurbita maxima*); barley (*Hordeum vulgare*); wheat (*Triticum aestivum*); duckweed (*Lemnaceae* sp.), false flax (*Camelina* sp.) and sunflower (*Helianthus annuus*).

The present invention includes recombinant expression vectors comprising the nucleic acid sequences of the present invention, wherein the expression vector is suitable for expression in a plant cell. The term "suitable for expression in a plant cell" means that the recombinant expression vector comprises a nucleic acid sequence of the present invention linked to genetic elements required to achieve expression in a plant cell. Genetic elements that may be included in the expression vector in this regard include a transcriptional termination region, one or more nucleic acid sequences encoding marker genes, one or more origins of replication and the like. In preferred embodiments, the expression vector further comprises genetic elements required for the integration of the vector or a portion thereof in the plant cell's nuclear genome, for example the T-DNA left and right border sequences which facilitate the integration into the plant's nuclear genome in embodiments of the invention in which plant cells are transformed using *Agrobacterium.*

As mentioned above, the recombinant expression vector generally comprises a transcriptional terminator which besides serving as a signal for transcription termination further may serve as a protective element capable of extending the mRNA half life (Guarneros et al., 1982, Proc. Natl. Acad. Sci. USA, 79: 238-242). The transcriptional terminator is generally from about 200 nucleotides to about 1000 nucleotides and the expression vector is prepared so that the transcriptional terminator is located 3' of the nucleic acid sequence encoding an scFv antibody. Termination sequences that may be used herein include, for example, the nopaline termination region (Bevan et al., 1983, Nucl. Acids. Res., 11: 369-385), the phaseolin terminator (van der Geest et al., 1994, Plant J. 6: 413-423), the arcelin terminator (Jaeger G D, et al., 2002, Nat. Biotechnol. 20:1265-8), the terminator for the octopine synthase genes of *Agrobacterium tumefaciens* or other similarly functioning elements. Transcriptional terminators may be obtained as described by An (An, 1987, Methods in Enzym. 153: 292).

In one embodiment, the expression vector may further comprise a marker gene. Marker genes that may be used include all genes that allow the distinction of transformed cells from non-transformed cells, including all selectable and screenable marker genes. A marker gene may be a resistance marker such as an antibiotic resistance marker against, for example, kanamycin (U.S. Pat. No. 6,174,724), ampicillin, G418, bleomycin, hygromycin or spectinomycin which allows selection of a trait by chemical means or a tolerance marker against a chemical agent, such as the normally phytotoxic sugar mannose (Negrotto et al., 2000, Plant Cell Rep. 19: 798-803). Other convenient markers that may be used herein include markers capable of conveying resistance against herbicides such as glyphosate (U.S. Pat. Nos. 4,940,935; 5,188,642), phosphinothricin (U.S. Pat. No. 5,879,903) or sulphonyl ureas (U.S. Pat. No. 5,633,437). Resistance markers, when linked in close proximity to nucleic acid sequence encoding the apolipoprotein polypeptide, may be used to maintain selection pressure on a population of plant cells or plants that have not lost the nucleic acid sequence encoding the scFV antibody. Screenable markers that may be employed to identify transformants through visual inspection include β-glucuronidase (GUS) (U.S. Pat. Nos. 5,268,463 and 5,599,670) and green fluorescent protein (GFP) (Niedz et al., 1995, Plant Cell Rep., 14: 403).

Recombinant vectors suitable for the introduction of nucleic acid sequences into plants include *Agrobacterium* and *Rhizobium* based vectors, such as the Ti and Ri plasmids, including for example pBIN19 (Bevan, Nucl. Acid. Res., 1984, 22: 8711-8721), pGKB5 (Bouchez et al., 1993, C R Acad. Sci. Paris, Life Sciences, 316:1188-1193), the pCGN series of binary vectors (McBride and Summerfelt, 1990, Plant Mol. Biol., 14:269-276) and other binary vectors (e.g. U.S. Pat. No. 4,940,838).

The recombinant expression vectors of the present invention may be prepared in accordance with methodologies well known to those skilled in the art of molecular biology. Such preparation will typically involve the bacterial species *Escherichia coli* as an intermediary cloning host. The preparation of the *E. coli* vectors as well as the plant transformation vectors may be accomplished using commonly known techniques such as restriction digestion, ligation, gelectrophoresis, DNA sequencing, the Polymerase Chain Reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13mp series of vectors, pBluescript etc. Typically, these cloning vectors contain a marker allowing selection of transformed cells. Nucleic acid sequences may be introduced in these vectors, and the vectors may be introduced in *E. coli* grown in an appropriate medium. Recombinant expression vectors may readily be recovered from cells upon harvesting and lysing of the cells. Further, general guidance with respect to the preparation of recombinant vectors may be found in, for example: Sambrook et al., Molecular Cloning, a Laboratory Manual, Cold Spring Harbor Laboratory Press, 1989, Vol. 3.

In accordance with the present invention, a nucleic acid sequence is introduced into a plant cell and the cells are grown into mature plants, wherein the plant expresses the scFv antibody.

Methodologies to introduce plant recombinant expression vectors into a plant cell, also referred to herein as "transformation", are well known to the art and typically vary depending on the plant cell that is selected. General techniques to introduce recombinant expression vectors in cells include, electroporation; chemically mediated techniques, for example $CaCl_2$ mediated nucleic acid uptake; particle bombardment (biolistics); the use of naturally infective nucleic acid sequences, for example virally derived nucleic acid sequences, or *Agrobacterium* or *Rhizobium* derived sequences, polyethylene glycol (PEG) mediated nucleic acid uptake, microinjection and the use of silicone carbide whiskers.

In preferred embodiments, a transformation methodology is selected which will allow the integration of the nucleic acid sequence in the plant cell's genome, and preferably the plant cell's nuclear genome. The use of such a methodology is preferred as it will result in the transfer of the nucleic acid sequence to progeny plants upon sexual reproduction. Transformation methods that may be used in this regard include biolistics and *Agrobacterium* mediated methods.

Transformation methodologies for dicotyledenous plant species are well known. Generally, *Agrobacterium* mediated transformation is used because of its high efficiency, as well as the general susceptibility by many, if not all, dicotyledenous plant species. *Agrobacterium* transformation generally involves the transfer of a binary vector, such as one of the hereinbefore mentioned binary vectors, comprising the chimeric nucleic acid sequence of the present invention from *E. coli* to a suitable *Agrobacterium* strain (e.g. EHA101 and LBA4404) by, for example, tri-parental mating with an *E. coli* strain carrying the recombinant binary vector and an *E. coli* strain carrying a helper plasmid capable of mobilizing the binary vector to the target *Agrobacterium* strain, or by DNA transformation of the *Agrobacterium* strain (Hofgen et al., Nucl. Acids. Res., 1988, 16:9877). Other techniques that may be used to transform dicotyledenous plant cells include biolistics (Sanford, 1988, Trends in Biotechn. 6:299-302); electroporation (Fromm et al., 1985, Proc. Natl. Acad. Sci. USA., 82:5824-5828); PEG mediated DNA uptake (Potrykus et al., 1985, Mol. Gen. Genetics, 199:169-177); microinjection (Reich et al., Bio/Techn., 1986, 4:1001-1004); and silicone carbide whiskers (Kaeppler et al., 1990, Plant Cell Rep., 9:415-418) or in planta transformation using, for example, a flower dipping methodology (Clough and Bent, 1998, Plant J., 16:735-743).

Monocotyledonous plant species may be transformed using a variety of methodologies including particle bombardment (Christou et al., 1991, Biotechn. 9:957-962; Weeks et al., Plant Physiol., 1993, 102:1077-1084; Gordon-Kamm et al., Plant Cell, 1990, 2:5603-618); PEG mediated DNA uptake (European Patents 0292 435; 0392 225) or *Agrobacterium* mediated transformation (Goto-Fumiyuki et al., 1999, Nature-Biotech. 17:282-286).

The exact plant transformation methodology may vary somewhat depending on the plant species and the plant cell type (e.g. seedling derived cell types such as hypocotyls and cotyledons or embryonic tissue) that is selected as the cell target for transformation. For example, a methodology to obtain safflower transformants is available in Baker and Dyer (Plant Cell Rep., 1996, 16:106-110). Additional plant species specific transformation protocols may be found in: Biotechnology in Agriculture and Forestry 46: Transgenic Crops I (Y. P. S. Bajaj ed.), Springer-Verlag, New York (1999), and Biotechnology in Agriculture and Forestry 47: Transgenic Crops II (Y. P. S. Bajaj ed.), Springer-Verlag, New York (2001).

Following transformation, the plant cells are grown and upon the emergence of differentiating tissue, such as shoots and roots, mature plants are regenerated. Typically a plurality of plants is regenerated. Methodologies to regenerate plants are generally plant species and cell type dependent and will be known to those skilled in the art. Further guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

In one embodiment, the invention thus provides a method for producing a transgenic plant which is more resistant to *Sclerotinia sclerotiorum* than a non-transformed plant, comprising the steps of a) introducing into a plant seed, tissue or cell the expression vector described above, and b) regenerating a transgenic plant from the transformed plant seed, tissue or cell. In one embodiment, the transgenic plant is a transformed canola or mustard plant.

The present invention is also directed to an immunoassay method using an antibody of the present invention to detect *Sclerotinia sclerotiorum* in a biological sample. The immunoassay method comprises obtaining a biological sample to be tested, exposing the sample to the antibody of the present invention, and determining whether the antibody binds to the contents of the sample. Binding of the antibody to the contents of the sample indicates that the sample contains *Sclerotinia sclerotiorum* antigen. The immunoassay method can be used as a qualitative or quantitative test. The antibodies of the present invention may be used in any immunoassay method as commonly used in the art. In one embodiment, the immunoassay method of the present invention comprises the steps of contacting the sample containing *Sclerotinia sclerotiorum* antigen with an antibody of the present invention under conditions which allow binding of the *Sclerotinia sclerotiorum* antigen to the antibody; and detecting the presence of the *Sclerotinia sclerotiorum* antigen in the sample. In one embodiment, the detection step comprises performing an ELISA (enzyme-linked immunosorbent assay)-based immunoassay.

In one embodiment, the method of the present invention is performed using an immunoassay kit. The immunoassay kit comprises an antibody of the present invention and all elements needed to perform the desired immunoassay including, without limitation, reagents (for example, an enzyme, a radioisotope, a fluorescent reagent, a luminescent reagent, a chemiluminescent reagent, etc.); a solid surface, such as beads, to which an antibody of the present invention is affixed; buffers; positive and negative controls; and other suitable components. In one embodiment, the invention comprises an immunoassay kit for the detection of *Sclerotinia sclerotiorum*, or *Sclerotinia sclerotiorum* antigens, in a biological sample, comprising an antibody of the present invention, and reagents for detection of specific binding of *Sclerotinia sclerotiorum* antigen to the antibody in the sample. In one embodiment, the immunoassay is an ELISA-based immunoassay.

EXAMPLES

The present invention is described in the following Examples, which are set forth to aid in the understanding of the invention, and should not be construed to limit in any way the scope of the invention as defined in the claims which follow thereafter.

ScFv Construction and Selection:

In order to synthesize the single chain variable fragment (scFv) antibodies, gene fragments from antibodies that can specifically recognize four chosen antigens of interest (i.e. SSPG1d peptide, whole SSPG1d, aspartyl protease peptide and whole *S. sclerotiorum* mycelium) were prepared using the well-established protocol involving the immunization of mice with the four target antigens and the isolation of the antibody-producing spleen cells was utilized. Peptide sequences from the SSPG1d endopolygalacturonase (NGSPTGKPTSGVPI) (SEQ ID NO: 41) and aspartyl protease (MTMDFDSGSSDLWS) (SEQ ID NO: 42) that were predicted to be antigenic based on hydrophobicity plots were synthesized at the Alberta Peptide Institute (University of Alberta) and conjugated to either KLH (keyhole limpet hemocyanin) or BSA (bovine serum albumin). The cDNA for the whole SSPG1d protein (kindly provided by Dr. D. Hegedus, AAFC, Saskatoon, Canada) was subcloned into a bacterial expression vector for subsequent overexpression in *E. Coli* bacterial cells, which was followed by purification by immobilized metal affinity chromatography. The whole fungal mycelial antigen sample was prepared by growing the fungus in a low salt liquid media supplemented with pectin for a period of five days with agitation, after which the mycelia were collected and washed with phosphate buffered saline (PBS) in order to eliminate any residual secreted proteins.

All of the mouse immunizations, test bleeds, exsanguinations and spleen removals were performed at the Biological Sciences Animal Services facilities (University of Alberta). For each antigen, five 4-5 week old BALB/c mice were immunized and for the primary immunizations, the four antigens were emulsified in Freund's complete adjuvant (Difco), however, all of the boost injections were performed with Freund's incomplete adjuvant (Difco). During each immunization the mice were injected both subcutaneously and intraperitoneally with 100 μL of antigen solution at each site. Periodic test bleeds were assayed to determine antibody titres and once sufficiently high titres were reached (≧10,000), the mice were euthanized, exsanguinated and the spleens were collected. Total RNA and messenger RNA (mRNA) were isolated from the splenocytes using the RNeasy Mini Kit (Qiagen) and the mRNA Purification kit (GE Healthcare) and the corresponding cDNA was synthesized using the First Strand cDNA Synthesis Kit (GE Healthcare), after which the variable heavy chain ($V_H$) and variable light chain ($V_L$) antibody fragments were PCR amplified using the primers listed in Table 1 for final assembly in the orientation $V_L$-$(G_4S)_4V_H$.

TABLE 1

Primer sequences used to assemble the scFv antibody genes.

| | | |
|---|---|---|
| Primer VL back: | | |
| | | 5' FLAG VL3' |
| scback | (SEQ ID NO:43) | ttactcgcggcccagccggccatggcggactacaaaG |
| | | 5' FLAG VL 3' |
| LB1 | (SEQ ID NO:44) | gccatggcggactacaaaGAYATCCAGCTGACTCAGCC |
| LB2 | (SEQ ID NO:45) | gccatggcggactacaaaGAYATTGTTCTCWCCCAGTC |
| LB3 | (SEQ ID NO:46) | gccatggcggactacaaaGAYATTGTGMTMACTCAGTC |
| LB4 | (SEQ ID NO:47) | gccatggcggactacaaaGAYATTGTGYTRACACAGTC |
| LB5 | (SEQ ID NO:48) | gccatggcggactacaaaGAYATTGTRATGACMCAGTC |
| LB6 | (SEQ ID NO:49) | gccatggcggactacaaaGAYATTMAGATRAMCCAGTC |
| LB7 | (SEQ ID NO:50) | gccatggcggactacaaaGAYATTCAGATGAYDCAGTC |
| LB8 | (SEQ ID NO:51) | gccatggcggactacaaaGAYATYCAGATGACACAGAC |
| LB9 | (SEQ ID NO:52) | gccatggcggactacaaaGAYATTGTTCTCAWCCAGTC |
| LB10 | (SEQ ID NO:53) | gccatggcggactacaaaGAYATTGWGCTSACCCAATC |
| LB11 | (SEQ ID NO:54) | gccatggcggactacaaaGAYATTSTRATGACCCARTC |
| LB12 | (SEQ ID NO:55) | gccatggcggactacaaaGAYRTTKTGATGACCCARAC |
| LB13 | (SEQ ID NO:56) | gccatggcggactacaaaGAYATTGTGATGACBCAGKC |
| LB14 | (SEQ ID NO:57) | gccatggcggactacaaaGAYATTGTGATAACYCAGGA |
| LB15 | (SEQ ID NO:58) | gccatggcggactacaaaGAYATTGTGATGACCCAGWT |
| LB16 | (SEQ ID NO:59) | gccatggcggactacaaaGAYATTGTGATGACACAACC |
| LB17 | (SEQ ID NO:60) | gccatggcggactacaaaGAYATTTTGCTGACTCAGTC |
| LBλ | (SEQ ID NO:61) | gccatggcggactacaaaGATGCTGTTGTGACTCAGGAATC |
| Primer VL for: | | |
| | | 5' $(Gly_4Ser)_3$-linker VL 3' |
| LF1 | (SEQ ID NO:62) | ggagccgccgccgcc(agaaccaccaccacc)$_2$ACGTTTGATTTCCAGCTTGG |
| LF2 | (SEQ ID NO:63) | ggagccgccgccgcc(agaaccaccaccacc)$_2$ACGTTTTATTTCCAGCTTGG |
| LF4 | (SEQ ID NO:64) | ggagccgccgccgcc(agaaccaccaccacc)$_2$ACGTTTTATTTCCAACTTTG |

TABLE 1-continued

Primer sequences used to assemble the scFv antibody genes.

```
LF5   (SEQ ID NO:65)  ggagccgccgccgcc(agaaccaccaccacc)2ACGTTTCAGCTCCAGCTTGG
LFλ   (SEQ ID NO:66)  ggagccgccgccgcc(agaaccaccaccacc)2ACCTAGGACAGTCAGTTTGG Primer VH back:

5'    (Gly4Ser)2-linker  BamHI  VH                    3'
HB1   (SEQ ID NO:67)  ggcggcggcggctccggtggtggtggatccGAKGTRMAGCTTCAGGAGTC
HB2   (SEQ ID NO:68)  ggcggcggcggctccggtggtggtggatccGAGGTBCAGCTBCAGCAGTC
HB3   (SEQ ID NO:69)  ggcggcggcggctccggtggtggtggatccCAGGTGCAGCTGAAGSASTC
HB4   (SEQ ID NO:70)  ggcggcggcggctccggtggtggtggatccGAGGTCCARCTGCAACARTC
HB5   (SEQ ID NO:71)  ggcggcggcggctccggtggtggtggatccCAGGTYCAGCTBCAGCARTC
HB6   (SEQ ID NO:72)  ggcggcggcggctccggtggtggtggatccCAGGTYCARCTGCAGCAGTC
HB7   (SEQ ID NO:73)  ggcggcggcggctccggtggtggtggatccCAGGTCCACGTGAAGCAGTC
HB8   (SEQ ID NO:74)  ggcggcggcggctccggtggtggtggatccGAGGTGAASSTGGTGGAATC
HB9   (SEQ ID NO:75)  ggcggcggcggctccggtggtggtggatccGAVGTGAWGYTGGTGGAGTC
HB10  (SEQ ID NO:76)  ggcggcggcggctccggtggtggtggatccGAGGTGCAGSKGGTGGAGTC
HB11  (SEQ ID NO:77)  ggcggcggcggctccggtggtggtggatccGAKGTGCAMCTGGTGGAGTC
HB12  (SEQ ID NO:78)  ggcggcggcggctccggtggtggtggatccGAGGTGAAGCTGATGGARTC
HB13  (SEQ ID NO:79)  ggcggcggcggctccggtggtggtggatccGAGGTGCARCTTGTTGAGTC
HB14  (SEQ ID NO:80)  ggcggcggcggctccggtggtggtggatccGARGTRAAGCTTCTCGAGTC
HB15  (SEQ ID NO:81)  ggcggcggcggctccggtggtggtggatccGAAGTGAARSTTGAGGAGTC
HB16  (SEQ ID NO:82)  ggcggcggcggctccggtggtggtggatccCAGGTTACTCTRAAACWGTSTG
HB17  (SEQ ID NO:83)  ggcggcggcggctccggtggtggtggatccCAGGTCCAACTVCAGCARCC
HB18  (SEQ ID NO:84)  ggcggcggcggctccggtggtggtggatccGATGTGAACTTGGAAGTGTC
HB19  (SEQ ID NO:85)  ggcggcggcggctccggtggtggtggatccGAGGTGAAGGTCATCGAGTC Primer VH for:

5'EcoRI         3'
scfor (SEQ ID NO:86)  ggaattcggccccccgag

5'   EcoRI            VH                3'
HF1   (SEQ ID NO:87)  ggaattcggccccgaggcCGAGGAAACGGTGACCGTGGT
HF2   (SEQ ID NO:88)  ggaattcggccccgaggcCGAGGAGACTGTGAGAGTGGT
HF3   (SEQ ID NO:89)  ggaattcggccccgaggcCGCAGAGACAGTGACCAGAGT
HF4   (SEQ ID NO:90)  ggaattcggccccgaggcCGAGGAGACGGTGACTGAGGT
```

Following gel purification of the PCR amplified antibody fragments, the ends of the scFv genes were digested with the restriction enzyme SfiI (New England Biolabs) for subsequent insertion into SfiI-digested pAK100 and/or pJB12 vectors, which were kindly provided by Dr. Andreas Pluckthun (University of Zurich). The construction of the phage display scFv library, panning and phage rescue were performed essentially as described in Krebber et al. (1997) and Tout et al. (2001).

Bacterial Expression of ScFv and Functional Determination:

The scFv genes of the positive clones were PCR amplified with sequence specific primers for subsequent insertion into bacterial expression pET vectors (Novagen), which allow for the expression of the scFv genes in *E. coli* as polyhistidine tagged proteins, thereby facilitating one-step protein purification using $Ni^{2+}$-nitrilotriacetate affinity chromatography resin (Qiagen). The bacterially-expressed protein was found to be insoluble, which necessitated the use of denaturing conditions throughout the protein purification procedure. In order to generate functional proteins, the denatured scFvs were refolded using the method described in Das et al. (2004).

To determine whether or not the refolded scFv proteins were functional, ELISAs were performed whereby 8-well Flat Bottom Immuno Modules (Maxisorp)(Nunc) were coated with either the SSPG1d peptide, aspartyl protease peptide, whole mycelia, or culture filtrate containing secreted SSPG1d enzyme. The culture filtrate was prepared by growing *S. sclerotiorum* in liquid minimal salts media supplemented with 1% pectin for five days with agitation. The mycelia were then removed and the resulting medium, which contained the proteins secreted by the fungus, was used to coat wells for ELISA. After blocking the wells with a 2% BSA/PBS solution, the refolded scFvs were added to the coated wells in addition to uncoated wells, which served as controls. After washing with PBS containing 0.05% Tween-20 and PBS alone, a secondary antibody, which was a horseradish peroxidase (HRP)-conjugated anti-polyhistidine antibody, was added to each of the wells. A second 0.05% Tween-20/PBS and PBS alone wash was followed by addition of the Sure Blue Reserve TMB Microwell Peroxidase Substrate (KPL), which served as the colorimetric substrate. The reaction was stopped with HCl and the absorbance values were measured at 450 nm using a microplate reader. For the scFv specific for the SSPG1d peptide, the determination of the Kd value was also performed as described in Cao et al. (1998) and Friguet et al. (1985).

ScFv-Antifungal Protein Fusion Construction:

The cDNA for the defensin and chitinase genes that were used were isolated using the First Strand cDNA Synthesis Kit (GE Healthcare) and specific primers, and then linked to the scFv-mycelia (monomer) gene using splicing by overlap extension (SOE). The scFv and antifungal proteins were linked by a short peptide linker $(G_4S)_2$.

Inhibition Experiment:

To determine if the refolded scFv specific for the whole mycelia could inhibit the growth of *S. sclerotiorum*, an in vitro growth inhibition experiment was performed. Briefly, 1 cm agar plugs from the outer edges of a 3 day old fungal culture maintained on potato dextrose agar (PDA) media were placed mycelia-side down on 100 μL of either filter-sterilized 100 mM Tris, pH 8 (control) or refolded scFv (27 ng/μL) inside of an empty and sterile Petri dish. The Petri dish was covered, sealed with plastic film and then left at room temperature overnight. The treated agar plugs were then placed mycelia-side down on fresh PDA plates and the radial fungal growth from each of the agar plugs was monitored.

During the panning of the generated phage display libraries the absorbance values at 450 nm for the identified positive clones were 0.871 (SSPG1d peptide), 0.098 (whole SSPG1d), 0.343 (aspartyl protease) and 0.260 (whole fungal mycelia). All of the reported absorbances are values above background. The DNA and the amino acid sequences for the positive scFv clones specific for each of the four targeted antigens, in addition to the DNA and amino acid sequences for the polyhistidine tagged scFv clones are provided in FIGS. 1A-M and 2A-G, respectively. FIG. 3 shows a representative 13% SDS-PAGE gel indicating the level of purity that was achievable for the scFv antibodies following protein purification. The relative purity of the scFv protein (≧95%) may indicate that any inhibitory activity observed in subsequent in vitro assays or experiments using the purified protein was likely caused by the scFv and is not due to the presence of any contaminating bacterial protein that was inadvertently co-purified.

Figure 4A:
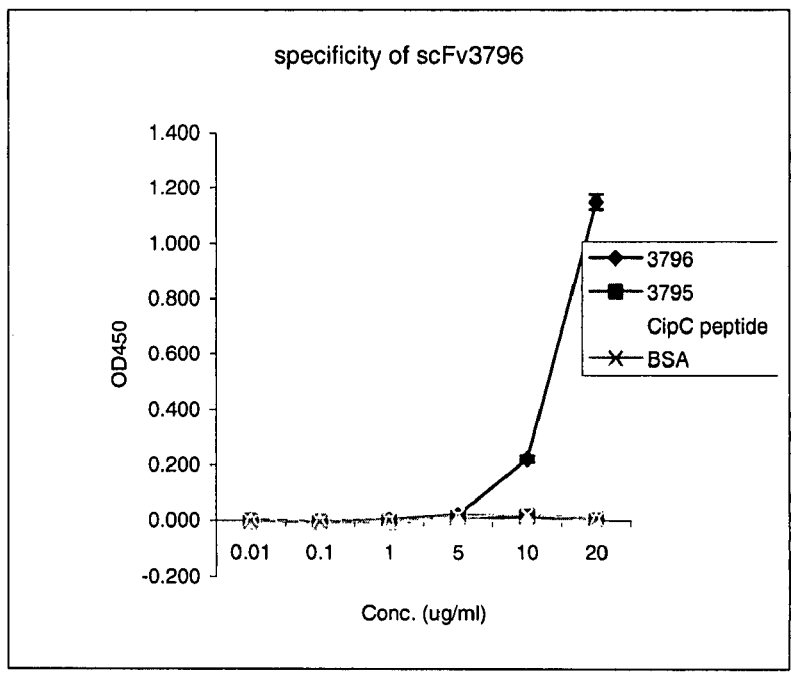
FIGS. 4A, 4B and 4C show graphical representations of functional activity of scFv against SSPG1d peptide (FIG. 4A), scFv against SSPG1d whole protein (FIG. 4B), and the dissociation constant for the scFv against the SSPG1d peptide (FIG. 4C).
Figure 4B:
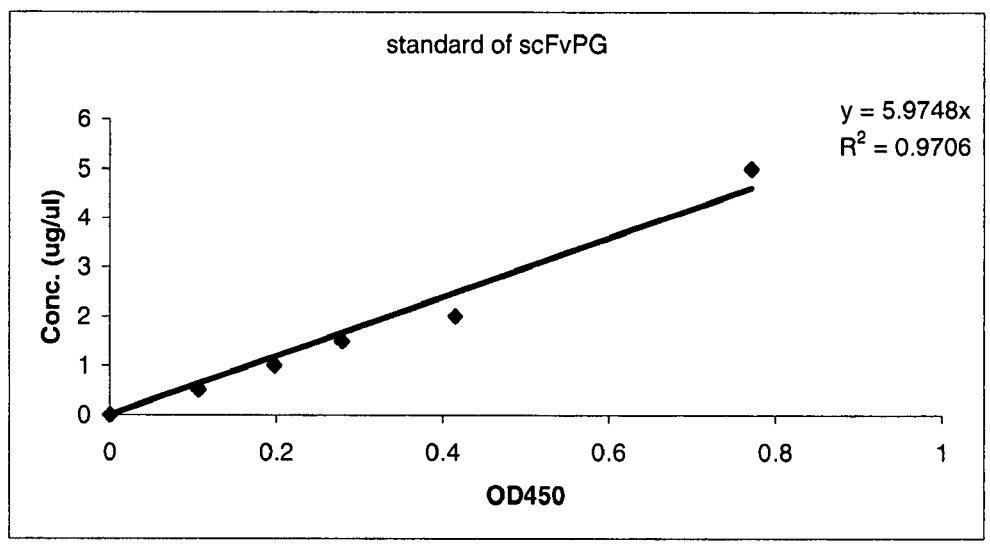
Figure 4C:
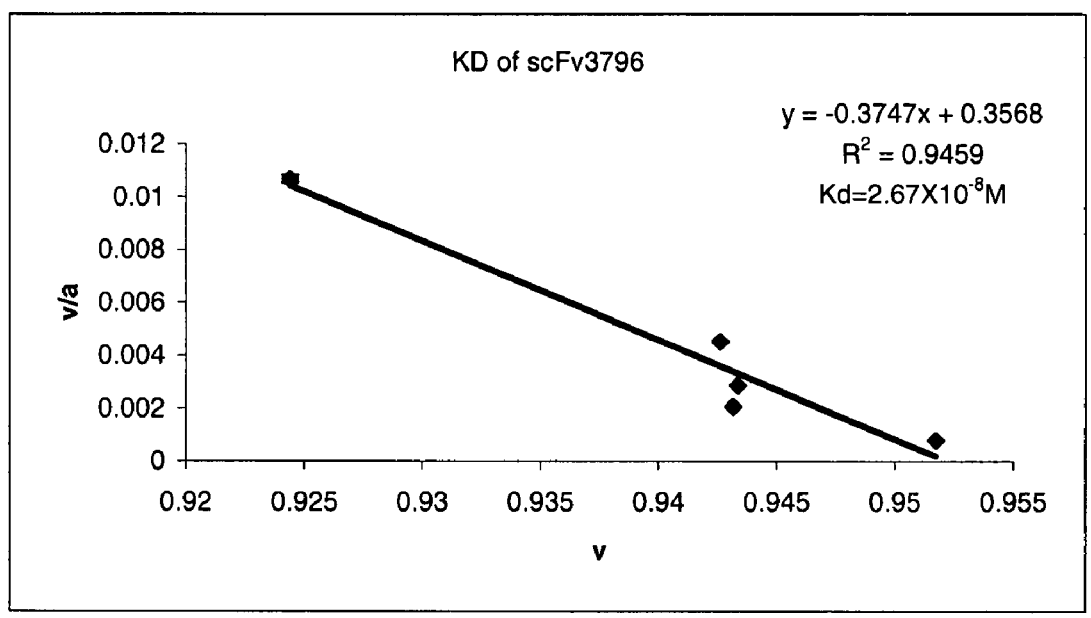

The assays that were performed to test the activity of the refolded bacterially-expressed scFv antibody specific for the whole fungal mycelia found that at 10 μg/mL scFv concentration the absorbance value was 0.343 above the background, while the activities of the scFv antibodies specific for the SSPG1d peptide and whole protein are summarized in FIGS. 4A-4C. These absorbances indicate that the refolded scFv antibodies appear to still be able to recognize and specifically bind to their respective antigens, indicating that refolding of the proteins was relatively successful.

Figure 5:
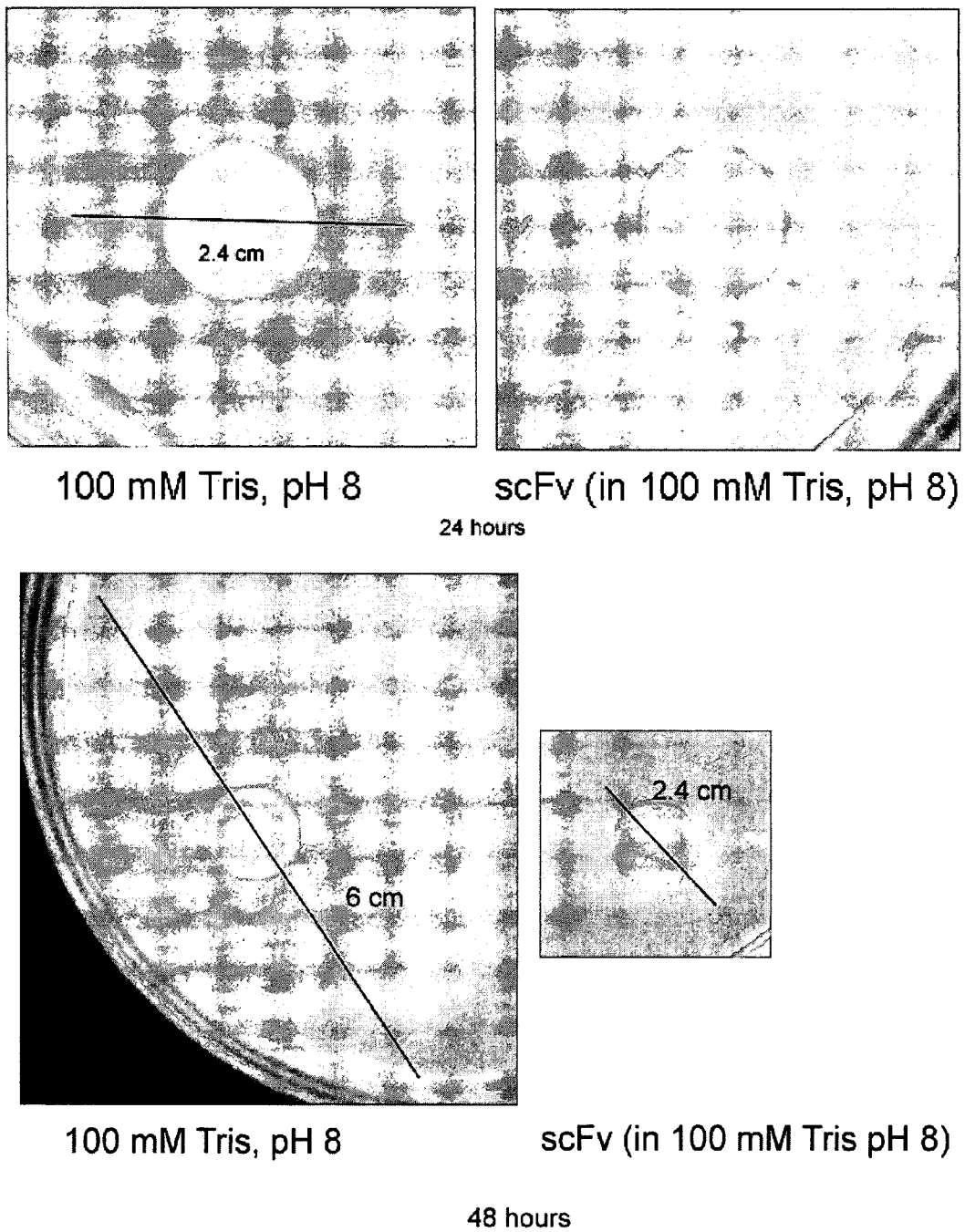
FIG. 5 shows the results of a growth inhibition experiment using scFv-mycelia showing delayed growth of the scFv-treated fungal agar plug.

FIG. 5 shows the results that were generated from the growth inhibition experiment using the scFv specific for the mycelia. It appears that the scFv treatment in fact interferes with the ability of the fungus to grow as demonstrated by the delayed growth of the mycelia as compared to the growth from the buffer-treated control agar plug.

Figure 6:
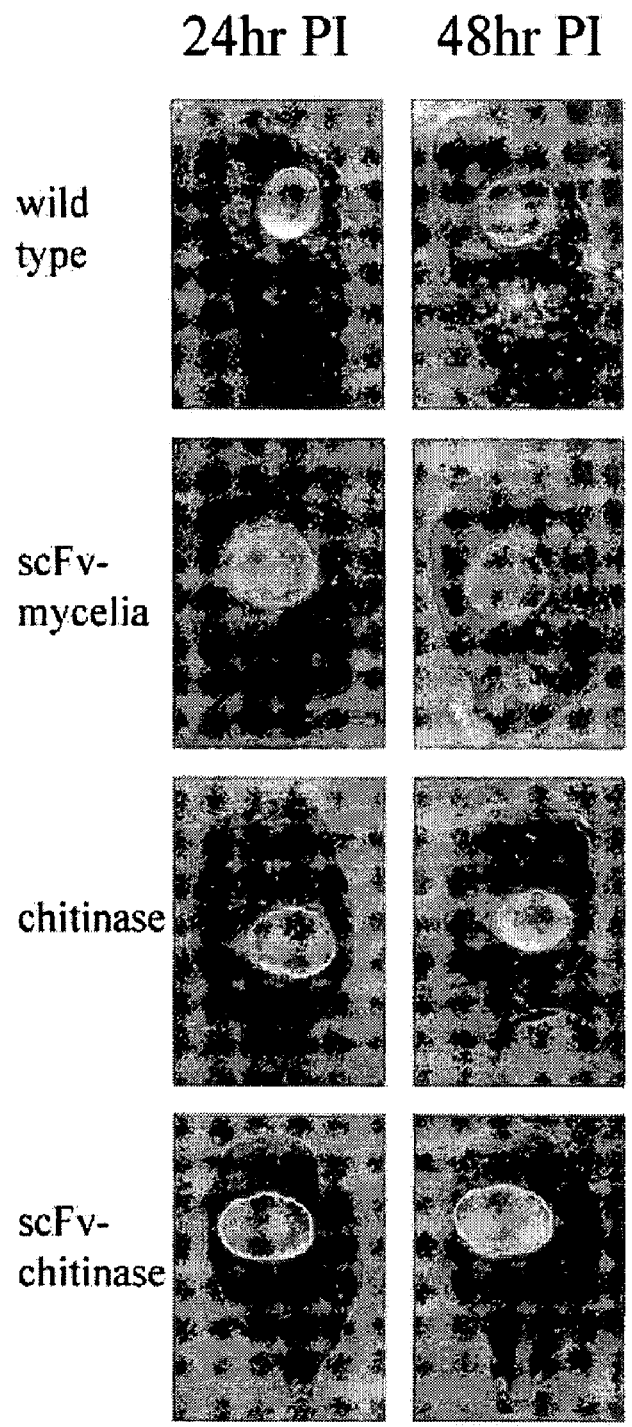
FIG. 6 shows the results of fungal inoculation experiments in which *Arabidopsis thaliana* plants transformed with scFv-mycelia (monomer) or scFv-antifungal protein fusions

Experiments with *Arabidopsis thaliana* plants that had been transformed with scFv-mycelia or scFv-antifungal protein fusions were performed to determine if the scFv-mycelia or scFv-antifungal protein fusions could confer increased tolerance or resistance to *S. sclerotiorum* infection. FIG. 6 summarizes some results of the fungal inoculation of *A. thaliana* experiments and shows that the scFv-chitinase fusion appears to confer tolerance/resistance to *S. sclerotiorum* infection as compared to the wild type control and a transgenic plant expressing scFv alone.

Diagnostic Assay:

In order to determine the utility of the scFv antibodies in an antibody-based diagnostic assay to detect infestation of *S. sclerotiorum*, experiments were performed to assess the specificity of the antibodies. ELISA-based assays in which the scFv-mycelia (monomer) was tested to see if it had affinity for four different fungi showed that the antibody was able to bind to both *S. sclerotiorum* and *Botrytis cinerea* mycelia, but did not bind to *Leptosphaeria maculans* or *Alternaria brasssicae*, which are two other phytopathogenic fungi capable of causing significant yield or quality losses in canola production. Table 2 shows the absorbance values obtained by ELISA.

Figure 7:
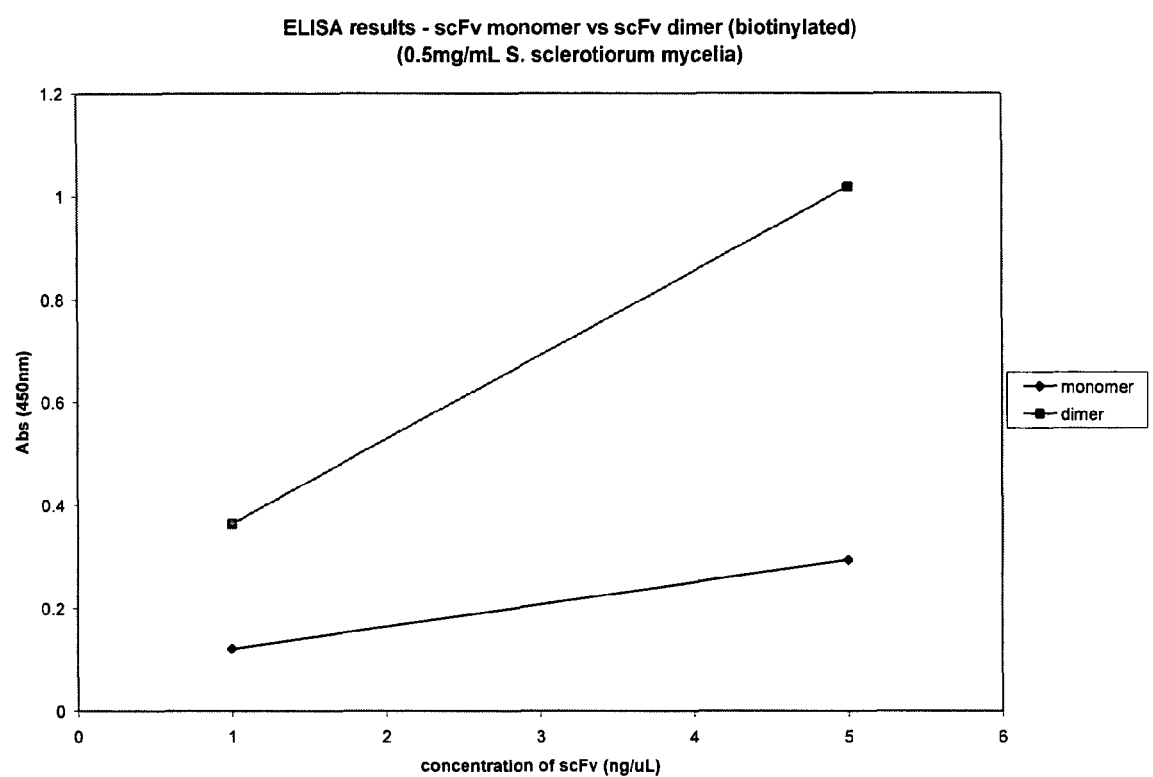
FIG. 7 shows a graphical representation of the improved signals obtained from ELISAs using dimerized scFv-mycelia as compared to the scFv-mycelia (monomer).

Comparison of scFv-Mycelia (Monomer) and scFv-Mycelia (Dimer):

FIG. 7 is a graphical representation of the higher signals obtained from the scFv-mycelia (dimer) compared to the scFv-mycelia (monomer) based on ELISA results, which may indicate improved binding affinity/efficiency of the dimerized scFv-mycelia compared with the monomer.

TABLE 2

| Specificity of scFv-mycelia (monomer) based on ELISA | |
|---|---|
| Fungus | Absorbance (450 nm) |
| S. sclerotiorum | 0.298 |
| B. cinerea | 0.225 |
| L. maculans | 0.054 |
| A. brassicae | 0.055 |

REFERENCES

The following references are referred to above, the contents of which are incorporated herein by reference.

Ausubel, F. M., et al. (2000) Current Protocols in Molecular Biology. John Wiley & Sons, New York.

Cao, Y., Christian, S, and Suresh, M. R. (1998). J. Immunol. Methods. 220, 85-91.

Das, D., Kriangkum, J., Nagata, L. P., Fulton, R. E. and Suresh, M. R. (2004). J. Virol. Methods. 117, 169-177.

Friguet, B., Chaffotte, A. F., Ohaniance, L. D. and Goldberg, M. E. (1985). J. Immunol. Methods. 77, 305-319.

Krebber, A., Bornhauser, S., Burmester, J., Honegger, A., Willuda, J., et al. (1997). J. Immunol. Methods. 201, 35-55.

Sambrook, J., Fritsch, E. F. and Maniatis. T. (1989) Molecular Cloning: A Laboratory Manual. Second ed. Cold Spring Harbor Press, New York.

Tout, N. L., Yau, K. Y. F., Trevors, J. T., Lee, H. and Hall, J. C. (2001). J. Agric. Food Chem. 49, 3628-3637.

What is claimed is:

1. An isolated antibody which specifically binds to *Sclerotinia sclerotiorum* SSPG1d antigen, the antibody comprising a single chain variable fragment (scFv), the scFv comprising the amino acid sequence of SEQ ID NO: 2 or SEQ ID NO: 4.

2. The antibody of claim 1, further comprising a polyhistidine tag.

3. The antibody of claim 2, comprising the amino acid sequence of SEQ ID NO: 28 or SEQ ID NO: 30.

4. The antibody of claim 1 linked to an anti-fungal protein.

5. An immunoassay method to detect *Sclerotinia sclerotiorum* in a biological sample utilizing an antibody of claim 1, the method comprising the steps of:

(a) contacting the sample containing *Sclerotinia sclerotiorum* with the antibody of claim 1 under conditions which allow binding of the *Sclerotinia sclerotiorum* SSPG1d antigen to the antibody; and (b) detecting the presence of the *Sclerotinia sclerotiorum* SSPG1d antigen in the sample.

6. The method of claim 5, wherein the detection step comprises performing an ELISA-based immunoassay.

7. An immunoassay kit for the detection of *Sclerotinia sclerotiorum* in a biological sample, the immunoassay kit comprising an antibody of claim 1, and reagents for detection of specific binding of *Sclerotinia sclerotiorum* SSPG1d antigen to the antibody in the sample.

8. The kit of claim 7, wherein the immunoassay is an ELISA-based immunoassay.

* * * * *